(12) United States Patent
Leysen et al.

(10) Patent No.: US 8,912,209 B2
(45) Date of Patent: *Dec. 16, 2014

(54) ROCK INHIBITORS

(71) Applicant: Amakem NV, Diepenbeek (BE)

(72) Inventors: Dirk Leysen, Diepenbeek (BE); Oliver Defert, Diepenbeek (BE); Nadzeya Kaval, Diepenbeek (BE); Petra Blom, Destelbergen (BE); Sandro Boland, Burdinne (BE)

(73) Assignee: Amakem NV, Diepenbeek (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/897,524

(22) Filed: May 20, 2013

(65) Prior Publication Data

US 2013/0252975 A1    Sep. 26, 2013

Related U.S. Application Data

(62) Division of application No. 13/582,195, filed as application No. PCT/EP2011/053343 on Mar. 4, 2011.

(30) Foreign Application Priority Data

Mar. 2, 2010 (GB) .................................. 1003395.9
Nov. 10, 2010 (GB) .................................. 1018996.7

(51) Int. Cl.
| | | |
|---|---|---|
| A01N 43/40 | (2006.01) | |
| A61K 31/435 | (2006.01) | |
| A61K 31/44 | (2006.01) | |
| A01N 43/42 | (2006.01) | |
| C07D 401/12 | (2006.01) | |
| C07D 239/42 | (2006.01) | |
| C07D 213/75 | (2006.01) | |
| C07D 471/04 | (2006.01) | |
| C07D 409/12 | (2006.01) | |
| C07D 405/12 | (2006.01) | |
| C07D 493/04 | (2006.01) | |

(52) U.S. Cl.
CPC ............ *C07D 213/75* (2013.01); *C07D 401/12* (2013.01); *C07D 239/42* (2013.01); *C07D 471/04* (2013.01); *C07D 409/12* (2013.01); *C07D 405/12* (2013.01); *C07D 493/04* (2013.01)
USPC ............................. 514/277; 514/279; 514/290

(58) Field of Classification Search
CPC . A61K 31/166; A61K 31/235; A61K 31/435; A61K 31/44

USPC .......................................... 514/277, 279, 290
See application file for complete search history.

(56) References Cited

U.S. PATENT DOCUMENTS

| | | | |
|---|---|---|---|
| 4,997,834 | A | 3/1991 | Muro et al. |
| 6,369,086 | B1 | 4/2002 | Davis et al. |
| 6,369,087 | B1 | 4/2002 | Whittle et al. |
| 6,372,733 | B1 | 4/2002 | Caldwell et al. |
| 6,372,778 | B1 | 4/2002 | Tung et al. |
| 2009/0233960 | A1 | 9/2009 | Van Rompaey et al. |

FOREIGN PATENT DOCUMENTS

| | | |
|---|---|---|
| EP | 0370498 A2 | 5/1990 |
| EP | 0721331 B1 | 7/1996 |
| WO | 2007006547 A1 | 1/2007 |
| WO | 2007042321 A2 | 4/2007 |

OTHER PUBLICATIONS

Search Report for PCT/EP2011/053343 dated May 12, 2011.
International Preliminary Report on Patentability for PCT/EP2011/053343 dated May 9, 2012.
Elections Restriction for U.S. Appl. No. 13/582,195 dated Feb. 26, 2013.
Office Action for U.S. Appl. No. 13/582,195 dated Apr. 16, 2013.
Arita, et al., ROCK As A Therapeutic Target of Diabetic Retinopathy, Journal of Ophthalmology, 2010, pp. 1-9, vol. 2010, Article ID 175163, Hindawi Publishing Corporation, Japan.
Hirata, et al., Y-27632. A Rho-Associated Protein Kinase Inhibitor, Attenuates Neuronal Cell Death After Transietn Retinal Ischemia, 2008, pp. 51-59, vol. 246, Graefes Arch Clin Exp Ophthalmol, Japan.
Sagawa, et al., A Novel ROCK Inhibitor, Y-39983, Promotes Regeneration of Crushed Axon of Retinal Ganglion Cells Into the Optic Nerve of Adult Cats, 2007, pp. 230-240, vol. 205, Journal of Experimental Neurology, Japan.

*Primary Examiner* — Yong Chong
(74) *Attorney, Agent, or Firm* — Dinsmore & Shohl LLP

(57) ABSTRACT

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease. In addition, the invention relates to methods of treatment and use of said compounds in the manufacture of a medicament for the application to a number of therapeutic indications including sexual dysfunction, inflammatory diseases, ophthalmic diseases and Respiratory diseases.

12 Claims, No Drawings

ROCK INHIBITORS

CROSS REFERENCE TO RELATED APPLICATIONS

This application is a division of U.S. patent application Ser. No. 13/582,195 filed Aug. 31, 2012, entitled HETEROCYCLIC AMIDES AS ROCK INHIBITORS, which application is a national phase entry of PCT/EP11/53343 filed Mar. 4, 2011, which claims priority to Great Britain Application No. 1003395.9 filed Mar. 2, 2010 and Great Britan Application No. 1018996.7 filed Nov. 10, 2010. The entire contents of said application is hereby incorporated by reference.

FIELD OF THE INVENTION

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease.

BACKGROUND OF THE INVENTION

The serine/threonine protein kinase ROCK consists in humans of two isoforms ROCK I and ROCK II. ROCK I is encoded on chromosome 18 whereas ROCK II, also called Rho-kinase, is located on chromosome 12. They both have a molecular weight close to 160 kDa. They share an overall homology of 65% while being 95% homologous in their kinase domains. Despite their sequence similarity, they differ by their tissue distributions. The highest levels of expression for ROCK I are observed in heart, lung and skeletal tissues whereas ROCK II is mostly expressed in brain. Recent data indicate that these two isoforms are partially function redundant, ROCK I being more involved in immunological events, ROCK II in smooth muscle function. The term ROCK refers to ROCK I (aka ROK-β, p160ROCK, or Rho-kinase β) and ROCK II (aka ROCK-α or Rho-kinase α).

ROCK activity has been shown to be enhanced by GTPase RhoA that is a member of the Rho (Ras homologous) GTP-binding proteins. The active GTP-bound state of RhoA interacts with Rho-binding domain (RBD) of ROCK that is located in an autoinhibitory carboxyl-terminal loop. Upon binding, the interactions between the ROCK negative regulatory domain and the kinase domain are disrupted. The process enables the kinase to acquire an open conformation in which it is fully active. The open conformation is also induced by the binding of lipid activators such as arachidonic acid to the PH domain in the kinase carboxyl-terminal domain. Another activation mechanism has been described during apoptosis and involves the cleavage of carboxyl terminus by caspase-3 and -2 (or granzyme B) for ROCK I and II, respectively.

ROCK plays an important role in various cellular functions such as smooth muscle contraction, actin cytoskeleton organization, platelet activation, downregulation of myosin phosphatase cell adhesion, -migration, -proliferation and survival, thrombin-induced responses of aortic smooth muscle cells, hypertrophy of cardiomyocytes, bronchial smooth muscle contraction, smooth muscle contraction and cytoskeletal reorganization of non-muscle cells, activation of volume-regulated anion channels, neurite retraction, wound healing, cell transformation and gene expression. ROCK also acts in several signaling pathways that are involved in auto-immunity and inflammation. ROCK has been shown to play a part in the activation of NF-κB, a critical molecule that leads to the production of TNF and other inflammatory cytokines. ROCK inhibitors are reported to act against TNF-alpha and IL-6 production in lipopolysaccharide (LPS)-stimulated THP-1 macrophages. Therefore, ROCK inhibitors provide a useful therapy to treat autoimmune and inflammatory diseases as well as oxidative stress.

In conclusion, ROCK is a major control point in smooth muscle cell function and a key signaling component involved in inflammatory processes in various inflammatory cells as well as fibrosis and remodeling in many diseased organs. There are clear indications that ROCK is involved in the pathogenesis of many diseases, including asthma, COPD and glaucoma. In addition, ROCK has been implicated in various diseases and disorders including eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupus erythematosus, spasm, hypertension, chronic obstructive bladder disease, premature birth, infection, allergy, obesity, pancreatic disease and AIDS.

ROCK appears to be a safe target, as exemplified by knock-out models and a large number of academic studies. These KO mice data, in combination with post-marketing surveillance studies with Fasudil, a moderately potent ROCK inhibitor used for the treatment of vasospasm after subarachnoid hemorrhage, indicate that ROCK is a genuine and significant drug target.

ROCK inhibitors would be useful as therapeutic agents for the treatment of disorders implicated in the ROCK pathway. Accordingly, there is a great need to develop ROCK inhibitors that are useful in treating various diseases or conditions associated with ROCK activation, particularly given the inadequate treatments currently available for the majority of these disorders. Some non-limiting examples are glaucoma, asthma and COPD.

Glaucoma, a group of diseases that may cause vision loss and blindness due to damage of the optic nerve, is caused by increased intra-ocular pressure. It is a common cause of adult blindness, mostly a chronic disease that requires life-long control after diagnosis. There is a need for improved treatment as the current therapy does only control and not cure the disease and further suffers from irritation, local and systemic side effects. In addition, additional positive effects, as the anti-inflammatory and nerve regenerating components of ROCK inhibitors, would be highly preferred. Reference ROCK inhibitors, such as Y-27632 cause changes in cell shape and decrease stress fibers, focal adhesions and MLC phosphorylation in cultured human TM cells; they relax human trabecular meshwork in vitro, relax human Schlemm's canal endothelial cells in vitro and when topically applied to animals give a significant increase in trabecular outflow, resulting into a strong lowering of intra ocular pressure.

Allergic asthma is a chronic inflammatory airway disorder that results from maladaptive immune responses to ubiquitous environmental proteins in genetically susceptible persons. Despite reasonably successful therapies, the prevalence increases as these therapies do not cure; there are still exacerbations and an increasing number of non-responders. New, effective and steroid-sparing treatments that tackle all components of the disease are required.

Chronic Obstructive Pulmonary Disease (COPD) represents a group of diseases characterized by irreversible limitation of airflow, associated with abnormal inflammatory response, bronchoconstriction and remodeling and destruction of the tissue of the lung. It is one of the leading causes of death worldwide, with a steadily increasing prevalence. There is an urgent need for novel therapeutic approaches as the current regimen is inadequate. Until now only bronchodilators are used, since glucocorticoids have limited or no effect. Reference ROCK inhibitors, such as Y-27632 relax human isolated bronchial preparations, inhibit increases in airway resistance in anaesthetised animals, potentiate relaxing effects of β-agonists in vitro and in vivo and give rapid bronchodilatation upon inhalation. In addition, ROCK inhibitors block tracheal smooth muscle contractions induced by $H_2O_2$, the clinical marker for oxidative stress.

Related to airway inflammation, ROCK inhibitors counteract the increase in trans-endothelial permeability mediated by inflammatory agents, maintain the endothelial barrier integrity, inhibit the influx of eosinophils after ovalbumin challenge in vivo, protect against lung edema formation and neutrophile migration, suppress airway HR to metacholine and serotonin in allergic mice and block LPS-induced TNF release. With respect to airway fibrosis and remodeling, ROCK inhibitors block the induced migration of airway smooth muscle cells. In vitro evidences for the role of ROCK in airway remodeling were obtained in human lung carcinoma cell line, bovine tracheal smooth muscle cells and human airway smooth muscle. In vivo proof for a role of ROCK in fibrosis in general was generated with mice which exhibited attenuated myocardial fibrosis in response to the partial deletion of ROCK. The attenuation of myocardial fibrosis by Y-27632 in response to myocardial infarction and by fasudil in the case of congestive heart failure in a chronic hypertensive rat model brings additional indications of ROCK importance in remodeling. Finally, ROCK inhibitors increase apoptotic cell loss of smooth muscle cells.

The human sexual response in both males and females results from an interplay of physiological, psychological, and hormonal factors. One common aspect of the sexual response in males and females, however, is the vasoactive response, which results in engorgement of the sexual tissues of the genitalia with blood as a result of vascular smooth muscle relaxation in response to sexual stimulation. Thus, blood pressure and blood flow inside the penis and clitoris increase when smooth muscles of the pudental vasculature relax. This arterial influx of blood causes enlargement of the penile or clitoral corpora cavernosa and results in erection.

Impotence (erectile dysfunction in men) is generally defined as an inability to achieve and sustain an erection sufficient for satisfactory sexual performance and intercourse. Impotence can be due to psychological disturbances, neurological abnormalities, or other physiological disturbances including hormonal deficiencies or, a combination of causes. In the United States, male impotence is estimated to affect 40% of men at age 40, increasing with age to about 50% by 50 years, and is as high as 67% by the age of 70. It is estimated that up to 30 million males may suffer from impotence in the U.S.

Females can also have sexual dysfunction that increases with age and is associated with the onset of menopause and increased risk of vascular disorders. Thus, similar to men, sexual arousal in women is accompanied, at least in part, by increased blood flow which engorges the clitoris. Blood flow to the vagina also increases vaginal lubrication. Thus, female sexual dysfunction can result from an inability to attain or maintain clitoral engorgement and/or vaginal lubrication throughout the period of sexual activity.

Currently, most vasodilators used to treat erectile dysfunction target signal transduction pathways that reduce calcium ion, which is needed to initiate contractile activity in vascular smooth muscle. However, from a physiological standpoint, the initiation of vasoconstriction is a very acute event lasting only seconds to a few minutes. The erectile tissue is maintained in the flaccid state by long-term vasoconstriction through a signal transduction pathway that is calcium-independent. A signal pathway that maintains calcium-independent vasoconstriction is the RhoA/Rho-kinase pathway. ROCK inhibitors are accordingly useful to treat erectile dysfunction. Thus, in one aspect, the present invention comprises a method for treating male or female sexual dysfunction which comprises topical administration to an individual in need thereof of a composition comprising a compound which attenuates Rho-kinase activity in an organ subject to sexual stimulation, and a pharmaceutically acceptable carrier.

Several different classes of ROCK inhibitors are known. The current focus is oncology and cardiovascular applications. Until now, the outstanding therapeutic potential of ROCK inhibitors has only been explored to a limited extent. The reason is the fact that ROCK is such a potent and widespread biochemical regulator, that systemic inhibition of ROCK leads to strong biological effects that are considered as being side effects for the treatment of most of the diseases. Indeed, the medical use of ROCK inhibitors to treat diseases with a strong inflammatory component is hampered by the pivotal role of ROCK in the regulation of the tonic phase of smooth muscle cell contraction. Systemically available ROCK inhibitors induce a marked decrease in blood pressure. Therefore, ROCK inhibitors with different properties are highly required.

For the target specific treatment of disorders by regulating smooth muscle function and/or inflammatory processes and/or remodeling, it is highly desired to deliver a ROCK inhibitor to the target organ and to avoid significant amounts of these drugs to enter other organs. Therefore, local or topical application is desired. Typically, topical administration of drugs has been applied for the treatment of airway-, eye, sexual dysfunction and skin disorders. In addition, local injection/infiltration into diseased tissues further extend the potential medical use of locally applied ROCK inhibitors. Given certain criteria are fulfilled, these local applications allow high drug concentration to be reached in the target tissue. In addition, the incorporation of ROCK inhibitors into implants and stents can further expand the medical application towards the local treatment of CV diseases such as atherosclerosis, coronary diseases and heart failure.

Despite the fact that direct local application is preferred in medical practice, there are concerns regarding drug levels reached into the systemic circulation. For example the treatment of airway diseases by local delivery by for instance inhalation, poses the risk of systemic exposure due to large amounts entering the GI tract and/or systemic absorption through the lungs. For the treatment of eye diseases by local delivery, also significant amounts enter the GI tract and/or systemic circulation due to the low permeability of the cornea, low capacity for fluid, efficient drainage and presence of blood vessels in the eyelids. Also for dermal applications, local injections and implantable medical devices, there is a severe risk of leakage into the systemic circulation. Therefore, in addition to local application, the compounds should preferably have additional properties to avoid significant systemic exposure.

Soft drugs are biologically active compounds that are inactivated once they enter the systemic circulation. This inactivation can be achieved in the liver, but the preferred inactivation should occur in the blood. These compounds, once applied locally to the target tissue/organ exert their desired effect locally. When they leak out of this tissue into the systemic circulation, they are very rapidly inactivated. Thus, soft drugs of choice are sufficiently stable in the target tissue/organ to exert the desired biological effect, but are rapidly degraded in the blood to biologically inactive compounds. In addition, it is highly preferable that the soft drugs of choice have retention at their biological target. This property will limit the number of daily applications and is highly desired to reduce the total load of drug and metabolites and in addition will significantly increase the patient compliance.

In conclusion, there is a continuing need to design and develop soft ROCK inhibitors for the treatment of a wide range of disease states. The compounds described herein and pharmaceutically acceptable compositions thereof are useful for treating or lessening the severity of a variety of disorders or conditions associated with ROCK activation. More specifically, the compounds of the invention are preferably used in the prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeneration and remodeling. For example, the compounds of the invention may be used in the prevention and/or treatment of diseases and disorders such as:

Eye diseases or disorders: including but not limited to retinopathy, optic neuropathy, glaucoma and degenerative retinal diseases such as macular degeneration, retinitis pigmentosa and inflammatory eye diseases.

Airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome Throat, Nose and Ear diseases: including but not limited to sinus problems, hearing problems, toothache, tonsillitis, ulcer and rhinitis, Skin diseases: including but not limited to hyperkeratosis, parakeratosis, hypergranulosis, acanthosis, dyskeratosis, spongiosis and ulceration.

Intestinal diseases; including but not limited to inflammatory bowel disease (IBD), colitis, gastroenteritis, ileus, ileitis, appendicitis and Crohn's disease.

Cardiovascular and vascular diseases: including but not limited to, pulmonary hypertension and pulmonary vasoconstriction.

Inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis.

Neurological disorders: including but not limited to neuropathic pain. The present compounds are therefore suitable for preventing neurodegeneration and stimulating neurogeneration in various neurological disorders.

Proliferative diseases: such as but not limited to cancer of, breast, colon, intestine, skin, head and neck, nerve, uterus, kidney, lung, ovary, pancreas, prostate, or thyroid gland; Castleman disease; leukemia; sarcoma; lymphoma; malignoma; and melanoma.

Kidney diseases: including but not limited to renal fibrosis or renal dysfunction.

Sexual dysfunction: is meant to include both male and female sexual dysfunction caused by a defective vasoactive response. The soft ROCK inhibitors of the present invention may also be used to treat sexual dysfunction arising from a variety of causes. For example, in an embodiment, the soft ROCK inhibitors may be used to treat sexual dysfunction associated with hypogonadism and more particularly, wherein the hypogonadism is associated with reduced levels of androgen hormones. In another embodiment, the soft ROCK inhibitors may be used to treat sexual dysfunction associated with a variety of causes including, but not limited to, bladder disease, hypertension, diabetes, or pelvic surgery. In addition, the soft ROCK inhibitors may be used to treat sexual dysfunction associated with treatment using certain drugs, such as drugs used to treat hypertension, depression or anxiety.

Bone diseases: including but not limited to osteoporosis and osteoarthritis.

In addition, the compounds of the invention may be used in the prevention and/or treatment of diseases and disorders such as benign prostatic hyperplasia, transplant rejection, spasm, chronic obstructive bladder disease, and allergy.

SUMMARY OF THE INVENTION

We have surprisingly found that the compounds described herein act as inhibitors of ROCK, in particular as soft ROCK inhibitors. Compared to art known Rock inhibitors, such as for example described in WO2007/042321, the compounds of the present invention differ in that they are very rapidly converted into functionally inactive compounds such as for example by Paraoxonase 1 (PON1) activity.

PON1 is a Ca2+ dependent serum class A-esterase, which is synthesized in the liver and secreted in the blood, where it associates exclusively with high-density lipoproteins (HDLs). Furthermore, it is able to cleave a unique subset of substrate including organophosphates, arylesters, lactones and cyclic carbonates. Therefore, the Y substituent of the compounds of the present invention, generally represented by formula I hereinbelow, are selected to comprise a substituent selected from the group of arylesters, lactones and cyclic carbonates, more specifically from arylesters and lactones.

Unless a context dictates otherwise, asterisks are used herein to indicate the point at which a mono- or bivalent radical depicted is connected to the structure to which it relates and of which the radical forms part.

Viewed from a first aspect, the invention provides a compound of Formula I or a stereoisomer, tautomer, racemic, metabolite, pro- or predrug, salt, hydrate, or solvate thereof,

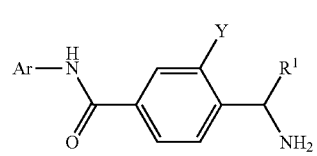

Wherein $R^1$ is selected form the group comprising hydrogen, alkyl or cycloalkyl;

Ar is selected from the group comprising:

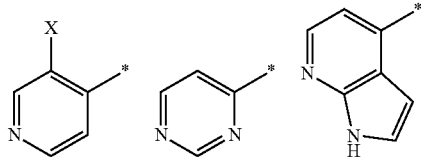

Wherein X is selected from the group comprising hydrogen or halo;

Y is an aryl or heteroaryl substituted with a substituent selected from the group consisting of —C(=O)—OR$^{21}$; —C(=O)—SR$^{22}$; —C(=O)—NR$^3$R$^4$; —NR$^5$R$^6$; —O—C$_{1-6}$alkyl; —S—C$_{1-6}$alkyl; —O—C$_{2-8}$alkenyl; —S—C$_{2-8}$alkenyl; —C$_{1-6}$alkyl; or —C$_{2-8}$alkenyl;

wherein said —O—C$_{1-6}$alkyl; —S—C$_{1-6}$alkyl; —O—C$_{2-8}$alkenyl; —S—C$_{2-8}$alkenyl; —C$_{1-6}$alkyl; or —C$_{2-8}$alkenyl; are each independently substituted with a substituent selected from the group consisting of C(=O)—OR$^{21}$; —C(=O)—SR$^{22}$; —C(=O)—NR$^3$R$^4$; Het$^1$; —O-Het$^2$; and —S-Het$^3$;

R$^3$ is selected from the group consisting of hydrogen; C$_{2-8}$alkenyl substituted with O-Het$^2$ or —S-Het$^3$; or C$_{1-20}$alkyl optionally substituted with 1, 2 or 3 substituents each independently selected from the group consisting of aryl, heteroaryl, C$_{3-6}$cycloalkenyl, —C(=O)—OR$^{21}$, —C(=O)—SR$^{22}$, —C(=O)—NR$^7$R$^8$, Het$^1$, —O-Het$^2$, —S-Het$^3$, —S—C$_{1-6}$alkyl and —O—C$_{1-6}$alkyl;

wherein said —O—C$_{1-6}$alkyl; —S—C$_{1-6}$alkyl; or C$_{3-6}$cycloalkenyl; are each independently substituted with a substituent selected from the group consisting of C(=O)—OR$^{21}$; —C(=O)—SR$^{22}$; —C(=O)—NR$^3$R$^4$; Het$^1$; —O-Het$^2$; and —S-Het$^3$;

R$^4$ is selected from the group consisting of C$_{2-8}$alkenyl substituted with O-Het$^2$ or —S-Het$^3$; or C$_{1-20}$alkyl optionally substituted with 1, 2 or 3 substituents each independently selected from the group consisting of aryl, heteroaryl, C$_{3-6}$cycloalkenyl, —C(=O)—OR$^{21}$, —C(=O)—SR$^{22}$, —C(=O)—NR$^7$R$^8$, Het$^1$, —O-Het$^2$, —S-Het$^3$, —O—C$_{1-6}$alkyl and —O—S$_{1-6}$alkyl;

wherein said —O—C$_{1-6}$alkyl; —S—C$_{1-6}$alkyl; or C$_{3-6}$cycloalkenyl; are each independently substituted with a substituent selected from the group consisting of C(=O)—OR$^{21}$; —C(=O)—SR$^{22}$; —C(=O)—NR$^3$R$^4$; Het$^1$; —O-Het$^2$; and —S-Het$^3$; or;

R$^3$ and R$^4$ together with the nitrogen atom to which they are attached form a heterocycle substituted with one substituent selected from the group consisting of —C(=O)—OR$^{21}$; —C(=O)—SR$^{22}$; —C(=O)—NR$^9$R$^{10}$; Het$^1$; —O-Het$^2$; —S-Het$^3$; C$_{1-6}$alkyl; C$_{1-6}$alkyl-O—C$_{1-4}$alkyl; or C$_{1-6}$alkyl-O—C$_{2-4}$alkenyl; wherein each of said C$_{1-6}$alkyl; C$_{1-6}$alkyl-O—C$_{1-4}$alkyl; or C$_{1-6}$alkyl-O—C$_{2-4}$alkenyl is each independently substituted with 1, 2, or 3 substituents each independently selected from the group consisting of aryl, heteroaryl, C$_{3-6}$cycloalkenyl, —C(=O)—OR$^{21}$; —C(=O)—SR$^{22}$; —C(=O)—NR$^9$R$^{10}$; Het$^1$; —O-Het$^2$; and —S-Het$^3$;

R$^5$ or R$^6$ are independently selected from the group consisting of hydrogen; C$_{1-6}$alkyl; C$_{1-6}$alkyl-O—C$_{1-6}$alkyl-; C$_{1-6}$alkyl-S—C$_{1-6}$alkyl-; C$_{2-8}$alkenyl; C$_{1-6}$alkyl-C(=O)— or C$_{2-6}$alkenyl-C(=O)—; wherein at least one of R$^5$ or R$^6$ is selected from C$_{1-6}$alkyl; C$_{1-6}$alkyl-O—C$_{1-6}$alkyl-; C$_{1-6}$alkyl-S—C$_{1-6}$alkyl-; C$_{2-8}$alkenyl; C$_{1-6}$alkyl-C(=O)— or C$_{2-8}$alkenyl-C(=O)—, and wherein each of said C$_{1-6}$alkyl; C$_{1-4}$alkyl-O—C$_{1-6}$alkyl-; C$_{1-6}$alkyl-S—C$_{1-6}$alkyl-; C$_{2-6}$alkenyl; C$_{1-6}$alkyl-C(=O)— or C$_{2-8}$alkenyl-C(=O)— is substituted with 1, 2, or 3 substituents each independently selected from the group consisting of aryl, heteroaryl, C$_{3-6}$cycloalkenyl, —C(=O)—OR$^{21}$; —C(=O)—SR$^{22}$; Het$^1$; —O-Het$^2$; and —S-Het$^3$;

R$^7$ or R$^8$ are independently selected from the group consisting of hydrogen; or C$_{1-6}$alkyl substituted with 1, 2, or 3 substituents each independently selected from the group consisting of aryl, heteroaryl, C$_{3-6}$cycloalkenyl, —C(=O)—OR$^{21}$; and —C(=O)—NH$_2$;

R$^9$ or R$^{10}$ are independently selected from the group consisting of hydrogen; or C$_{1-6}$alkyl substituted with 1, 2, or 3 substituents each independently selected from the group consisting of aryl, heteroaryl, C$_{3-6}$cycloalkenyl, —C(=O)—OR$^{21}$; and —C(=O)—NH$_2$;

R$^{13}$ or R$^{14}$ are independently selected from the group consisting of hydrogen; C$_{1-6}$alkyl; C$_{1-6}$alkyl; C$_{1-6}$alkyl-O—C$_{1-6}$alkyl-; C$_{1-6}$alkyl-S—C$_{1-6}$alkyl-; or C$_{1-6}$alkyl-C(=O)— and wherein each of said C$_{1-6}$alkyl; C$_{1-6}$alkyl-O—C$_{1-6}$alkyl-; C$_{1-6}$alkyl-S—C$_{1-4}$alkyl-; or C$_{1-6}$alkyl-C(=O)— is substituted with 1, 2, or 3 substituents each independently selected from the group consisting of —C(=O)—OR$^{21}$; —C(=O)—SR$^{22}$; Het$^1$; —O-Het$^2$; and —S-Het$^3$;

R$^{21}$ is selected from the group consisting of C$_{1-20}$alkyl; C$_{1-20}$alkenyl; C$_{1-20}$alkynyl; optionally substituted C$_{3-15}$cycloalkyl; optionally substituted aryl; optionally substituted heterocyclyl; and optionally substituted heteroaryl;

wherein said C$_{1-20}$alkyl is optionally substituted with 1, 2, 3 or more substituents each independently selected from the group consisting of halo, cyano, hydroxy, aryl-O—, aryl-S—, aryl-S(=O)$_2$—, aryl-C(=O), —C(=O)—NR$^{13}$R$^{14}$, C$_{3-10}$cycloalkyl, —O—C(=O)—C$_{1-6}$alkyl, C$_{1-6}$alkyl-O—, C$_{1-6}$alkyl-S—, aryl, heteroaryl, heterocyclyl or from the formula:

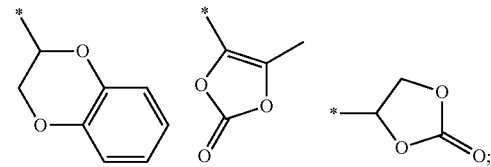

or

R$^{21}$ taken together with the oxycarbonyl and 'aryl or heteroaryl' to which it is attached forms a cyclic ester comprising from 4 to 9 carbon atoms in the cyclic ester ring;

R$^{22}$ is C$_{1-20}$alkyl optionally substituted with 1, 2, 3 or more substituents each independently selected from the group consisting of halo, hydroxy, amino, cyano, and mono- or di-(C$_{1-4}$alkyl)amino;

Het$^1$, Het$^2$ or Het$^3$ are independently selected from the group comprising;

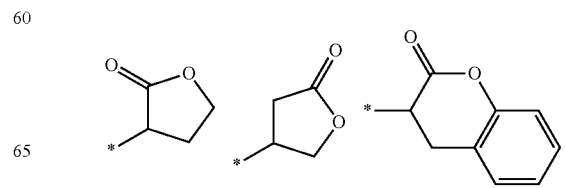

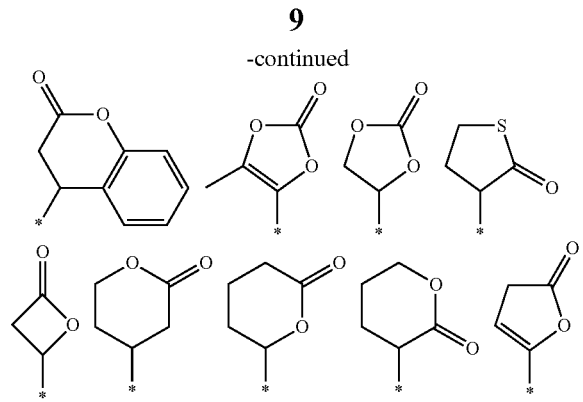

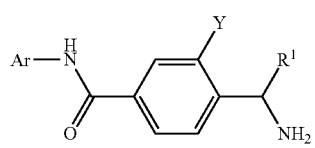

wherein Y, $R^1$ and Ar are as defined hereinbefore, including the stereo-isomeric forms, solvates, and pharmaceutically acceptable addition salts thereof.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, acyl, alkylamino, alkoxy, thiol, alkylthio, carboxylic acid, acylamino, alkyl esters, carbamate, thioamido, urea, sulfonamido and the like.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, E- and Z-propynyl, isopropynyl, E- and Z-butynyl, E- and Z-isobutynyl, E- and Z-pentynyl, E, Z-hexynyl, and the like. An optionally substituted alkynyl refers to an alkynyl having optionally one or more substituents (for example 1, 2, 3 or 4), selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structure.

Viewed from a further aspect, the invention provides the use of a compound of the invention, or a composition comprising such a compound, for inhibiting the activity of at least one kinase, in vitro or in vivo.

Viewed from a further aspect, the invention provides the use of a compound of the invention, or a composition comprising such a compound, for inhibiting the activity of at least one ROCK kinase, for example ROCKII and/or ROCKI isoforms.

Viewed from a further aspect, the invention provides a pharmaceutical and/or veterinary composition comprising a compound of the invention.

Viewed from a still further aspect, the invention provides a compound of the invention for use in human or veterinary medicine.

Viewed from a still further aspect, the invention provides the use of a compound of the invention in the preparation of a medicament for the prevention and/or treatment of at least one disease and/or disorder selected from the group comprising eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupuserythematosus, spasm, hypertension, chronic obstructive bladder disease, premature birth, infection, allergy, obesity, pancreatic disease and AIDS.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Undefined (racemic) asymmetric centers that may be present in the compounds of the present invention are interchangeably indicated by drawing a wavy bonds or a straight bond in order to visualize the undefined steric character of the bond.

As already mentioned hereinbefore, in a first aspect the present invention provides compounds of Formula I Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more Spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2CH_2$ $CH_2$—*, *—$CH$(—$CH_2CH_3$)—*, or *—$CH_2CH$ (—$CH_3$)—*. Likewise a $C_3$ cycloalkylene group may be

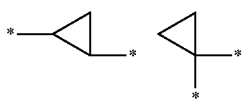

Where a cycloalkylene group is present, this is preferably a $C_3$-$C_6$ cycloalkylene group, more preferably a $C_3$ cycloalkylene (i.e. cyclopropylene group) wherein its connectivity to the structure of which it forms part is through a common carbon atom. Cycloalkylene and alkylene biradicals in compounds of the invention may be, but preferably are not, substituted.

The terms "heterocycly" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituents (for example 1 to 4 substituents, or for example 1, 2, 3 or 4), selected from those defined for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyt, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrahydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphthylenyl, 3-, 4-, or 5-acenaphthenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —$SO_2R^a$, alkylthio, carboxyl, and the like, wherein $R^a$ is alkyl or cycloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

The term "pyrrolyl" (also called azolyl) as used herein includes pyrrol-1-yl, pyrrol-2-yl and pyrrol-3-yl.

The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl).

The term "pyrazolyl" (also called 1H-pyrazolyl and 1,2-diazolyl) as used herein includes pyrazol-1-yl, pyrazol-3-yl, pyrazol-4-yl and pyrazol-5-yl.

The term "imidazolyl" as used herein includes imidazol-1-yl, imidazol-2-yl, imidazol-4-yl and imidazol-5-yl.

The term "oxazolyl" (also called 1,3-oxazolyl) as used herein includes oxazol-2-yl; oxazol-4-yl and oxazol-5-yl.

The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl).

The term "isothiazolyl" (also called 1,2-thiazolyl) as used herein includes isothiazol-3-yl, isothiazol-4-yl, and isothiazol-5-yl.

The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl.

The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl.

The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

The term "tetrazoly" as used herein includes 1H-tetrazol-1-yl, 1H-tetrazol-5-yl, 2H-tetrazol-2-yl, and 2H-tetrazol-5-yl.

The term "oxatriazolyl" as used herein includes 1,2,3,4-oxatriazol-5-yl and 1,2,3,5-oxatriazol-4-yl.

The term "thiatriazoly" as used herein includes 1,2,3,4-thiatriazol-5-yl and 1,2,3,5-thiatriazol-4-yl.

The term "pyridinyl" (also called "pyridyl") as used herein includes pyridin-2-yl, pyridin-3-yl and pyridin-4-yl (also called 2-pyridyl, 3-pyridyl and 4-pyridyl).

The term "pyrimidyl" as used herein includes pyrimid-2-yl, pyrimid-4-yl, pyrimid-5-yl and pyrimid-6-yl.

The term "pyrazinyl" as used herein includes pyrazin-2-yl and pyrazin-3-yl. The term "pyridazinyl as used herein includes pyridazin-3-yl and pyridazin-4-yl.

The term "oxazinyl" (also called "1,4-oxazinyl") as used herein includes 1,4-oxazin-4-yl and 1,4-oxazin-5-yl.

The term "dioxinyl" (also called "1,4-dioxinyl") as used herein includes 1,4-dioxin-2-yl and 1,4-dioxin-3-yl.

The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl.

The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

The term "imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl.

The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl.

The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl.

The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

The term "thieno[2,3-d]imidazolyl" as used herein includes thieno[2,3-d]imidazol-2-yl, thieno[2,3-d]imidazol-4-yl and thieno[2,3-d]imidazol-5-yl.

The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl.

The term "indolyl" as used herein includes indol-1-yl, indol-2-yl, indol-3-yl, -indol-4-yl, indol-5-yl, indol-6-yl and indol-7-yl.

The term "indolizinyl" as used herein includes indolizin-1-yl, indolizin-2-yl, indolizin-3-yl, indolizin-5-yl, indolizin-6-yl, indolizin-7-yl, and indolizin-8-yl.

The term "isoindolyl" as used herein includes isoindol-1-yl, isoindol-2-yl, isoindol-3-yl, isoindol-4-yl, isoindol-5-yl, isoindol-6-yl and isoindol-7-yl.

The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl.

The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl.

The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl).

The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl.

The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl.

The term "benzimidazolyl" as used herein includes benzimidazol-1-yl, benzimidazol-2-yl, benzimidazol-4-yl, benzimidazol-5-yl, benzimidazol-6-yl and benzimidazol-7-yl.

The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

The term "benzotriazolyl" as used herein includes benzotriazol-1-yl, benzotriazol4-yl, benzotriazol-5-yl, benzotriazol-6-yl and benzotriazol-7-yl.

The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

The term "thienopyridinyl" as used herein includes thieno[2,3-b]pyridinyl, thieno[2,3-c]pyridinyl, thieno[3,2-c]pyridinyl and thieno[3,2-b]pyridinyl.

The term "purinyl" as used herein includes purin-2-yl, purin-6-yl, purin-7-yl and purin-8-yl.

The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl.

The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl.

The term "quinolinyl" as used herein includes quinolin-2-yl, quinolin-3-yl, quinolin-4-yl, quinolin-5-yl, quinolin-6-yl, quinolin-7-yl and quinolin-8-yl.

The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

The term "cinnolinyl" as used herein includes cinnolin-3-yl, cinnolin-4-yl, cinnolin-5-yl, cinnolin-6-yl, cinnolin-7-yl and cinnolin-8-yl.

The term "quinazolinyl" as used herein includes quinazolin-2-yl, quiriazolin-4-yl, quinazolin-5-yl, quinazolin-6-yl, quinazolin-7-yl and quinazolin-8-yl.

The term "quinoxalinyl" as used herein includes quinoxalin-2-yl, quinoxalin-5-yl, and quinoxalin-6-yl.

The term "7-azaindolyl" as used herein refers to 1H-Pyrrolo[2,3-b]pyridinyl and includes 7-azaindol-1-yl, 7-azaindol-2-yl, 7-azaindol-3-yl, 7-azaindol-4-yl, 7-azaindol-5-yl, 7-azaindol-6-yl.

The term "6-azaindolyl" as used herein refers to 1H-Pyrrolo[2,3-c]pyridinyl and includes 6-azaindol-1-yl, 6-azaindol-2-yl, 6-azaindol-3-yl, 6-azaindol-4-yl, 6-azaindol-5-yl, 6-azaindol-7-yl.

The term "5-azaindoly" as used herein refers to 1H-Pyrrolo[3,2-c]pyridinyl and includes 5-azaindol-1-yl, 5-azaindol-2-yl, 5-azaindol-3-yl, 5-azaindol-4-yl, 5-azaindol-6-yl, 5-azaindol-7-yl.

The term "4-azaindolyl" as used herein refers to 1H-Pyrrolo[3,2-b]pyridinyl and includes 4-azaindol-1-yl, 4-azaindol-2-yl, 4-azaindol-3-yl, 4-azaindol-5-yl, 4-azaindol-6-yl, 4-azaindol-7-yl.

For example, non-limiting examples of heteroaryl can be 2- or 3-furyl, 2- or 3-thienyl, 1-, 2- or 3-pyrrolyl, 1-, 2-, 4- or 5-imidazolyl, 1-, 3-, 4- or 5-pyrazolyl, 3-, 4- or 5-isoxazolyl, 2-, 4- or 5-oxazolyl, 3-, 4- or 5-isothiazolyl, 2-, 4- or 5-thiazolyl, 1,2,3-triazol-1-, -4- or -5-yl, 1,2,4-triazol-1-, -3-, -4- or -5-yl, 1H-tetrazol-1-, or 5-yl, 2H-tetrazol-2-, or -5-yl, 1,2,3-oxadiazol-4- or -5-yl, 1,2,4-oxadiazol-3- or -5-yl, 1,2,5-oxadiazolyl, 1,3,4-oxadiazolyl, 1,2,3-thiadiazol-4- or -5-yl, 1,2,4-thiadiazol-3- or -5-yl, 1,2,5-thiadiazol-3- or -4-yl, 1,3,4-thiadiazolyl, 1- or 5-tetrazolyl, 2-, 3- or 4-pyridyl, 3- or 4-pyridazinyl, 2-, 4-, 5- or 6-pyrimidyl, 2-, 3-, 4-, 5- 6-2H-thiopyranyl, 2-, 3- or 4-4H-thiopyranyl, 4-azaindol-1-, 2-, 3-, 5-, or 7-yl, 5-azaindol-1-, or 2-, 3-, 4-, 6-, or 7-yl, 6-azaindol-1, 2-, 3-, 4-, 5-, or 7-yl, 7-azaindol-1-, 2-, 3-, 4, 5-, or 6-yl, 2-, 3-, 4-, 5-, 6- or 7-benzofuryl, 1-, 3-, 4- or 5-isobenzofuryl, 2-, 3-, 4-, 5-, 6- or 7-benzothienyl, 1-, 3-, 4- or 5-isobenzothienyl, 1-, 2-, 3-, 4-, 5-, 6- or 7-indolyl, 2- or 3-pyrazinyl, 1,4-oxazin-2- or -3-yl, 1,4-dioxin-2- or -3-yl, 1,4-thiazin-2- or -3-yl, 1,2,3-triazinyl, 1,2,4-triazinyl, 1,3,5-triazin-2-, -4- or -6-yl, thieno[2,3-b]furan-2-, -3-, -4-, or -5-yl, benzimidazol-1-yl, -2-yl, -4-yl, -5-yl, -6-yl, or -7-yl, 1-, 3-, 4-, 5-, 6- or 7-benzopyrazolyl, 3-, 4-, 5-, 6- or 7-benzisoxazolyl, 2-, 4-, 5-, 6- or 7-benzoxazolyl, 3-, 4-, 5-, 6- or 7-benzisothiazolyl, 1,3-benzothiazol-2-yl, -4-yl, -5-yl, -6-yl or -7-yl, 1,3-benzodioxol-4-yl, -5-yl, -6-yl, or -7-yl, benzotriazol-1-yl, -4-yl, -5-yl, -6-yl or -yl1-, 2-thianthrenyl, 3-, 4- or 5-isobenzofuranyl, 1-, 2-, 3-, 4- or 9-xanthenyl, 1-, 2-, 3- or 4-phenoxathiinyl, 2-, 3-pyrazinyl, 1-, 2-, 3-, 4-, 5-, 6-, 7- or 8-indolizinyl, 2-, 3-, 4- or 5-isoindolyl, 1H-indazol-1-yl, 3-yl, -4-yl, -5-yl, -6-yl, or -7-yl, 2H-indazol-2-yl, 3-yl, -4-yl, -5-yl, -6-yl, or -7-yl, imidazo[2,1-b][1,3]thiazol-2-yl, imidazo[2,1-b][1,3]thiazol-3-yl, imidazo[2,1-b][1,3]thiazol-5-yl or imidazo[2,1-b][1,3]thiazol-6-yl, imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl or imidazo[1,2-a]pyridin-7-yl, tetrazolo[1,5-a]pyridine-5-yl, tetrazolo[1,5-a]pyridine-6-yl, tetrazolo[1,5-a]pyridine-7-yl, or tetrazolo[1,5- a]pyridine-8-yl, 2-, 6-, 7- or 8-purinyl, 4-, 5- or 6-phthalazinyl, 2-, 3- or 4-naphthyridinyl, 2-, 5- or 6-quinoxalinyl, 2-, 4-, 5-, 6-, 7- or 8-quinazolinyl, 1-, 2-, 3- or 4-quinolizinyl, 2-, 3-, 4-, 5-, 6-, 7-, or 8-quinolinyl(quinolyl), 2-, 4-, 5-, 6-, 7- or 8-quinazolyl, 1-, 3-, 4-, 5-, 6-, 7- or 8-isoquinolinyl(isoquinolyl), 3-, 4-, 5-, 6-, 7- or 8-cinnolinyl, 2-, 4-, 6- or 7-pteridinyl, 1-, 2-, 3-, 4- or 9-carbazolyl, 1-, 2-, 3-, 4-, 5-, 6-, 7-, 8- or 9-carbolinyl, 1-, 2-, 3-, 4-, 5-, 6-, 7-, 8-, 9- or 10-phenanthridinyl, 1-, 2-, 3- or 4-acridinyl, 1-, 2-, 3-, 4-, 5-, 6-, 7-, 8- or 9-perimidinyl, 2-, 3-, 4-, 5-, 6-, 7-, 8-, 9- or 10-(1,7)phenanthrolinyl, 1- or 2-phenazinyl, 1-, 2-, 3-, 4-, or 10-phenothiazinyl, 3- or 4-furazanyl, 1-, 2-, 3-, 4-, or 10-phenoxazinyl, or additionally substituted derivatives thereof.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —OR$^b$ wherein R$^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclyl-alkyl" by itself or as part of another substituents refers to a group having one of the aforementioned heterocyclyl group attached to one of the aforementioned alkyl group, i.e., to a group —R$^d$-R$^c$ wherein R$^d$ is alkylene or alkylene substituted by alkyl group and R$^c$ is a heterocyclyl group.

The term "carboxy" or "carboxyl" or "hydroxycarbonyl" by itself or as part of another substituent refers to the group —CO$_2$H. Thus, a carboxyalkyl is an alkyl group as defined above having at least one substituent that is —CO$_2$H.

The term "alkoxycarbonyl" by itself or as part of another substituent refers to a carboxy group linked to an alkyl radical i.e. to form —C(=O)OR$^e$, wherein R$^e$ is as defined above for alkyl.

The term "alkylcarbonyloxy" by itself or as part of another substituent refers to a —O—C(=O)R$^e$ wherein R$^e$ is as defined above for alkyl.

The term "alkylcarbonylamino" by itself or as part of another substituent refers to an group of Formula —NH(C=O)R or —NR'(C=O)R, wherein R and R$^1$ are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above.

The term "haloalkoxy" alone or in combination refers to a group of Formula —O-alkyl wherein the alkyl group is substituted by 1, 2, or 3 halogen atoms. For example, "haloalkoxy" includes —OCF$_3$, —OCHF$_2$, —OCH$_2$F, —O—CF$_2$—CF$_3$, —O—CH$_2$—CF$_3$, —O—CH$_2$—CHF$_2$, and —O—CH$_2$—CH$_2$F.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted with once or more, and preferably once, twice or thrice. Substituents may be selected from, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to the compounds as depicted in Tables 1 to 11, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a further embodiment, the present invention provides compounds of formula I wherein;

$R^1$ is hydrogen, or $C_{1-4}$alkyl; in particular methyl;

Ar is as defined hereinbefore, and

Y is an aryl or heteroaryl substituted with a substituent selected from the group consisting of —C(=O)—OR$^{21}$; —C(=O)—SR$^{22}$; —C(=O)—NR$^3$R$^4$; —NR$^5$R$^6$; —O—C$_{1-6}$alkyl; —C$_{1-6}$alkyl; or —C$_{2-8}$alkenyl;
  wherein said —O—C$_{1-6}$alkyl, —C$_{1-6}$alkyl, or —C$_{2-8}$alkenyl are each independently substituted with a substituent selected from the group consisting of C(=O)—OR$^{21}$; —C(=O)—S$^{22}$; —C(=O)—NR$^3$R$^4$; Het$^1$; —O-Het$^2$; and —S-Het$^3$;

R$^3$ is selected from the group consisting of hydrogen; C$_{1-20}$alkyl optionally substituted with 1, 2 or 3 substituents each independently selected from the group consisting of —C(=O)—OR$^{21}$; —C(=O)—SR$^{22}$; —C(=O)—NR$^7$R$^8$; Het$^1$; —O-Het$^2$; —S-Het$^3$; C$_{1-6}$alkyl-S— and C$_{1-6}$alkyl-O—; in particular R$^3$ is hydrogen;

R$^4$ is selected from the group consisting of C$_{1-20}$alkyl substituted with 1, 2 or 3 substituents each independently selected from the group consisting of —C(=O)—OR$^{21}$; —C(=O)—SR$^{22}$; —C(=O)—NR$^7$R$^8$; Het$^1$; —O-Het$^2$; —S-Het$^3$; C$_{1-6}$alkyl-S— and C$_{1-6}$alkyl-O—; in particular R$^4$ is selected from the group consisting of C$_{1-20}$alkyl substituted with 1, 2 or 3 substituents each independently selected from the group consisting of —C(=O)—OR$^{21}$; —C(=O)—SR$^{22}$; —C(=O)—NR$^7$R$^8$; Het$^1$; —O-Het$^2$; and —S-Het$^3$; or R$^3$ and R$^4$ together with the nitrogen atom to which they are attached form a heterocycle substituted with one substituent selected from the group consisting of —C(=O)—OR$^{21}$; —C(=O)—SR$^{22}$; —C(=O)—NR$^9$R$^{10}$; Het$^1$; —O-Het$^2$; —S-Het$^3$; or C$_{1-6}$alkyl wherein said C$_{1-6}$alkyl is substituted with 1, 2 or 3 substituents each independently selected from the group consisting of —C(=O)—OR$^{21}$; —C(=O)—SR$^{22}$; —C(=O)—NR$^9$R$^{10}$; Het$^1$; —O-Het$^2$; and —S-Het$^3$; in particular R$^3$ and R$^4$ together with the nitrogen atom to which they are attached form a heterocycle substituted with one substituent selected from the group consisting of —C(=O)—OR$^{21}$; —C(=O)—SR$^{22}$; —C(=O)—NR$^9$R$^{10}$; Het$^1$; or C$_{1-6}$alkyl wherein said C$_{1-6}$alkyl is substituted with 1, 2, or 3 substituents each independently selected from the group consisting of —C(=O)—OR$^{21}$; —C(=O)—NR$^9$R$^{10}$; Het$^1$; —O-Het$^2$; and —S-Het$^3$; more in particular R$^3$ and R$^4$ together with the nitrogen atom to which they are attached form a heterocycle substituted with one substituent selected from the group consisting of —C(=O)—OR$^{21}$; —C(=O)—SR$^{22}$; —C(=O)—NR$^9$R$^{10}$; Het$^1$; —O-Het$^2$; and —S-Het$^3$;

R$^5$ or R$^6$ are independently selected from the group consisting of hydrogen; C$_{1-6}$alkyl; C$_{1-6}$alkyl-O—C$_{1-6}$alkyl-; C$_{1-6}$alkyl-S—C$_{1-6}$alkyl-; C$_{2-8}$alkenyl; C$_{1-6}$alkyl-C(=O)— or C$_{2-8}$alkenyl-C(=O)—; wherein at least one of R$^5$ or R$^6$ is selected from C$_{1-6}$alkyl; C$_{1-6}$alkyl-S—C$_{1-6}$alkyl-; or C$_{1-6}$alkyl-C(=O)—, and wherein each of said C$_{1-6}$alkyl; C$_{1-6}$alkyl-O—C$_{1-6}$alkyl-; C$_{1-6}$alkyl-S—C$_{1-6}$alkyl-; or C$_{1-6}$alkyl-C(=O)— is substituted with 1, 2, or 3 substituents each independently selected from the group consisting of —C(=O)—OR$^{21}$; —C(=O)—SR$^{22}$; Het$^1$; —O-Het$^2$; and —S-Het$^3$; in particular R$^5$ or R$^6$ are independently selected from the group consisting of hydrogen; C$_{1-6}$alkyl; C$_{1-6}$alkyl-S—C$_{1-6}$alkyl-; or C$_{1-6}$alkyl-C(=O)—; wherein at least one of R$^5$ or R$^6$ is selected from C$_{1-6}$alkyl; C$_{1-6}$alkyl-S—C$_{1-6}$alkyl-; or C$_{1-6}$alkyl-C(=O)—, and wherein each of said C$_{1-6}$alkyl; C$_{1-6}$alkyl-S—C$_{1-6}$alkyl-; or C$_{1-6}$alkyl-C(=O)— is substituted with 1, 2, or 3 substituents each independently selected from the group consisting of —C(=O)—OR$^{21}$; -Het$^1$; —O-Het$^2$; and —S-Het$^3$; more in particular R$^5$ or R$^6$ are independently selected from the group consisting of hydrogen; C$_{1-6}$alkyl; or C$_{1-6}$alkyl-C(=O)—; wherein at least one of R$^5$ or R$^6$ is selected from C$_{1-6}$alkyl; or C$_{1-6}$alkyl-C(=O)—, and wherein each of said C$_{1-6}$alkyl; or C$_{1-6}$alkyl-C(=O)— is substituted with 1, 2, or 3 substituents each independently selected from the group consisting of —C(=O)—OR$^{21}$; -Het$^1$; —O-Het$^2$; and —S-Het$^3$; even more in particular R$^5$ or R$^6$ are independently selected from the group consisting of hydrogen; or C$_{1-6}$alkyl; wherein at least one of R$^5$ or R$^6$ is C$_{1-6}$alkyl substituted with 1, 2, or 3 substituents each independently selected from the group consisting of -Het$^1$; —O-Het$^2$; and —S-Het$^3$;

R$^7$ or R$^8$ are independently selected from the group consisting of hydrogen; or C$_{1-6}$alkyl substituted with 1, 2, or 3 substituents each independently selected from the group consisting of aryl, heteroaryl, C$_{3-6}$cycloalkenyl, —C(=O)—OR$^{21}$; and —C(=O)—NH$_2$; in particular R$^7$ or R$^8$ are independently selected from the group consisting of hydrogen; or C$_{1-6}$alkyl substituted with 1, 2, or 3 substituents each independently selected from the group consisting of —C(=O)—OR$^{21}$; and —C(=O)—NH$_2$; more in particular R$^7$ or R$^8$ are independently selected from the group consisting of hydrogen; or C$_{1-6}$alkyl substituted with —C(=O)—OR$^{21}$;

R$^9$ or R$^{10}$ are independently selected from the group consisting of hydrogen; or C$_{1-6}$alkyl substituted with 1, 2, or 3, —C(=O)—OR$^{21}$ substituents;

R$^{13}$ or R$^{14}$ are independently selected from the group consisting of hydrogen; C$_{1-6}$alkyl; C$_{1-6}$alkyl; C$_{1-6}$alkyl-O—C$_{1-6}$alkyl-; C$_{1-6}$alkyl-S—C$_{1-6}$alkyl-; or C$_{1-6}$alkyl-C(=O)— and wherein each of said C$_{1-6}$alkyl; C$_{1-6}$alkyl-S—C$_{1-6}$alkyl-; or C$_{1-6}$alkyl-C(=O)— is substituted with 1, 2, or 3 substituents each independently selected from the group consisting of —C(=O)—OR$^{21}$; —C(=O)—SR$^{22}$; Het$^1$; —O-Het$^2$; and —S-Het$^3$; in particular R$^{13}$ and R$^{14}$ represent hydrogen;

R$^{21}$ is selected from the group consisting of C$_{1-20}$alkyl; C$_{1-20}$alkenyl; optionally substituted C$_{3-15}$cycloalkyl; optionally substituted heterocyclyl; and optionally substituted aryl;
  wherein said C$_{1-20}$alkyl is optionally substituted with 1, 2, 3 or more substituents selected from the group consisting of halo, cyano, hydroxy, aryl-O—, aryl-S—, aryl-S(=O)$_2$—, aryl-C(=O), —C(=O)—NR$^{13}$R$^{14}$, —O—C(=O)—C$_{1-6}$alkyl, C$_{1-6}$alkyl-O—, C$_{1-6}$alkyl-S—, aryl, heteroaryl, heterocyclyl and C$_{3-15}$cycloalkyl or from the formula:

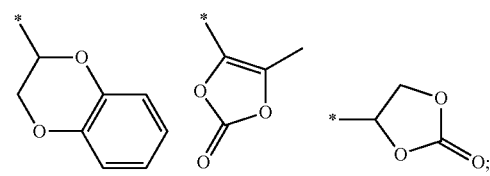

or

R$^{21}$ taken together with the oxycarbonyl and phenyl to which it is attached forms a cyclic ester consisting of

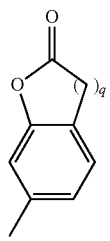

wherein q is an integer from 1 to 6;

$R^{22}$ is $C_{1-20}$alkyl optionally substituted with 1, 2, 3 or more halo substituents;

$Het^1$, $Het^2$ or $Het^3$ are independently selected from the group comprising;

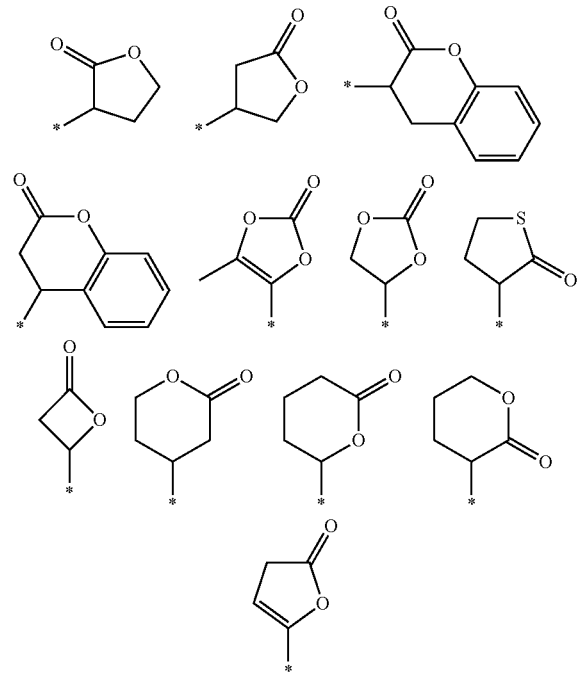

Another group of interesting compounds according to the present invention are those compounds of formula (I) wherein one or more of the following restrictions apply;

Ar represents pyridinyl, optionally substituted with halo; in particular Ar represents pyridinyl substituted with fluoro; in an even further embodiment Ar represents pyridinyl substituted with fluoro; in an even further embodiment Ar represents

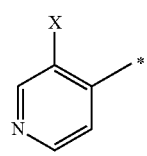

wherein X is hydrogen or halo; in particular X is hydrogen or fluoro; more in particular X is fluoro;

$R^1$ represents hydrogen or $C_{1-4}$alkyl; in particular $C_{1-4}$alkyl; more in particular methyl;

Y is an aryl or heteroaryl substituted with a substituent selected from the group consisting of —C(=O)—NR$^3$R$^4$; —NR$^5$R$^6$; —O—C$_{1-6}$alkyl; or —C$_{1-6}$alkyl;

wherein said —O—C$_{1-6}$ alkyl or —C$_{1-6}$alkyl are each independently substituted with a substituent selected from the group consisting of —C(=O)—NR$^3$R$^4$, —O-Het$^2$ and S-Het$^3$; with in a particular embodiment said Het$^2$ or Het$^3$ independently being selected from the group comprising

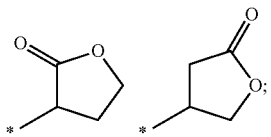

Y is an aryl or heteroaryl substituted with a substituent selected from the group consisting of —C(=O)—OR$^{21}$; —C(=O)—SR$^{22}$; —C(=O)—NR$^3$R$^4$; —O—C$_{1-6}$alkyl; or —C$_{1-6}$alkyl;

wherein said —O—C$_{1-6}$alkyl or —C$_{1-6}$alkyl are each independently substituted with a substituent selected from the group consisting of —C(=O)—OR$^{21}$, and Het$^1$; with in a particular embodiment said;

$R^{21}$ being selected from —C$_{1-6}$alkyl or aryl; more in particular said $R^{21}$ being selected from —C$_{1-6}$alkyl or phenyl; and said Het$^1$ being selected from the group comprising

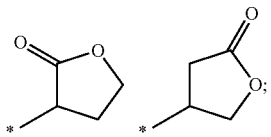

$R^3$ is hydrogen;

$R^4$ is —C$_{1-6}$alkyl substituted with a substituent selected from —O-Het$^2$ or —S-Het$^3$-;

$R^4$ is —C$_{1-6}$alkyl substituted with a substituent selected from —C(=O)—OR$^{21}$, —C(=O)—SR$^{22}$, or Het$^1$; with in a particular embodiment said $R^{21}$ being a —C$_{1-6}$alkyl substituted with a substituent selected from —C(=O)—OR$^{21}$, or Het$^1$; with in a more particular embodiment said $R^{21}$ being a —C$_{1-6}$alkyl;

$R^5$ or $R^6$ are independently selected from the group consisting of hydrogen; C$_{1-6}$alkyl; or C$_{1-6}$alkyl-S—C$_{1-6}$alkyl-; wherein at least one of $R^5$ or $R^6$ is selected from the group consisting of C$_{1-6}$alkyl; or C$_{1-6}$alkyl-S—C$_{1-6}$alkyl-; and wherein each of said C$_{1-6}$alkyl; or C$_{1-6}$alkyl-S—C$_{1-6}$alkyl-; is substituted with a substituent selected from the group consisting of —C(=O)—OR$^{21}$, Het$^1$ and —S-Het$^3$; with in a particular embodiment said;

$R^{21}$ being selected from —C$_{1-6}$alkyl or aryl; more in particular said $R^{21}$ being a —C$_{1-6}$alkyl; and said Het$^1$ or Het$^3$ independently being selected from the group comprising

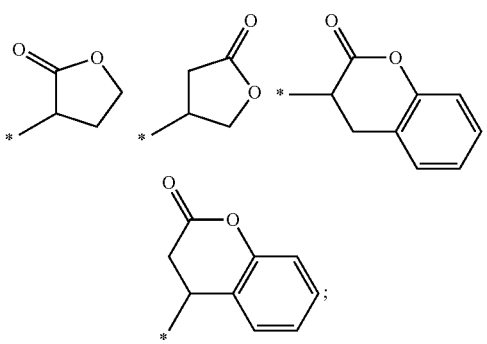

$R^{21}$ is selected from —$C_{1-6}$alkyl, aryl or optionally substituted heteroaryl; more in particular said $R^{21}$ being selected from —$C_{1-6}$alkyl, 3,4-dihydro-1(2H)-benzopyranyl, 3,4-dihydro-1(2H)-benzopyranyl, or phenyl, wherein said 3,4-dihydro-1(2H)-benzopyranyl, 3,4-dihydro-1(2H)-benzopyranyl, is substituted with oxo;

Aryl represents phenyl;

Heteroaryl represents 3,4-dihydro-1(2H)-benzopyranyl, 3,4-dihydro-1(2H)-benzopyranyl, or indolyl; in particular indolyl;

Y is an aryl or heteroaryl substituted with a substituent selected from the group consisting of —C(=O)—$OR^{21}$; —C(=O)—$SR^{22}$; —C(=O)—$NR^3R^4$; —O—$C_{1-6}$alkyl; or —$C_{1-6}$alkyl;

wherein said —O—$C_{1-6}$alkyl or —$C_{1-6}$alkyl are each independently substituted with a substituent selected from the group consisting of —C(=O)—$OR^{21}$, and $Het^1$; with in a particular embodiment said;

$R^{21}$ being selected from —$C_{1-6}$alkyl or aryl; more in particular said $R^{21}$ being selected from —$C_{1-6}$alkyl or phenyl;

said $Het^1$ being selected from the group comprising

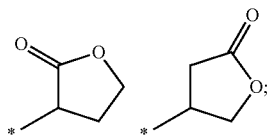

and wherein said —C(=O)—$OR^{21}$; —C(=O)—$SR^{22}$; —C(=O)—$NR^3R^4$; —O—$C_{1-6}$alkyl; or —$C_{1-6}$alkyl are at the meta or para position vis-à-vis the binding of the aryl or heteroaryl to the remainder of the molecule such as represented in in formulae IIa-XXIIIa, and IIb-XXIIIb below.

In a particular embodiment, the present invention provides compounds of formula I, wherein the Y substituent in its definitions, i.e. as a substituent or as part of a substituent comprises at least one group selected from C(=O)—$OR^{21}$; —C(=O)—$SR^{22}$; $Het^1$; —O-$Het^2$; and —S-$Het^3$. In a more particular embodiment, the present invention provides the compounds of formula I, wherein the further substituents to the Y substituent are at the meta or para position vis-à-vis the binding of said aryl or heteroaryl to the remainder of the molecule and/or as represented in formulae IIa-XXIIIa, and IIb-XXIIIb below.

In an even further embodiment, the present invention provides compounds of formula I, as defined in any one of the different embodiments described herein, with the proviso that when Y represents an aryl or heteroaryl substituted with a substituent selected from the —C(=O)—$OR^{21}$; or —C(=O)—$SR^{22}$; and wherein said $R^{21}$ or $R^{22}$ represents an unsubstituted $C_{1-20}$alkyl; said —C(=O)—$OR^{21}$; or —C(=O)—$SR^{22}$; is at the meta or para position vis-à-vis the binding of said aryl or heteroaryl to the remainder of the molecule and as represented in formulae IIa, IIb, IIIa and IIIb below.

In a further embodiment, the present invention provides compounds of formula I, wherein one or more of the following restrictions apply;

Y is 2-oxo-2,3-dihydrobenzofuranyl or Y is a phenyl, indolyl or thiophenyl, said phenyl indolyl and thiophenyl being substituted with a substituent selected from the group consisting of —C(=O)—$OR^{21}$; —C(=O)—$SR^{22}$; —C(=O)—$NR^3R^4$; —$NR^5R^6$; —O—$C_{1-6}$alkyl; —$C_{1-6}$alkyl; or —$C_{2-8}$alkenyl wherein said —O—$C_{1-6}$alkyl or —$C_{2-8}$alkenyl is substituted with a substituent selected from the group consisting of C(=O)—$OR^{21}$; —C(=O)—$SR^{22}$; —C(=O)—$NR^3R^4$; $Het^1$; —O-$Het^2$; and —S-$Het^3$;

$R^5$ or $R^6$ are independently selected from the group consisting of hydrogen; $C_{1-6}$alkyl; or $C_{1-6}$alkyl-S—$C_{1-6}$alkyl-; wherein at least one of $R^5$ or $R^6$ is selected from the group consisting of $C_{1-6}$alkyl; or $C_{1-6}$alkyl-S—$C_{1-6}$alkyl-; and wherein each of said $C_{1-6}$alkyl; or $C_{1-6}$alkyl-S—$C_{1-6}$alkyl-; is substituted with a substituent selected from the group consisting of —C(=O)—$OR^{21}$, $Het^1$ and —S-$Het^3$;

$R^{21}$ is selected from the group consisting of $C_{1-20}$alkyl; optionally substituted $C_{3-10}$cycloalkyl; optionally substituted aryl; and optionally substituted heterocyclyl; wherein said $C_{1-20}$alkyl is optionally substituted with a substituent selected from the group consisting of halo, cyano, hydroxy, —C(=O)—$NR^{13}R^{14}$, —O—C(=O)—$C_{1-6}$alkyl, $C_{1-6}$alkyl-O—, $C_{1-6}$alkyl-S—, aryl, heteroaryl, heterocyclyl, and $C_{3-10}$cycloalkyl, or from the formula:

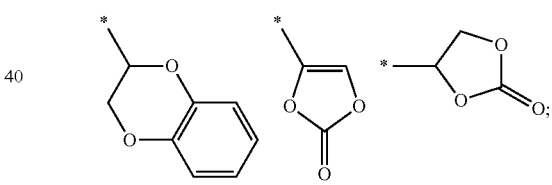

in particular $R^{21}$ is selected from the group consisting of $C_{1-20}$alkyl; optionally substituted $C_{3-10}$cycloalkyl; optionally substituted aryl; and optionally substituted heterocyclyl; wherein said $C_{1-20}$alkyl is substituted with a substituent selected from the group consisting of halo, cyano, hydroxy, —C(=O)—$NR^{13}R^{14}$, —O—C(=O)—$C_{1-6}$alkyl, $C_{1-6}$alkyl-O—, $C_{1-6}$alkyl-S—, aryl, heteroaryl, heterocyclyl, and $C_{3-10}$cycloalkyl, or from the formula:

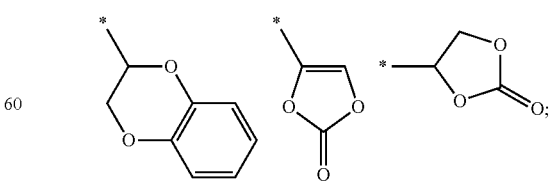

more in particular $R^{21}$ is selected from the group consisting of $C_{1-20}$alkyl; $C_{3-10}$cycloalkyl; and optionally substituted aryl; wherein said $C_{1-20}$alkyl is substituted with a substituent selected from the group consisting of halo, —O—C(=O)—C$_{1-6}$alkyl, or from the formula:

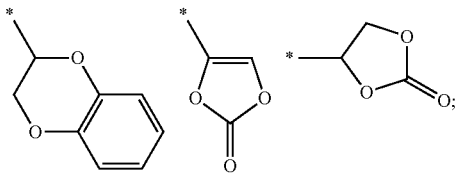

heterocyclyl as used herein is selected from the group consisting of piperidinyl, pyrrolidinyl, morpholinyl, thiomorpholinyl, piperazinyl, 1,3-dioxanyl, 3-dioxolanyl, tetrahydroquinolinyl, tetrahydroisoquinolinyl, indolinyl, tetrahydropyranyl, tetrahydrofuranyl and hexahydrofuro[3,2-b]furanyl; in particular piperidinyl, 1,3-dioxanyl, indolinyl, tetrahydropyranyl and tetrahydrofuranyl;

optionally substituted C$_{3-10}$cycloalkyl as used herein is selected from the group consisting of cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred; wherein said C$_{3-10}$cycloalkyl is optionally substituted with 1, 2, 3, or more in particular 1, 2 or 3; more in particular 1 or 2; even more in particular 1 substituent selected from halogen, hydroxyl, oxo, nitro, amino, cyano, C$_{1-4}$alkyl, C$_{3-6}$cycloalkyl, C$_{1-4}$alkoxy, or —SO$_2$—NH$_2$, optionally substituted heterocyclyl as used herein is selected from the group consisting of piperidinyl, pyrrolidinyl, morpholinyl, thiomorpholinyl, piperazinyl, 1,3-dioxanyl, 3-dioxolanyl, tetrahydroquinolinyl, tetrahydroisoquinolinyl, indolinyl, tetrahydropyranyl, tetrahydrofuranyl and hexahydrofuro[3,2-b]furanyl; in particular piperidinyl, 1,3-dioxanyl, indolinyl, tetrahydropyranyl and tetrahydrofuranyl; wherein said heterocyclyl is optionally substituted with 1, 2, 3 or more; in particular 1 substituent selected from the group consisting of halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —SO$_2$—NH$_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —SO$_2$R$^a$, alkylthio, carboxyl, and the like, wherein R$^a$ is alkyl or cycloalkyl; preferably selected from halogen, hydroxyl, oxo, nitro, amino, cyano, C$_{1-4}$alkyl, C$_{3-6}$cycloalkyl, C$_{1-4}$alkoxy, or —SO$_2$—NH$_2$, aryl as used herein is selected from the group consisting of phenyl, naphtyl, 1,4-dihydro naphtyl, or 1,2,3,4-tetrahydronaphtyl wherein said aryl is optionally substituted with 1, 2, 3, 4 or 5 substituents selected from halogen, nitro, C$_{1-4}$alkyl, C$_{1-4}$alkyloxy, or C$_{1-4}$alkylthio; in particular phenyl or 1,2,3,4-tetrahydronaphtyl wherein said aryl is optionally substituted with 1, 2, 3, 4 or 5 substituents selected from halogen, oxo, nitro, C$_{1-4}$alkyl, C$_{1-4}$alkyloxy, or C$_{1-4}$alkylthio; more in particular phenyl optionally substituted with 1, 2, 3, 4 or 5 substituents selected from halogen, nitro, C$_{1-4}$alkyl, C$_{1-4}$alkyloxy, or C$_{1-4}$alkylthio;

heteroaryl as used herein is selected from the group consisting of furanyl, thiophenyl, pyrrolyl, oxazolyl, thiazolyl, imidazolyl, pyrazolyl, isoxazolyl, isothiazolyl, pyridinyl, pyridazinyl, pyrimidinyl, pyrazinyl, triazinyl, benzofuranyl, benzopyranyl, 1(4H)-benzopyranyl, 1(2H)-benzopyranyl, 3,4-dihydro-1(2H)-benzopyranyl, and 2,3-dihydro-1(4H)-benzopyranyl wherein said heteroaryl is optionally substituted with 1, 2, 3, 4 or 5 substituents selected from halogen, oxo, nitro, C$_{1-4}$alkyl, C$_{1-4}$alkyloxy, or C$_{1-4}$alkylthio; in particular furanyl, thiohenyl, pyridinyl, benzopyranyl, 1(2H)-benzopyranyl, 3,4-dihydro-1(2H)-benzopyranyl, and 2,3-dihydro-1(4H)-benzopyranyl wherein said heteroaryl is optionally substituted with 1, 2, 3, 4 or 5 substituents selected from halogen, oxo, or C$_{1-4}$alkyl;

Y is 2-oxo-2,3-dihydrobenzofuranyl or Y is a phenyl, indolyl or thiophenyl, said phenyl indolyl and thiophenyl being substituted with a substituent selected from the group consisting of —C(=O)—OR$^{21}$; —C(=O)—SR$^{22}$; —C(=O)—NR$^3$R$^4$; —NR$^5$R$^6$; —O—C$_{1-6}$alkyl; —C$_{1-6}$alkyl; or —C$_{2-8}$alkenyl; said —C(=O)—OR$^{21}$; —C(=O)—SR$^{22}$; —C(=O)—NR$^3$R$^4$; —NR$^5$R$^6$; —O—C$_{1-6}$alkyl; —C$_{1-6}$alkyl; or —C$_{2-8}$alkenyl being bound at the meta or para position of Y, vis-à-vis the binding of Y to the remainder of the molecule; and wherein said —O—C$_{1-6}$alkyl or —C$_{2-8}$alkenyl is substituted with a substituent selected from the group consisting of C(=O)—OR$^{21}$; —C(=O)—SR$^{22}$; —C(=O)—NR$^3$R$^4$; Het$^1$; —O-Het$^2$; and —S-Het$^3$;

with the proviso that when Y is a phenyl, indolyl or thiophenyl, said phenyl indolyl and thiophenyl being substituted with —C(=O)—OR$^{21}$; or —C(=O)—SR$^{22}$; and wherein said R$^{21}$ or R$^{22}$ represents an unsubstituted C$_{1-20}$alkyl; said —C(=O)—OR$^{21}$; or —C(=O)—SR$^{22}$; is at the meta or para position vis-à-vis the binding of said phenyl, indolyl or thiophenyl to the remainder of the molecule and as represented in formulae IIa, IIb, IIIa and IIIb below.

An interesting group of compounds, are those compounds of the present invention presented by formula Ia

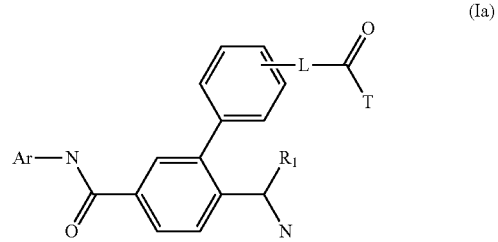

(Ia)

wherein;
R$^1$ is selected form the group comprising hydrogen, C$_{1-4}$alkyl or C$_{3-6}$cycloalkyl;
Ar is selected from the group comprising:

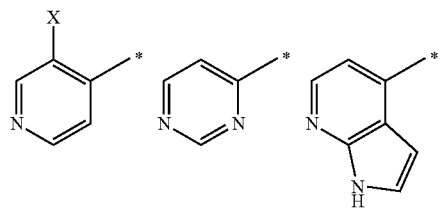

Wherein X is selected from the group comprising hydrogen or halo;
L is a direct bond, C$_{1-4}$alkyl, or —O—C$_{1-4}$alkyl;
T is —O—R$^{21}$ or —NR$^3$R$^4$;
R$^3$ is selected from the group consisting of hydrogen; C$_{1-20}$alkyl optionally substituted with 1, 2 or 3 substituents each independently selected from the group consisting of —C(=O)—OR$^{21}$; —C(=O)—SR$^{22}$; —C(=O)—NR$^7$R$^8$; Het$^1$; —O-Het$^2$; —S-Het$^3$; C$_{1-6}$alkyl-S— and C$_{1-6}$alkyl-O—; in particular R$^3$ is hydrogen;

R$^4$ is selected from the group consisting of C$_{1-20}$alkyl substituted with 1, 2 or 3 substituents each independently selected from the group consisting of —C(=O)—OR$^{21}$; —C(=O)—SR$^{22}$; —C(=O)—NR$^7$R$^8$; Het$^1$; —O-Het$^2$; —S-Het$^3$; C$_{1-6}$alkyl-S— and C$_{1-6}$alkyl-O—; more in particular R$^4$ is selected from the group consisting of C$_{1-20}$alkyl substituted with 1, 2 or 3 substituents each independently selected from the group of —C(=O)—OR$^{21}$; —C(=O)—SR$^{22}$; —C(=O)—NR$^7$R$^8$; Het$^1$; —O-Het$^2$; and —S-Het$^3$; or;

R$^3$ and R$^4$ together with the nitrogen atom to which they are attached form a heterocycle substituted with one substituent selected from the group consisting of —C(=O)—OR$^{21}$; —C(=O)—SR$^{22}$; —C(=O)—NR$^9$R$^{10}$; Het$^1$; —O-Het$^2$; —S-Het$^3$; or C$_{1-6}$alkyl wherein said C$_{1-6}$alkyl is substituted with 1, 2, or 3 substituents each independently selected from the group consisting of —C(=O)—OR$^{21}$; —C(=O)—SR$^{22}$; —C(=O)—NR$^9$R$^{10}$; Het$^1$; —O-Het$^2$; and —S-Het$^3$; in particular R$^3$ and R$^4$ together with the nitrogen atom to which they are attached form a heterocycle substituted with one substituent selected from the group consisting of —C(=O)—OR$^{21}$; —C(=O)—SR$^{22}$; —C(=O)—NR$^9$R$^{10}$; Het$^1$; or C$_{1-6}$alkyl wherein said C$_{1-6}$alkyl is substituted with 1, 2, or 3 substituents each independently selected from the group consisting of Het$^1$; —O-Het$^2$; and —S-Het$^3$;

R$^7$ or R$^8$ are independently selected from the group consisting of hydrogen; or C$_{1-6}$alkyl substituted with 1, 2, or 3 substituents each independently selected from the group consisting of aryl, heteroaryl, C$_{3-6}$cycloalkenyl, —C(=O)—OR$^{21}$; and —C(=O)—NH$_2$; in particular R$^7$ or R$^8$ are independently selected from the group consisting of hydrogen; or C$_{1-6}$alkyl substituted with 1, 2, or 3 substituents each independently selected from the group consisting of —C(=O)—OR$^{21}$; and —C(=O)—NH$_2$;

R$^9$ or R$^{10}$ are independently selected from the group consisting of hydrogen; or C$_{1-6}$alkyl substituted with 1, 2, or 3, —C(=O)—OR$^{21}$ substituents;

R$^{13}$ or R$^{14}$ are independently selected from the group consisting of hydrogen; C$_{1-6}$alkyl; C$_{1-6}$alkyl; C$_{1-6}$alkyl-O—C$_{1-6}$alkyl-; C$_{1-6}$alkyl-S—C$_{1-6}$alkyl-; or C$_{1-6}$alkyl-C(=O)— and wherein each of said C$_{1-6}$alkyl; C$_{1-6}$alkyl-O—C$_{1-6}$alkyl-; C$_{1-6}$alkyl-S—C$_{1-6}$alkyl-; or C$_{1-6}$alkyl-C(=O)— is substituted with 1, 2, or 3 substituents each independently selected from the group consisting of —C(=O)—OR$^{21}$; —C(=O)—SR$^{22}$; Het$^1$; —O-Het$^2$; and —S-Het$^3$;

R$^{21}$ is selected from the group consisting of C$_{1-20}$alkyl; C$_{1-20}$alkenyl; C$_{1-20}$alkynyl; optionally substituted C$_{3-15}$cycloalkyl; optionally substituted heterocyclyl; and optionally substituted aryl;

wherein said C$_{1-20}$alkyl is optionally substituted with 1, 2, 3 or more substituents selected from the group consisting of halo, cyano, hydroxy, aryl-O—, aryl-S—, aryl-S(=O)$_2$—, aryl-C(=O), —C(=O)—NR$^{13}$R$^{14}$, —O—C(=O)—C$_{1-6}$alkyl, C$_{1-6}$alkyl-O—, C$_{1-6}$alkyl-S—, aryl, heteroaryl, heterocyclyl and C$_{3-15}$cycloalkyl or from the formula:

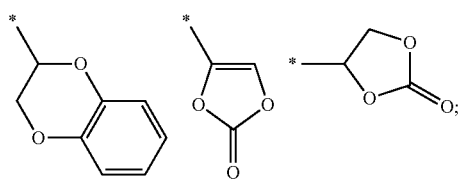

or

R$^{21}$ taken together with the oxycarbonyl and phenyl to which it is attached forms a cyclic ester consisting of

wherein q is an integer from 1 to 6;

R$^{22}$ is C$_{1-20}$alkyl optionally substituted with 1, 2, 3 or more halo substituents;

Het$^1$, Het$^2$ or Het$^3$ are independently selected from the group comprising;

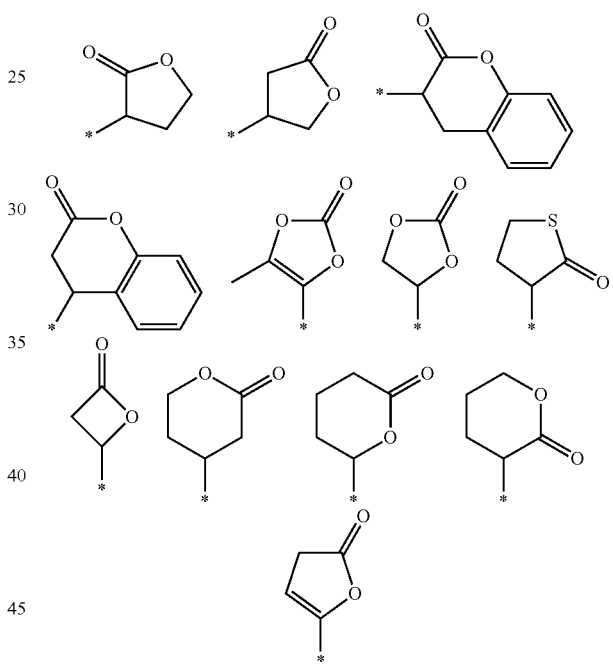

In a further embodiment the present invention provides those compounds of formula (Ia) wherein one or more of the following restrictions apply;

Ar represents pyridinyl, optionally substituted with halo; in particular Ar represents pyridinyl substituted with fluoro; in an even further embodiment Ar represents

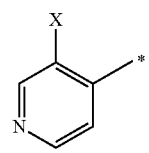

wherein X is hydrogen or halo; in particular X is hydrogen or fluoro; more in particular X is hydrogen;

R$^1$ represents hydrogen or C$_{1-4}$alkyl; in particular C$_{1-4}$alkyl; more in particular methyl;

$R^3$ is hydrogen;

$R^4$ is —$C_{1-6}$alkyl substituted with a substituent selected from —O-Het², or —S-Het³; with in a particular embodiment said Het² or Het³ being selected from the group consisting of

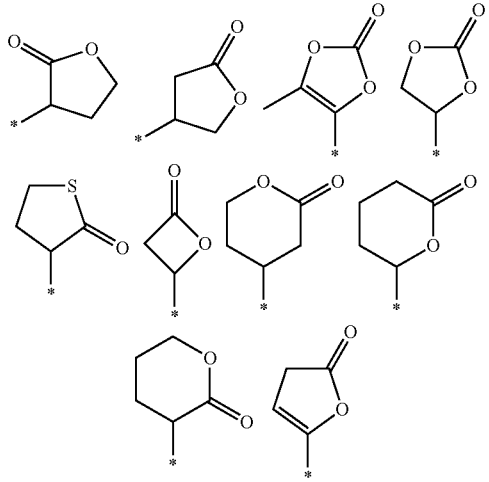

$R^4$ is —$C_{1-6}$alkyl substituted with a substituent selected from —C(=O)—OR²¹, —C(=O)—SR²², —C(=O)—NR⁷R⁸, or Het¹; in particular —$C_{1-6}$alkyl substituted with a substituent selected from —C(=O)—OR²¹, or Het¹; with in a particular embodiment said R²¹ being a —$C_{1-6}$alkyl and said Het¹ being i

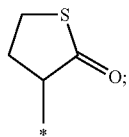

or $R^3$ and $R^4$ together with the nitrogen atom to which they are attached form a heterocycle substituted with $C_{1-6}$alkyl wherein said $C_{1-6}$alkyl is substituted with 1, 2, or 3 substituents each independently selected from the group consisting of —C(=O)—OR²¹; and —C(=O)—NR⁹R¹⁰;

R²¹ is selected from the group consisting of $C_{1-20}$alkyl; optionally substituted $C_{3-10}$cycloalkyl; optionally substituted aryl; and optionally substituted heterocyclyl; wherein said $C_{1-20}$alkyl is optionally substituted with a substituent selected from the group consisting of halo, cyano, hydroxy, —C(=O)—NR¹³R¹⁴, —O—C(=O)—$C_{1-6}$alkyl, $C_{1-6}$alkyl-O—, $C_{1-6}$alkyl-S—, aryl, heterocyclyl, and $C_{3-10}$cycloalkyl, or from the formula:

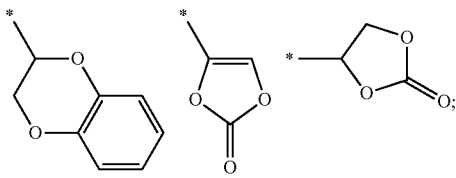

in particular R²¹ is selected from the group consisting of $C_{1-20}$alkyl; optionally substituted $C_{3-10}$cycloalkyl; optionally substituted aryl; and optionally substituted heterocyclyl; wherein said $C_{1-20}$alkyl is substituted with a substituent selected from the group consisting of halo, cyano, hydroxy, —C(=O)—NR¹³R¹⁴, —O—C(=O)—$C_{1-6}$alkyl, $C_{1-6}$alkyl-O—, $C_{1-6}$alkyl-S—, aryl, heterocyclyl, and $C_{3-10}$cycloalkyl, or from the formula:

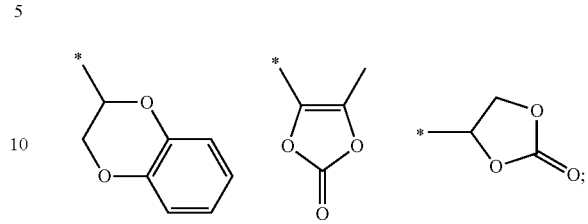

more in particular R²¹ is selected from the group consisting of $C_{1-20}$alkyl; optionally substituted $C_{3-10}$cycloalkyl; optionally substituted aryl; and optionally substituted heterocyclyl; wherein said $C_{1-20}$alkyl is substituted with a substituent selected from the group consisting of halo, cyano, hydroxy, —O—C(=O)—$C_{1-6}$alkyl, $C_{1-6}$alkyl-S—, aryl, heterocyclyl, and $C_{3-10}$cycloalkyl, or from the formula:

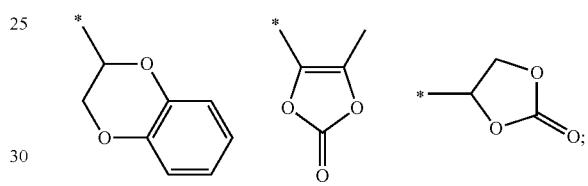

even more in particular R²¹ is selected from the group consisting of $C_{1-20}$alkyl; $C_{3-10}$cycloalkyl; and optionally substituted aryl; wherein said $C_{1-20}$alkyl is substituted with a substituent selected from the group consisting of halo, —O—C(=O)—$C_{1-6}$alkyl, or from the formula:

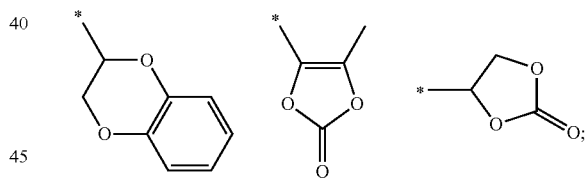

heterocyclyl as used herein is selected from the group consisting of piperidinyl, pyrrolidinyl, morpholinyl, thiomorpholinyl, piperazinyl, 1,3-dioxanyl, 3-dioxolanyl, tetrahydroquinolinyl, tetrahydroisoquinolinyl, indolinyl, tetrahydropyranyl, tetrahydrofuranyl and hexahydrofuro[3,2-b]furanyl; in particular piperidinyl, 1,3-dioxanyl, indolinyl, tetrahydropyranyl and tetrahydrofuranyl;

optionally substituted $C_{3-10}$cycloalkyl as used herein is selected from the group consisting of cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred; wherein said $C_{3-10}$cycloalkyl is optionally substituted with 1, 2, 3, or more in particular 1, 2 or 3; more in particular 1 or 2; even more in particular 1 substituent selected from halogen, hydroxyl, oxo, nitro, amino, cyano, $C_{1-4}$alkyl, $C_{3-6}$cycloalkyl, $C_{1-4}$alkoxy, or —SO₂—NH₂, optionally substituted heterocyclyl as used herein is selected from the group consisting of piperidinyl, pyrrolidinyl, morpholinyl, thiomorpholinyl, piperazinyl, 1,3-dioxanyl, 3-dioxolanyl, tetrahydroquinolinyl, tetrahydroisoquinolinyl, indolinyl, tetrahydropyranyl, tetrahydrofuranyl and hexahydrofuro[3,2-b]furanyl; in particular piperidinyl, 1,3-dioxanyl, indolinyl, tetrahydropyranyl and tetrahydrofuranyl; wherein said heterocyclyl is optionally substituted with 1, 2, 3 or more; in particular 1 substituent selected from the group consisting of halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —$SO_2R^a$, alkylthio, carboxyl, and the like, wherein $R^a$ is alkyl or cycloalkyl; preferably selected from halogen, hydroxyl, oxo, nitro, amino, cyano, $C_{1-4}$alkyl, $C_{3-6}$cycloalkyl, $C_{1-4}$alkoxy, or —$SO_2$—$NH_2$, aryl as used herein is selected from the group consisting of phenyl, naphtyl, 1,4-dihydro naphtyl, or 1,2,3,4-tetrahydronaphthyl wherein said aryl is optionally substituted with 1, 2, 3, 4 or 5 substituents selected from halogen, nitro, $C_{1-4}$alkyl, $C_{1-4}$alkyloxy, or $C_{1-4}$alkylthio; in particular phenyl or 1,2,3,4-tetrahydronaphthyl wherein said aryl is optionally substituted with 1, 2, 3, 4 or 5 substituents selected from halogen, oxo, nitro, $C_{1-4}$alkyl, $C_{1-4}$alkyloxy, or $C_{1-4}$alkylthio; more in particular phenyl optionally substituted with 1, 2, 3, 4 or 5 substituents selected from halogen, nitro, $C_{1-4}$alkyl, $C_{1-4}$alkyloxy, or $C_{1-4}$alkylthio;

heteroaryl as used herein is selected from the group consisting of furanyl, thiophenyl, pyrrolyl, oxazolyl, thiazolyl, imidazolyl, pyrazolyl, isoxazolyl, isothiazolyl, pyridinyl, pyridazinyl, pyrimidinyl, pyrazinyl, triazinyl, benzofuranyl, benzopyranyl, 1(4H)-benzopyranyl, 1(2H)-benzopyranyl, 3,4-dihydro-1(2H)-benzopyranyl, and 2,3-dihydro-1(4H)-benzopyranyl wherein said heteroaryl is optionally substituted with 1, 2, 3, 4 or 5 substituents selected from halogen, oxo, nitro, $C_{1-4}$alkyl, $C_{1-4}$alkyloxy, or $C_{1-4}$alkylthio; in particular furanyl, thiohenyl, pyridinyl, benzopyranyl, 1(2H)-benzopyranyl, 3,4-dihydro-1(2H)-benzopyranyl, and 2,3-dihydro-1(4H)-benzopyranyl wherein said heteroaryl is optionally substituted with 1, 2, 3, 4 or 5 substituents selected from halogen, oxo, or $C_{1-4}$alkyl;

-L is at the meta or para position of the phenyl ring vis-à-vis the binding of said phenyl ring to the remainder of the molecule in analogy with the —$COOR^{21}$ group shown in formulae IIa and IIb;

the proviso that when L is a direct bond and T is —O—$R^{21}$, and wherein $R^{21}$ is an unsubstituted $C_{1-20}$alkyl, said L-(C(=O))-T is bond at the meta or para position of the phenyl ring vis-à-vis the binding of said phenyl ring to the remainder of the molecule in analogy with the —$COOR^{21}$ group shown in formulae IIa and IIb.

An interesting group of compounds, are those compounds of the present invention presented by formula Ib

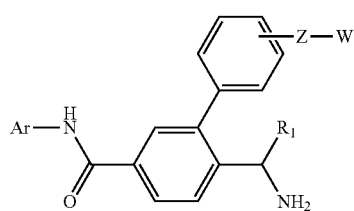

(Ib)

wherein;
$R^1$ is selected form the group comprising hydrogen, $C_{1-4}$alkyl or $C_{3-6}$cycloalkyl;

Ar is selected from the group comprising:

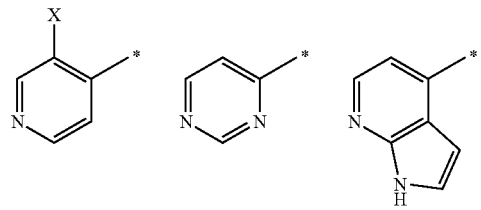

Wherein X is selected from the group comprising hydrogen or halo;
Z is a bivalent radical selected from the group consisting of —O—; —$NR^5$—; and —$NR^5$—C(=O)—;
W represents $C_{1-6}$alkyl substituted with a substituent selected from —O-$Het^2$; —S-$Het^3$; or C(=O)—$NR^3R^4$; and
wherein $R^3$, $R^4$, $R^5$, $Het^2$ and $Het^3$ are defined as for any one of the aforementioned embodiments of the compounds of formula I or Ia hereinbefore.

In one embodiment of the present invention the compounds of formula Ib are further characterized in that
$R^3$ is selected from the group consisting of hydrogen; $C_{1-20}$alkyl optionally substituted with 1, 2 or 3 substituents each independently selected from the group consisting of —C(=O)—$OR^{21}$; —C(=O)—$SR^{22}$; —C(=O)—$NR^7R^5$; $Het^1$; —O-$Het^2$; —S-$Het^3$; $C_{1-6}$alkyl-S— and $C_{1-6}$alkyl-O—; in particular $R^3$ is hydrogen;
$R^4$ is selected from the group consisting of $C_{1-20}$alkyl substituted with 1, 2 or 3 substituents each independently selected from the group consisting of —C(=O)—$OR^{21}$; —C(=O)—$SR^{22}$; —C(=O)—$NR^7R^8$; $Het^1$; —O-$Het^2$; —S-$Het^3$; $C_{1-6}$alkyl-S— and $C_{1-6}$alkyl-O—; more in particular $R^4$ is selected from the group consisting of $C_{1-20}$alkyl substituted with 1, 2 or 3 substituents each independently selected from the group consisting of —C(=O)—$OR^{21}$; —C(=O)—$SR^{22}$; —C(=O)—$NR^7R^8$; $Het^1$; —O-$Het^2$; and —S-$Het^3$; or;
$R^3$ and $R^4$ together with the nitrogen atom to which they are attached form a heterocycle substituted with one substituent selected from the group consisting of —C(=O)—$OR^{21}$; —C(=O)—$SR^{22}$; —C(=O)—$NR^9R^{10}$; $Het^1$; —O-$Het^2$; —S-$Het^3$; or $C_{1-6}$alkyl wherein said $C_{1-6}$alkyl is substituted with 1, 2, or 3 substituents each independently selected from the group consisting of —C(=O)—$OR^{21}$; —C(=O)—$SR^{22}$; —C(=O)—$NR^9R^{10}$; $Het^1$; —O-$Het^2$; and —S-$Het^3$; in particular $R^3$ and $R^4$ together with the nitrogen atom to which they are attached form a heterocycle substituted with one substituent selected from the group consisting of —C(=O)—$OR^{21}$; —C(=O)—$SR^{22}$; —C(=O)—$NR^9R^{10}$; $Het^1$; or $C_{1-6}$alkyl wherein said $C_{1-6}$alkyl is substituted with 1, 2, or 3 substituents each independently selected from the group consisting of $Het^1$; —O-$Het^2$; and —S-$Het^3$;
$R^5$ is hydrogen;
$R^7$ or $R^8$ are independently selected from the group consisting of hydrogen; or $C_{1-6}$alkyl substituted with 1, 2, or 3 substituents each independently selected from the group consisting of aryl, heteroaryl, $C_{3-6}$cycloalkenyl, —C(=O)—$OR^{21}$; and —C(=O)—$NH_2$; in particular $R^7$ or $R^8$ are independently selected from the group consisting of hydrogen; or $C_{1-6}$alkyl substituted with 1, 2, or 3 substituents each independently selected from the group consisting of —C(=O)—$OR^{21}$; and —C(=O)—$NH_2$;
$R^9$ or $R^{10}$ are independently selected from the group consisting of hydrogen; or $C_{1-6}$alkyl substituted with 1, 2, or 3, —C(=O)—$OR^{21}$ substituents;

R[13] or R[14] are independently selected from the group consisting of hydrogen; $C_{1-6}$alkyl; $C_{1-6}$alkyl; $C_{1-6}$alkyl-O—$C_{1-6}$alkyl-; $C_{1-6}$alkyl-S—$C_{1-6}$alkyl-; or $C_{1-6}$alkyl-C(=O)— and wherein each of said $C_{1-6}$alkyl; $C_{1-6}$alkyl-O—$C_{1-6}$alkyl-; $C_{1-6}$alkyl-S—$C_{1-6}$alkyl-; or $C_{1-6}$alkyl-C(=O)— is substituted with 1, 2, or 3 substituents each independently selected from the group consisting of —C(=O)—OR[21]; —C(=O)—SR[22]; Het[1]; —O-Het[2]; and —S-Het[3];

R[21] is selected from the group consisting of $C_{1-20}$alkyl; $C_{1-20}$alkenyl; $C_{1-20}$alkynyl; optionally substituted $C_{3-15}$cycloalkyl; optionally substituted heterocyclyl; and optionally substituted aryl;

wherein said $C_{1-20}$alkyl is optionally substituted with 1, 2, 3 or more substituents selected from the group consisting of halo, cyano, hydroxy, aryl-O—, aryl-S—, aryl-S(=O)$_2$—, aryl-C(=O), —C(=O)—NR[13]R[14], —O—C(=O)—$C_{1-6}$alkyl, $C_{1-6}$alkyl-O—, $C_{1-6}$alkyl-S—, aryl, heteroaryl, heterocyclyl and $C_{3-15}$cycloalkyl or from the formula:

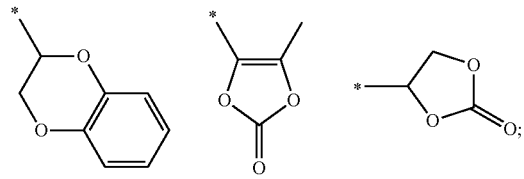

or

R[21] taken together with the oxycarbonyl and phenyl to which it is attached forms a cyclic ester consisting of

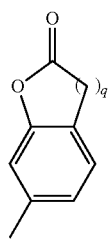

wherein q is an integer from 1 to 6;

R[22] is $C_{1-20}$alkyl optionally substituted with 1, 2, 3 or more halo substituents;

Het[1], Het[2] or Het[3] are independently selected from the group comprising;

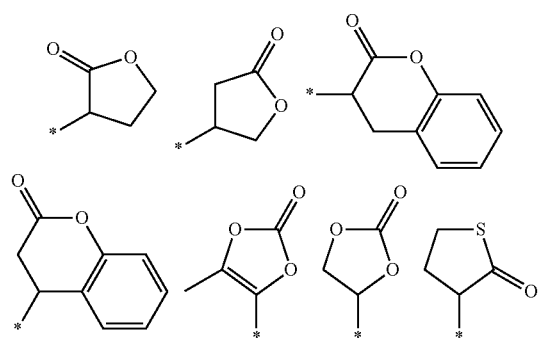

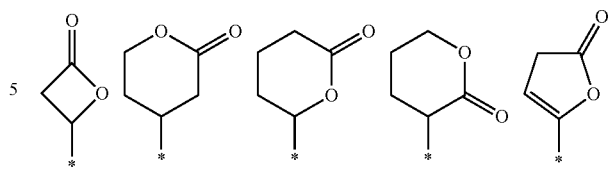

In a further embodiment the present invention provides those compounds of formula (Ib) wherein one or more of the following restrictions apply;

R[3] is hydrogen;

R[4] is —$C_{1-6}$alkyl substituted with a substituent selected from —O-Het[2], or —S-Het[3]; with in a particular embodiment said Het[2] or Het[3] being selected from the group consisting of

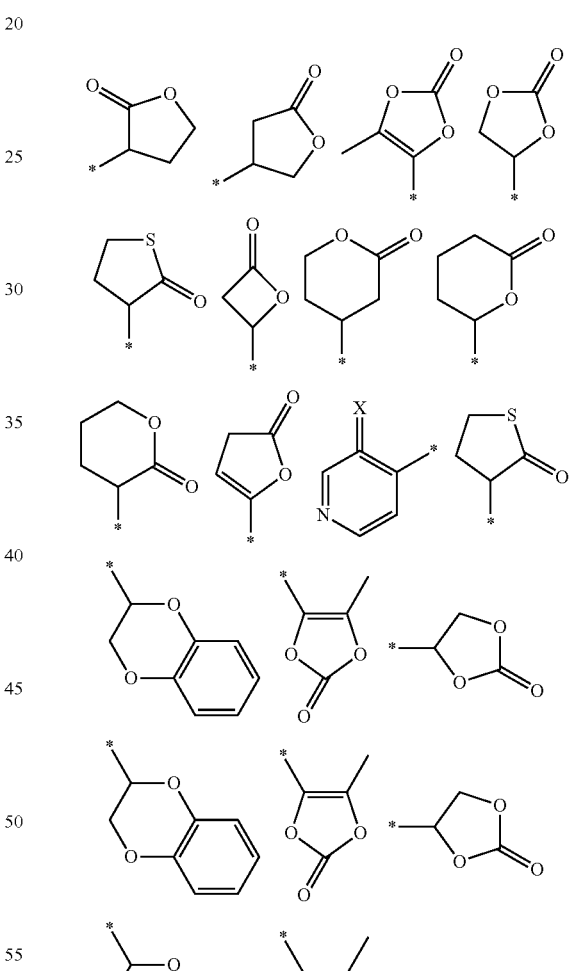

In a preferred embodiment the present invention provides compounds of formula IIa, IIIa, IVa, Va, VIa, VIIa, VIIIa, IXa, Xa, IIb, IIIb, IVb, Vb, VIb, VIIb, VIIIb, IXb, Xb, XI, XII, XIII, XIV, XV, XVI, XVII, XVIIIa, XIXa, XXa, XXIa, XXIb, XXIIa, XXIIIa or XXIVa.

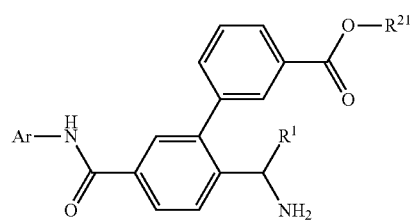 IIa
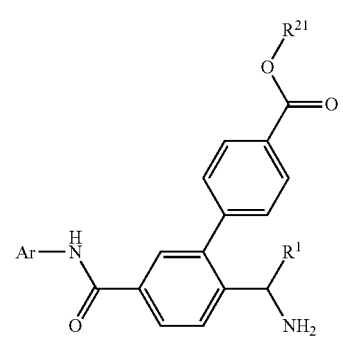 IIb
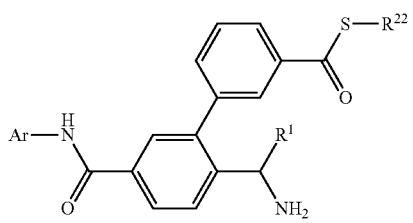 IIIa
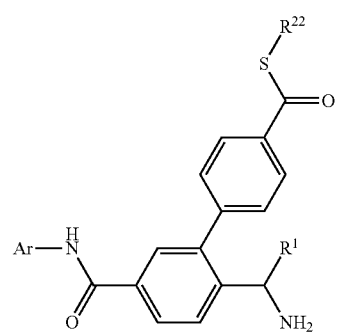 IIIb
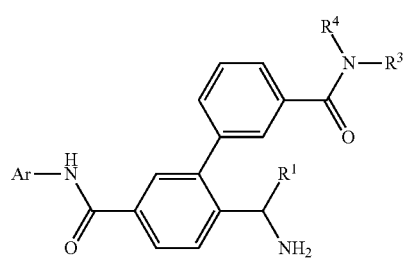 IVa
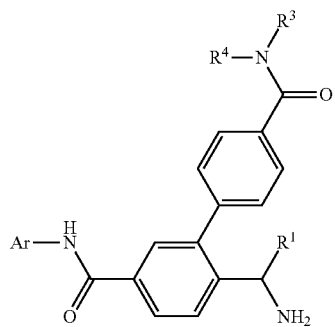 IVb
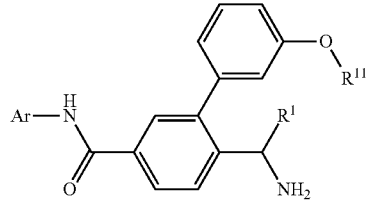 Va
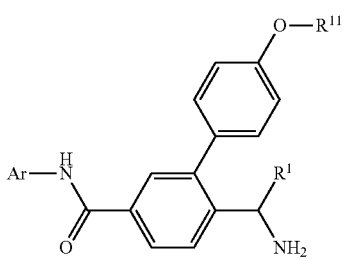 Vb
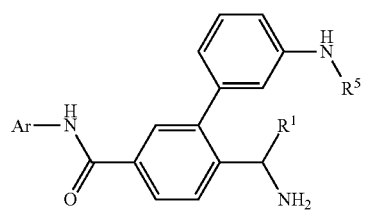 VIa
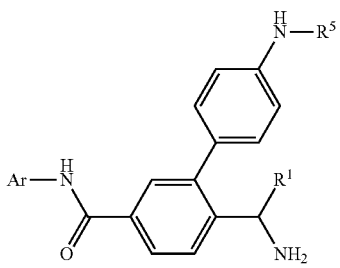 VIb
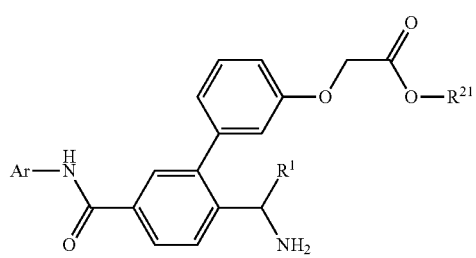 VIIa

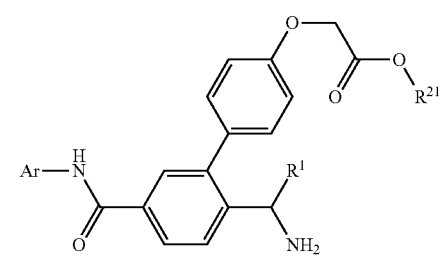
VIIb
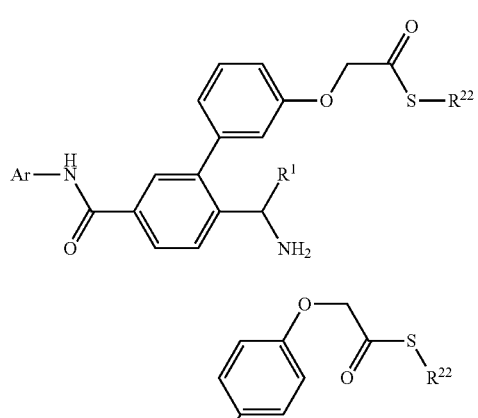
VIIIa
VIIIb
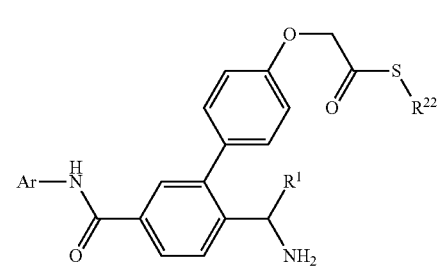
IXa
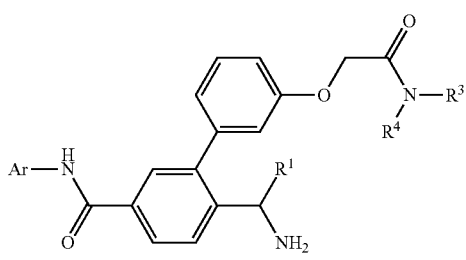
IXb
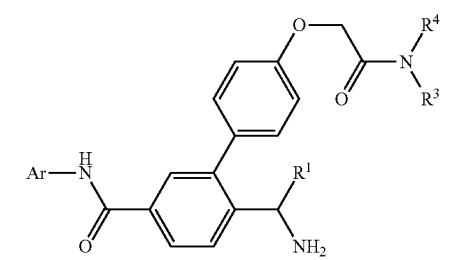
Xa
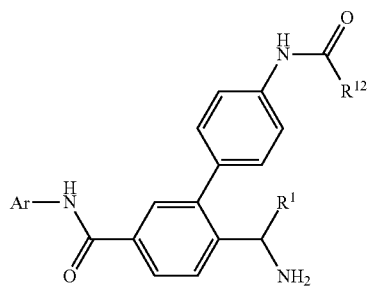
Xb
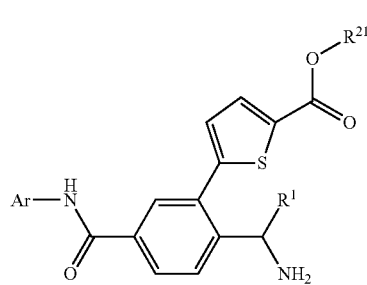
XI
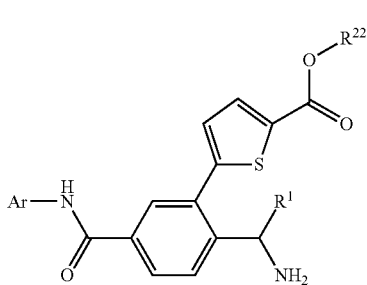
XII
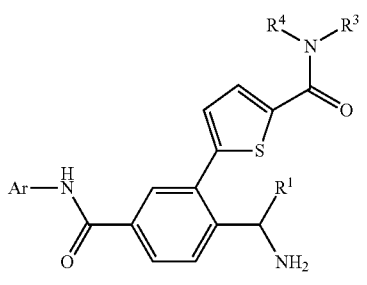
XIII
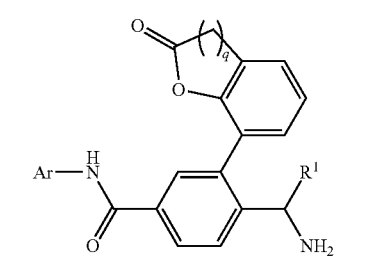
XIV

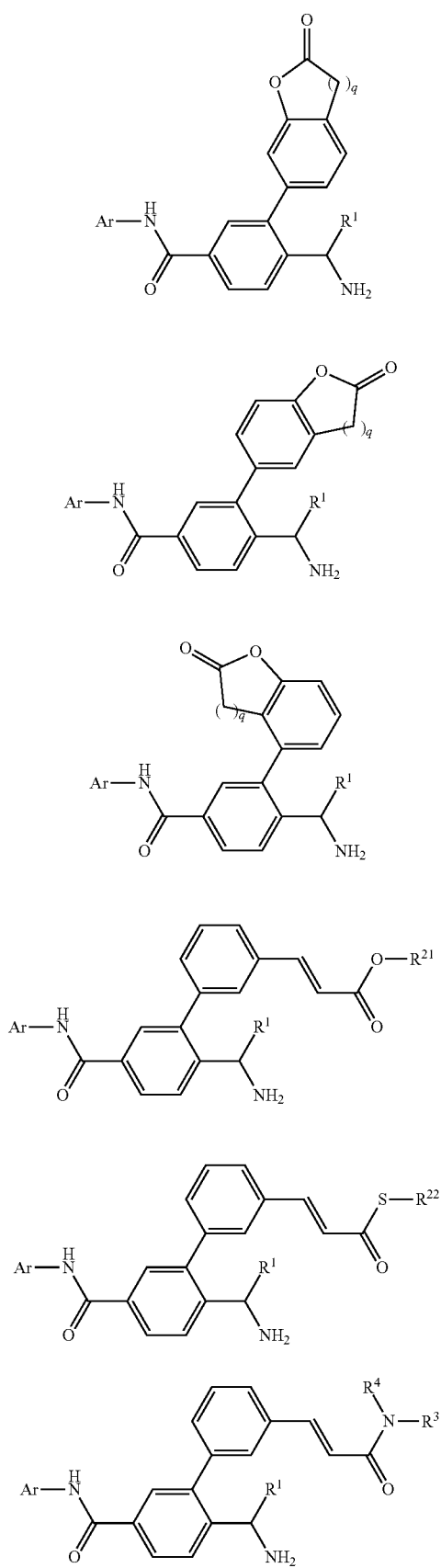
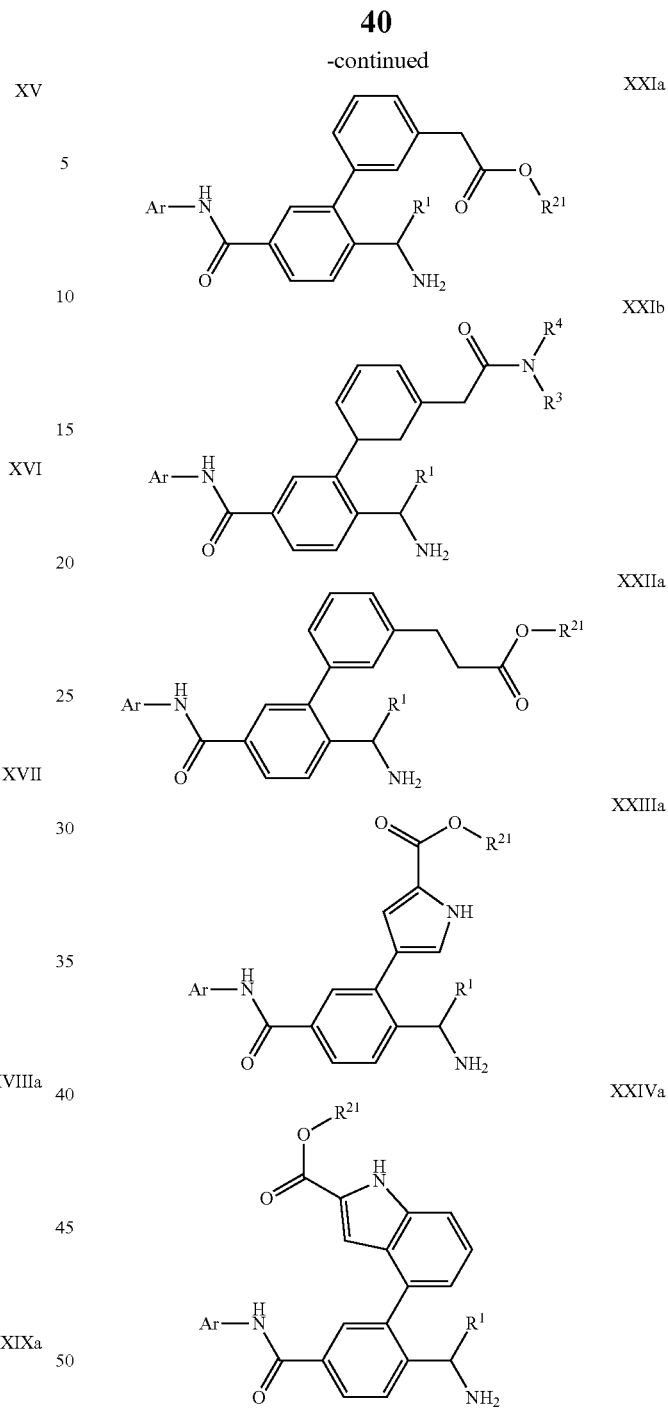

wherein;
q is an integer from 2 to 6;

$R^{11}$ is a substituted $C_{1-6}$alkyl, or a substituted —$C_{2-8}$alkenyl; said —$C_{1-6}$alkyl and —$C_{2-8}$alkenyl each independently substituted with a substituent selected from the group consisting of C(=O)—$OR^{21}$; —C(=O)—$SR^{22}$; —C(=O)—$NR^3R^4$; $Het^1$; —O-$Het^2$; and —S-$Het^3$;

$R^{12}$ is a substituted $C_{1-6}$alkyl, a substituted $C_{1-6}$alkyl-S—$C_{1-6}$alkyl or a substituted —$C_{2-8}$alkenyl; said —$C_{1-6}$alkyl, $C_{1-6}$alkyl-S—$C_{1-6}$alkyl and —$C_{2-8}$alkenyl each independently substituted with 1, 2, or 3 substituents each independently selected from the group consisting of aryl, heteroaryl, $C_{3-6}$cycloalkenyl, —C(=O)—$OR^{21}$; —C(=O)—$SR^{22}$; $Het^1$; —O-$Het^2$; and —S-$Het^3$; and wherein Ar, $R^1$, $R^{21}$, $R^{22}$, $R^3$, $R^4$, $R^5$, $R^6$, $Het^1$, $Het^2$ and $Het^3$ have the same meanings than those defined herein before.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful as kinase inhibitors, more in particular for the inhibition of at least one ROCK kinase, selected from ROCKI and ROCKII, in particular soft ROCK inhibitors.

The present invention further provides the use of a compound as defined hereinbefore or the use of a composition comprising said compound, as a human or veterinary medicine, in particular for prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeration, function, inflammation, fibrosis, excessive cell proliferation, excessive angiogenesis, hyperreactivity, barrier dysfunction, neurodegeration and remodeling.

In a further embodiment, the invention provides the use of a compound as defined hereinbefore, or the use of a composition comprising said compound in the prevention and/or treatment of at least one disease or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupus erythematosus, spasm, hypertension, chronic obstructive bladder disease, premature birth, infection, allergy, obesity, pancreatic disease and AIDS.

In a preferred embodiment, the invention provides the use of a compound as defined hereinbefore or the use of a composition comprising said compound in the prevention and/or treatment of eyes diseases including but not limited to retinopathy, optic neuropathy, glaucoma and degenerative retinal diseases such as macular degeneration, retinitis pigmentosa and inflammatory eye diseases, and/or for preventing, treating and/or alleviating complications and/or symptoms associated therewith.

In particular those compounds selected from the group consisting of;

Those compounds of formula I wherein; Y is an aryl or heteroaryl substituted with a substituent selected from the group consisting of —C(=O)—OR$^{21}$; C(=O)—SR$^{22}$; —C(=O)—NR$^3$R$^4$; —O—C$_{1-6}$alkyl; or —C$_{1-6}$alkyl; wherein said —O—C$_{1-6}$ alkyl or —C$_{1-6}$ alkyl are each independently substituted with a substituent selected from the group consisting of —C(=O)—OR$^{21}$, and Het$^1$; and R$^4$ is —C$_{1-6}$alkyl substituted with a substituent selected from —C(=O)—OR$^{21}$, —C(=O)—SR$^{22}$, or Het$^1$; and Those compounds of formula Ia wherein Ar represents

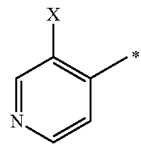

wherein X is hydrogen or halo,
L is a direct bond, C$_{1-4}$alkyl, or —O—C$_{1-4}$alkyl;
T is —O—R$^{21}$ or —NR$^3$R$^4$;
R$^1$ represents hydrogen or C$_{1-4}$alkyl;
R$^3$ is hydrogen;

R$^4$ is —C$_{1-6}$alkyl substituted with a substituent selected from —C(=O)—OR$^{21}$, —C(=O)—S$^{22}$, —C(=O)—NR$^7$R$^8$, or Het$^1$; in particular —C$_{1-6}$alkyl substituted with a substituent selected from —C(=O)—OR$^{21}$, or Het$^1$; with in a particular embodiment said R$^{21}$ being a —C$_{1-6}$alkyl; or R$^3$ and R$^4$ together with the nitrogen atom to which they are attached form a heterocycle substituted with C$_{1-6}$alkyl wherein said C$_{1-6}$alkyl is substituted with 1, 2, or 3 substituents each independently selected from the group consisting of —C(=O)—OR$^{21}$; and —C(=O)—NR$^9$R$^{10}$;

R$^9$ or R$^{10}$ are independently selected from the group consisting of hydrogen; or C$_{1-6}$alkyl substituted with 1, 2, or 3, —C(=O)—OR$^{21}$ substituents;

R$^{21}$ is selected from the group consisting of C$_{1-20}$alkyl; optionally substituted C$_{3-10}$cycloalkyl; optionally substituted aryl; and optionally substituted heterocyclyl; wherein said C$_{1-20}$alkyl is optionally substituted with a substituent selected from the group consisting of halo, cyano, hydroxy, C$_{1-6}$alkyl-O—, C$_{1-6}$alkyl-S—, aryl, heterocyclyl, and C$_{3-10}$cycloalkyl, or from the formula:

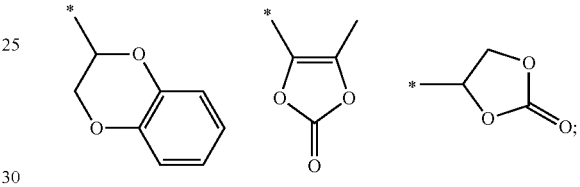

heterocyclyl as used herein is selected from the group consisting of piperidinyl, pyrrolidinyl, morpholinyl, thiomorpholinyl, piperazinyl, 1,3-dioxanyl, 3-dioxolanyl, tetrahydroquinolinyl, tetrahydroisoquinolinyl, indolinyl, tetrahydropyranyl, tetrahydrofuranyl and hexahydrofuro[3,2-b]furanyl; in particular piperidinyl, 1,3-dioxanyl, indolinyl, tetrahydropyranyl and tetrahydrofuranyl;

optionally substituted C$_{3-10}$cycloalkyl as used herein is selected from the group consisting of cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred; wherein said C$_{3-10}$cycloalkyl is optionally substituted with 1, 2, 3, or more in particular 1, 2 or 3; more in particular 1 or 2; even more in particular 1 substituent selected from halogen, hydroxyl, oxo, nitro, amino, cyano, C$_{1-4}$alkyl, C$_{3-6}$cycloalkyl, C$_{1-4}$alkoxy, or —SO$_2$—NH$_2$, optionally substituted heterocyclyl as used herein is selected from the group consisting of piperidinyl, pyrrolidinyl, morpholinyl, thiomorpholinyl, piperazinyl, 1,3-dioxanyl, 3-dioxolanyl, tetrahydroquinolinyl, tetrahydroisoquinolinyl, indolinyl, tetrahydropyranyl, tetrahydrofuranyl and hexahydrofuro[3,2-b]furanyl; in particular piperidinyl, 1,3-dioxanyl, indolinyl, tetrahydropyranyl and tetrahydrofuranyl; wherein said heterocyclyl is optionally substituted with 1, 2, 3 or more; in particular 1 substituent selected from the group consisting of halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —SO$_2$—NH$_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —SO$_2$R$^a$, alkylthio, carboxyl, and the like, wherein R$^a$ is alkyl or cycloalkyl; preferably selected from halogen, hydroxyl, oxo, nitro, amino, cyano, $C_{1-6}$alkyl, $C_{3-6}$cycloalkyl, $C_{1-4}$alkoxy, or —SO$_2$—NH$_2$, aryl as used herein is selected from the group consisting of phenyl, naphtyl, 1,4-dihydro naphtyl, or 1,2,3,4-tetrahydronaphtyl wherein said aryl is optionally substituted with 1, 2, 3, 4 or 5 substituents selected from halogen, nitro, $C_{1-4}$alkyl, $C_{1-4}$alkyloxy, or $C_{1-4}$alkylthio; in particular phenyl or 1,2,3,4-tetrahydronaphtyl wherein said aryl is optionally substituted with 1, 2, 3, 4 or 5 substituents selected from halogen, oxo, nitro, $C_{1-4}$alkyl, $C_{1-4}$alkyloxy, or $C_{1-4}$alkylthio; more in particular phenyl optionally substituted with 1, 2, 3, 4 or 5 substituents selected from halogen, nitro, $C_{1-4}$alkyl, $C_{1-4}$alkyloxy, or $C_{1-4}$alkylthio;

heteroaryl as used herein is selected from the group consisting of furanyl, thiophenyl, pyrrolyl, oxazolyl, thiazolyl, imidazolyl, pyrazolyl, isoxazolyl, isothiazolyl, pyridinyl, pyridazinyl, pyrimidinyl, pyrazinyl, triazinyl, benzofuranyl, benzopyranyl, 1(4H)-benzopyranyl, 1(2H)-benzopyranyl, 3,4-dihydro-1(2H)-benzopyranyl, and 2,3-dihydro-1(4H)-benzopyranyl wherein said heteroaryl is optionally substituted with 1, 2, 3, 4 or 5 substituents selected from halogen, oxo, nitro, $C_{1-4}$alkyl, $C_{1-4}$alkyloxy, or $C_{1-4}$alkylthio; in particular furanyl, thiohenyl, pyridinyl, benzopyranyl, 1(2H)-benzopyranyl, 3,4-dihydro-1(2H)-benzopyranyl, and 2,3-dihydro-1(4H)-benzopyranyl wherein said heteroaryl is optionally substituted with 1, 2, 3, 4 or 5 substituents selected from halogen, oxo, or $C_{1-4}$alkyl;

are particularly useful in the prevention and/or treatment of eyes diseases including but not limited to retinopathy, optic neuropathy, glaucoma and degenerative retinal diseases such as macular degeneration, retinitis pigmentosa and inflammatory eye diseases, and/or for preventing, treating and/or alleviating complications and/or symptoms associated therewith. It is accordingly an object of the present invention to provide said compounds for use in the treatment of eyes diseases including but not limited to retinopathy, optic neuropathy, glaucoma and degenerative retinal diseases such as macular degeneration, retinitis pigmentosa and inflammatory eye diseases, and/or for preventing, treating and/or alleviating complications and/or symptoms associated therewith; more in particular in the treatment of glaucoma. Alternatively, to provide a method for prevention and/or treatment of eye diseases selected from the group consisting of retinopathy, optic neuropathy, glaucoma, inflammatory eye diseases and degenerative retinal diseases such as macular degeneration and retinitis pigmentosa; preferably glaucoma; said method comprising administering to a subject in need thereof a therapeutic effective amount of a compound according to formula I; in particular a compound as defined hereinbefore.

In another preferred embodiment, the invention provides the use of a compound as defined hereinbefore or the use of a composition comprising said compound in the prevention and/or treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, and/or for preventing, treating and/or alleviating complications and/or symptoms associated therewith.

In particular those compounds selected from the group consisting of;

Those compounds of formula I wherein; Y is an aryl or heteroaryl substituted with a substituent selected from the group consisting of —C(=O)—NR$^3$R$^4$; —NR$^5$R$^6$; —O—$C_{1-6}$alkyl; or —$C_{1-6}$alkyl; wherein said —O—$C_{1-6}$alkyl or —$C_{1-6}$alkyl are each independently substituted with a substituent selected from the group consisting of —C(=O)—NR$^3$R$^4$, —O-Het$^2$ and S-Het$^3$; with in a particular embodiment said Het$^2$ or Het$^3$ independently being selected from the group comprising

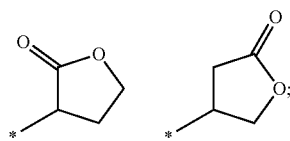

and

Those compounds of formula Ia wherein; Ar represents

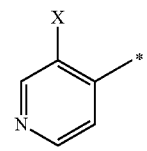

wherein X is hydrogen or halo;

L is a direct bond, $C_{1-4}$alkyl, or —O—$C_{1-4}$alkyl;

T is —O—R$^{21}$ or —NR$^3$R$^4$;

R$^1$ represents hydrogen or $C_{1-4}$alkyl;

R$^3$ is hydrogen;

R$^4$ is —$C_{1-6}$alkyl substituted with a substituent selected from —O-Het$^2$, or —S-Het$^3$; with in a particular embodiment said Het$^2$ or Het$^3$ being selected from the group consisting of

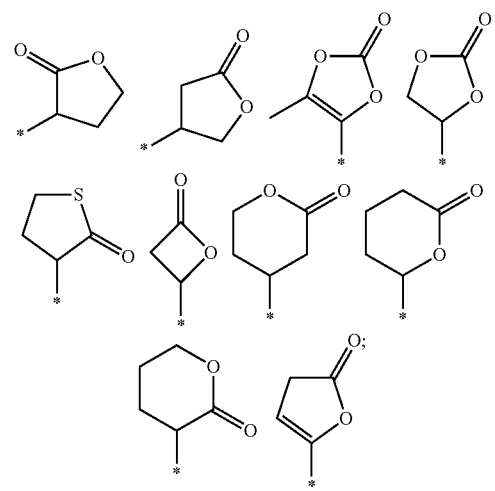

Het$^2$ or Het$^3$ are independently selected from the group comprising;

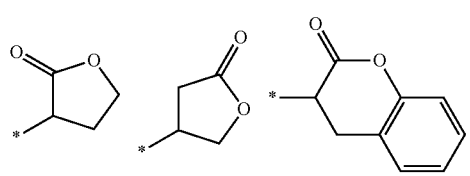

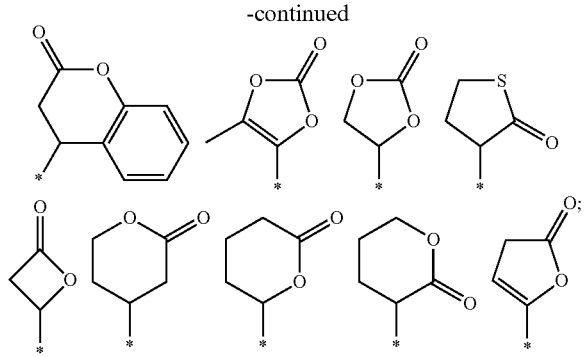

and

Those compounds of formula Ib; are particularly useful in the prevention and/or treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, and/or for preventing, treating and/or alleviating complications and/or symptoms associated therewith. It is accordingly an object of the present invention to provide said compounds for use in the treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, and/or for preventing, treating and/or alleviating complications and/or symptoms associated therewith. Alternatively, to provide a method for prevention and/or treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, said said method comprising administering to a subject in need thereof a therapeutic effective amount of a compound according to formula I; in particular a compound as defined hereinbefore.

In a further embodiment, the invention provides the use of a compound as defined hereinbefore or the use of a composition comprising said compound in the prevention and/or treatment of cardiovascular and vascular diseases: including but not limited to cerebrovascular contraction, reperfusion, hypoxia peripheral circulation disorder, myocardial hypertrophy, acute stroke, congestive heart failure, cardiovascular ischemia, heart disease, cardiac remodeling, angina, coronary vasospasm, cerebral vasospasm, restenosis, hypertension, pulmonary hypertension, pulmonary vasoconstriction, arteriosclerosis, atherosclerosis, aneurism, hemorrhage, Raynaud's disorder, thrombosis (including deep thrombosis) and platelet related diseases, and/or for preventing, treating and/or alleviating complications and/or symptoms associated therewith and/or alleviating complications and/or symptoms associated therewith.

In a further embodiment, the invention provides the use of a compound as defined hereinbefore or the use of a composition comprising said compound in the prevention and/or treatment of Throat, Nose and Ear diseases: including but not limited to sinus problems, hearing problems, toothache, tonsillitis, ulcer and rhinitis.

In a further embodiment, the invention provides the use of a compound as defined hereinbefore or the use of a composition comprising said compound in the prevention and/or treatment of skin diseases: including but not limited to hyperkeratosis, parakeratosis, hypergranulosis, acanthosis, dyskeratosis, spongiosis and ulceration.

In a further embodiment, the invention provides the use of a compound as defined hereinbefore or the use of a composition comprising said compound in the prevention and/or treatment of Intestinal diseases; including but not limited to inflammatory bowel disease (IBD), colitis, gastroenteritis, ileus, ileitis, appendicitis and Crohn's disease.

In yet another embodiment, the invention provides the use of a compound as defined hereinbefore or the use of a composition comprising said compound in the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis, and/or for preventing, treating and/or alleviating complications and/or symptoms and/or inflammatory responses associated therewith.

In another embodiment, the invention provides the use of a compound as defined hereinbefore or the use of a composition comprising said compound in the prevention, treatment and/or management of neurological and CNS disorders: including but not limited to stroke, meningitis, convulsions, brain or spinal cord injury and inflammatory and demyelinating diseases such as Alzheimer's disease, multiple sclerosis and neuropathic pain. The present compounds are therefore suitable for preventing neurodegeneration and stimulating neurogeneration in various neurological disorders, and/or for preventing, treating and/or alleviating complications and/or symptoms associated therewith.

In another embodiment, the invention provides the use of a compound as defined hereinbefore or the use of a composition comprising said compound in the prevention and/or treatment of proliferative diseases: such as but not limited to cancer of the brain (gliomas), breast, colon, intestine, skin, head and neck, nerve, uterus, kidney, lung, liver, ovary, pancreas, prostate, or thyroid gland; Castleman disease; leukemia; sarcoma; lymphoma; malignoma; and melanoma; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of kidney diseases: including but not limited to renal fibrosis or renal dysfunction; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety.

In another embodiment, the invention provides the use of a compound as defined hereinbefore or the use of a composition comprising said compound in the prevention and/or treatment of blood diseases: including but not limited to sepsis, eosinophilia, endotoxemia; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of bone diseases: including but not limited to osteoporosis and osteoarthritis; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of diabetes: including but not limited to hyperglycemia and type 1 diabetes; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of diseases and disorders such as benign prostatic hyperplasia, transplant rejection, liver disease, systemic lupus erythmatosis, spasm, hypertension, chronic obstructive bladder disease, premature birth, infection, allergy, obesity, pancreatic disease and AIDS, and/or for preventing, treating and/or alleviating complications and/or symptoms associated therewith.

In a preferred embodiment the present invention provides the use of a compound as defined hereinbefore or the use of a composition comprising said compound in the prevention and/or treatment of glaucoma, asthma, sexual dysfunction or COPD.

The present invention further provides a compound as defined hereinbefore or a composition comprising said compound for use in the prevention and/or treatment of at least one disease or disorder selected from the group comprising eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupus erythematosus, spasm, hypertension, chronic obstructive bladder disease, premature birth, infection, allergy, obesity, pancreatic disease and AIDS.

In a preferred embodiment, the invention provides a compound as defined hereinbefore or a composition comprising said compound for use in the prevention and/or treatment of eyes diseases including but not limited to retinopathy, optic neuropathy, glaucoma and degenerative retinal diseases such as macular degeneration, retinitis pigmentosa and inflammatory eye diseases, and/or for preventing, treating and/or alleviating complications and/or symptoms associated therewith.

In another preferred embodiment, the invention provides a compound as defined hereinbefore or a composition comprising said compound for use in the prevention and/or treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, and/or for preventing, treating and/or alleviating complications and/or symptoms associated therewith.

In a further embodiment, the invention provides a compound as defined hereinbefore or a composition comprising said compound for use in the prevention and/or treatment of cardiovascular and vascular diseases: including but not limited to cerebrovascular contraction, reperfusion, hypoxia peripheral circulation disorder, myocardial hypertrophyacute stroke, congestive heart failure, cardiovascular ischemia, heart disease, cardiac remodeling, angina, coronary vasospasm, cerebral vasospasm, restenosis, hypertension, pulmonary hypertension, pulmonary vasoconstriction, arteriosclerosis, atherosclerosis, aneurism, hemorrhage, Raynaud's disorder, thrombosis (including deep thrombosis) and platelet related diseases, and/or for preventing, treating and/or alleviating complications and/or symptoms associated therewith and/or alleviating complications and/or symptoms associated therewith.

In yet another embodiment, the invention provides a compound as defined hereinbefore or a composition comprising said compound for use in the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis, and/or for preventing, treating and/or alleviating complications and/or symptoms and/or inflammatory responses associated therewith.

In another embodiment, the invention provides a compound as defined hereinbefore or a composition comprising said compound for use in the prevention and/or treatment of neurological and CNS disorders: including but not limited to stroke, meningitis, convulsions, brain or spinal cord injury and inflammatory and demyelinating diseases such as Alzheimer's disease, multiple sclerosis and neuropathic pain. The present compounds are therefore suitable for preventing neurodegeneration and stimulating neurogeneration in various neurological disorders, and/or for preventing, treating and/or alleviating complications and/or symptoms associated therewith.

In another embodiment, the invention provides a compound as defined hereinbefore or a composition comprising said compound for use in the prevention and/or treatment of proliferative diseases: such as but not limited to cancer of the brain (gliomas), breast, colon, intestine, skin, head and neck, nerve, uterus, kidney, lung, liver, ovary, pancreas, prostate, or thyroid gland; Castleman disease; leukemia; sarcoma; lymphoma; malignoma; and melanoma; and/or for preventing, treating and/or alleviating complications and/or symptoms and/or inflammatory responses associated therewith.

In another embodiment, the invention provides a compound as defined hereinbefore or a composition comprising said compound for use in the prevention and/or treatment of kidney diseases: including but not limited to renal fibrosis or renal dysfunction; and/or for preventing, treating and/or alleviating complications and/or symptoms and/or inflammatory responses associated therewith.

In another embodiment, the invention provides the use of a compound as defined hereinbefore or the use of a composition comprising said compound in the preparation of a medicament for the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety.

In another embodiment, the invention provides a compound as defined hereinbefore or a composition comprising said compound for use in the prevention and/or treatment of blood diseases: including but not limited to sepsis, eosinophilia, endotoxemia; and/or for preventing, treating and/or alleviating complications and/or symptoms and/or inflammatory responses associated therewith.

In another embodiment, the invention provides a compound as defined hereinbefore or a composition comprising said compound for use in the prevention and/or treatment of bone diseases: including but not limited to osteoporosis and osteoarthritis; and/or for preventing, treating and/or alleviating complications and/or symptoms and/or inflammatory responses associated therewith.

In another embodiment, the invention provides a compound as defined hereinbefore or a composition comprising said compound for use in the prevention and/or treatment of diabetes: including but not limited to hyperglycemia and type 1 diabetes; and/or for preventing, treating and/or alleviating complications and/or symptoms and/or inflammatory responses associated therewith.

In another embodiment, the invention provides a compound as defined hereinbefore or a composition comprising said compound for use in the prevention and/or treatment of diseases and disorders such as benign prostatic hyperplasia, transplant rejection, liver disease, systemic lupus erythematosus, spasm, hypertension, chronic obstructive bladder disease, premature birth, infection, allergy, obesity, pancreatic disease and AIDS, and/or for preventing, treating and/or alleviating complications and/or symptoms associated therewith.

In a preferred embodiment the present invention provides a compound as defined hereinbefore or a composition comprising said compound for use in the prevention and/or treatment of glaucoma, asthma, sexual dysfunction or COPD.

Method of Treatment

The present invention further provides a method for the prevention and/or treatment of at least one disease or disorder selected from the group comprising eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia; transplant rejection; liver disease; systemic lupus erythematosus; spasm; hypertension; chronic obstructive bladder disease; premature birth; infection; allergy; obesity; pancreatic disease; and AIDS; said method comprising administering to a subject in need thereof a therapeutic effective amount of a compound or a composition as defined herein.

In a preferred embodiment, the invention provides a method for the prevention and/or treatment of eye diseases including but not limited to retinopathy, optic neuropathy, glaucoma and degenerative retinal diseases such as macular degeneration, retinitis pigmentosa and inflammatory eye diseases; said method comprising administering to a subject in need thereof a therapeutic effective amount of a compound or a composition as defined herein.

In another preferred embodiment, the invention provides a method for the prevention and/or treatment of airway diseases including but not limited to pulmonary fibrosis, emphysema, chronic bronchitis, asthma, fibrosis, pneumonia, cystic fibrosis, chronic obstructive pulmonary disease (COPD) bronchitis, rhinitis, and respiratory distress syndrome; said method comprising administering to a subject in need thereof a therapeutic effective amount of a compound or a composition as defined herein.

In another embodiment, the invention provides a method for the prevention and/or treatment of cardiovascular and vascular diseases: including but not limited to cerebrovascular contraction, reperfusion, hypoxia peripheral circulation disorder, myocardial hypertrophyacute stroke, congestive heart failure, cardiovascular ischemia, heart disease, cardiac remodeling, angina, coronary vasospasm, cerebral vasospasm, restenosis, hypertension, pulmonary hypertension, pulmonary vasoconstriction, arteriosclerosis, atherosclerosis, aneurism, hemorrhage, Raynaud's disorder, thrombosis (including deep thrombosis) and platelet related diseases; said method comprising administering to a subject in need thereof a therapeutic effective amount of a compound or a composition as defined herein.

In another embodiment, the invention provides a method for the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis; said method comprising administering to a subject in need thereof a therapeutic effective amount of a compound or a composition as defined herein.

In another embodiment, the invention provides a method for the prevention and/or treatment of neurological and CNS disorders: including but not limited to stroke, meningitis, convulsions, brain or spinal cord injury and inflammatory and demyelinating diseases such as Alzheimer's disease, multiple sclerosis and neuropathic pain. The present compounds are therefore suitable for preventing neurodegeneration and stimulating neurogeneration in various neurological disorders; said method comprising administering to a subject in need thereof a therapeutic effective amount of a compound or a composition as defined herein.

In another embodiment, the invention provides a method for the prevention and/or treatment of proliferative diseases: such as but not limited to cancer of the brain (gliomas), breast, colon, intestine, skin, head and neck, nerve, uterus, kidney, lung, liver, ovary, pancreas, prostate, or thyroid gland; Castleman disease; leukemia; sarcoma; lymphoma; malignoma; and melanoma; said method comprising administering to a subject in need thereof a therapeutic effective amount of a compound or a composition as defined herein.

In another embodiment, the invention provides a method for the prevention and/or treatment of kidney diseases: including but not limited to renal fibrosis or renal dysfunction; said method comprising administering to a subject in need thereof a therapeutic effective amount of a compound or a composition as defined herein.

In another embodiment, the invention provides a method for the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety; said method comprising administering to a subject in need thereof a therapeutic effective amount of a compound or a composition as defined herein.

In another embodiment, the invention provides a method for the prevention and/or treatment of blood diseases: including but not limited to sepsis, eosinophilia, endotoxemia; said method comprising administering to a subject in need thereof a therapeutic effective amount of a compound or a composition as defined herein.

In another embodiment, the invention provides a method for the prevention and/or treatment of bone diseases: including but not limited to osteoporosis and osteoarthritis; said method comprising administering to a subject in need thereof a therapeutic effective amount of a compound or a composition as defined herein.

In another embodiment, the invention provides a method for the prevention and/or treatment of diabetes: including but not limited to hyperglycemia and type 1 diabetes; said method comprising administering to a subject in need thereof a therapeutic effective amount of a compound or a composition as defined herein.

In another embodiment, the invention provides a method for the prevention and/or treatment of diseases and disorders such as benign prostatic hyperplasia, transplant rejection, liver disease, systemic lupus erythematosus, spasm, hypertension, chronic obstructive bladder disease, premature birth, infection, allergy, obesity, pancreatic disease and AIDS; said method comprising administering to a subject in need thereof a therapeutic effective amount of a compound or a composition as defined herein.

In a preferred embodiment, the invention provides a method for the prevention and/or treatment of glaucoma, asthma, sexual dysfunction or COPD; said method comprising administering to a subject in need thereof a therapeutic effective amount of a compound or a composition as defined herein.

In the invention, particular preference is given to compounds of Formula I or any subgroup thereof that in the inhibition assay for ROCK described below inhibit ROCK with an $IC_{50}$ value of less than 10 μM, preferably less than 1 μM.

Said inhibition may be effected in vitro and/or in vivo, and when effected in vivo, is preferably effected in a selective manner, as defined above.

The term "ROCK-mediated condition" or "disease", as used herein, means any disease or other deleterious condition in which is known to play a role. The term "ROCK-mediated condition" or "disease" also means those diseases or conditions that are alleviated by treatment with a ROCK inhibitor. Accordingly, another embodiment of the present invention relates to treating or lessening the severity of one or more diseases in which ROCK is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

Particular reference is made to the compositions, formulations (and carriers, excipients, diluents, etc. for use therein), routes of administration etc., which are known per se for analogous pyridinocarboxamides, such as those described in U.S. Pat. No. 4,997,834 and EP-A-0 370 498.

For the treatment of pain, the compounds of the invention may be used locally. For local administration, the compounds may advantageously be used in the form of a spray, ointment or transdermal patch or another suitable form for topical, transdermal and/or intradermal administration.

For ophthalmic application, solutions, gels, tablets and the like are often prepared using a physiological saline solution, gel or excipient as a major vehicle. Ophthalmic formulations should preferably be prepared at a comfortable pH with an appropriate buffer system.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the Formula I-XXIV or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

A. Physicochemical Properties of the Compounds

A.1. Compound Purity

Unless indicated otherwise, the purity of the compounds was confirmed by liquid chromatography/mass spectrometry (LC/MS), as follows:

HPLC system: Waters 2690 with photodiode array detector Waters 996; Column: C18; Gradient: solvent A ($H_2O$/formic acid 26.5 nM) 0%, to solvent B ($CH_3CN$/formic acid 17 nM) 80% in 3 min. Flow: 2.75 ml/min.

Mass spectrometer: Micromass Platform LC. Ionization: electrospray (polarity: negative and positive).

A.2. Attribution of the Configuration:

The Cahn-Ingold-Prelog system was used to attribute the absolute configuration of chiral center, in which the four groups on an asymmetric carbon are ranked to a set of sequences rules. Reference is made to Cahn; Ingold; Prelog Angew. *Chem. Int Ed. Engl.* 1966, 5, 385-415.

A.3. Stereochemistry:

It is known by those skilled in the art that specific enantiomers (or diastereoisomers) can be obtained by different methods such as, but not limited to chiral resolution (for example, salts formed with optically active acids or bases may be used to form diastereoisomeric salts that can facilitate the separation of optically active isomers of the compounds of Formula I or any subgroup thereof), assymetric synthesis or preparative chiral chromatography (using different column such as Chiralcel OD-H (tris-3,5-dimethylphenylcarbamate, 46×250 or 100×250 mm, 5 μm), Chiralcel OJ (tris-methylbenzoate, 46×250 or 100×250 mm, 5 μm), Chiralpak AD (tris-3,5-dimethylphenylcarbamate, 46×250 mm, 10 μm) and Chiralpak AS (tris-(S)-1-phenylethylcarbamate, 46×250 mm, 10 μm) from Chiral Technologies Europe (Illkirch, France)). Whenever it is convenient, stereoisomers can be obtained starting from commercial materials with known configuration (such compounds include amino acid for instance).

A.4. Name of the Molecules

The software MDL ISIS™/Draw 2.3 was used to assign the name of the molecules.

B. Compound Synthesis

B.1. Intermediates

The compounds of the invention may be prepared by methods well known to those skilled in the art, and as described in the synthetic and experimental procedures shown below.

For example, intermediates C can be obtained according to, but not limited to the following general sequence (amide formation followed by suzuki coupling):

PG represents a suitable protecting group such as groups described by T. Greene and P. Wuts, in "Greene's Protective Group in Organic Chemistry" (4th edition, John Wiley & Sons Inc).

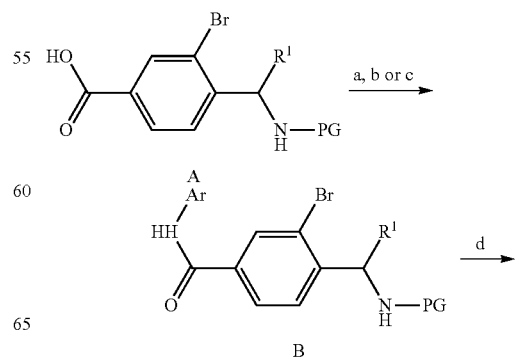

B

-continued

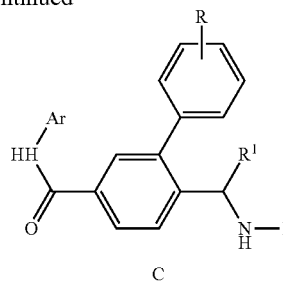

C (a) ArNH₂, TBTU, HOBt, DIEA, DMF, rt or ArNH₂, DCC, HOBt, DIEA, DMF/DCM, rt;
(b) Ghosez's reagent [Me₂C═C(Cl)NMe₂], THF, rt, followed by ArNH₂, Py
(c) ArNH₂, CuI, Cs₂CO₃, DMEDA, dioxane, 130° C., 16 h;
(d) 2M Na₂CO₃ (aq), Pd(PPh₃)₄, toluene or DME, ethanol, N₂, MW, 130° C.

General Procedures for Preparation of Amides

Protocol A.

To a solution of the corresponding carboxilyc acid (1 mmol) in DMF (10 ml) were added DIEA (3 mmol, 3 eq.), TBTU (1.3 mmol, 1.3 eq.) and HOBt (0.3 mmol, 0.3 eq.). The reaction mixture was stirred at rt for 5-10 min followed by addition of the corresponding amine (1.1 eq.). The reaction mixture was stirred for 16 to 24 hours, then diluted with ethyl acetate (100 mL), washed with 0.1 M HCl (50 mL) and saturated sodium carbonate (50 mL). The organic phase was dried over MgSO₄ and the solvent was removed in vaccuo.

Alternative protocol: To a solution of the corresponding carboxylic acid (1 eq) in a mixture DMF/DCM (0.25 M) were successively added DCC (1 eq), HOBt (1 eq) and DIEA (3 eq). The solution was stirred at RT for 30 minutes before the addition of the corresponding amine (1 eq). The reaction mixture was stirred at RT for 1 hour to 3 days. The solvent removed in vacuo. The residue was partitioned between DCM and water. The product was extracted with DCM. The organic layer was separated, washed with 2M sodium carbonate (or 1N NaOH), 1N HCl, brine, dried over MgSO₄, and evaporated.

Alternative protocol: A mixture of the corresponding carboxylic acid (200 mg, 1.0 eq) and amine (2.0 eq) in CH₃CN (4 ml) was added HOBT (0.4 eq) and EDCI (about 120 mg, 1.5 eq). The reaction mixture was stirred at 30° C. for 16 hrs. LC-MS showed the reaction was complete. Then the solvent was concentrated to dryness to give crude product, which was used directly for next step without purification.

The crude product was dissolved in DCM/TFA=7:1 (4 ml). The reaction mixture was stirred at 30° C. for 16 hrs. LC-MS showed the reaction was complete. Then the reaction mixture was concentrated and the crude product was purified by prep HPLC to give the final product.

Protocol B.

To a solution of the corresponding carboxylic acid (5 mmol) in dry THF (10 ml) was added Ghosez reagent (10 mmol, 2 eq.). The reaction mixture was stirred at rt for 2.5 hours and the solvent was removed in vaccuo. The residue was dissolved in dry pyridine and cooled to 0° C. followed by addition of the corresponding amine (5.5 mmol, 1.1 eq.). The reaction mixture was stirred at rt for 1 hour. The pyridine was removed by co-evaporation with toluene, the residue was dissolved in EtOAc (100 mL) and washed with 1M NaOH (50 mL), water (50 mL) and brine (50 mL). The organic phase was dried over MgSO₄ and the solvent was removed in vaccuo Protocol C.

A solution of the corresponding carboxylic acid (1 mmol) in dioxane (2 ml) was degassed by bubbling nitrogen through the solution. Copper (I)-iodide (0.25 mmol, 0.25 eq), Cs₂CO₃ (2.5 mmol, 2.5 eq.), the corresponding amine (1.2 mmol, 1.2 eq.) and N,N'-dimethyl-ethane-1,2-diamine (0.5 mmol, 0.5 eq.) were added. The reaction mixture was stirred in a closed vial at 130° C. for 24 hours. The reaction mixture was filtered over Celite and the Celite was washed with EtOAc (200 mL). The filtrate was washed with 1M sodium bicarbonate (100 mL), 0.1M HCl (100 mL), water (100 mL) and brine (100 mL). The organic layer was dried over MgSO₄ and the solvent was removed in vaccuo.

Protocol D. General Procedure for Suzuki Reaction

A MW vessel (Biotage, 20 mL) was charged with an appropriate boronic acid (3 mmol, 2 eq), the corresponding phenyl bromide (1.5 mmol, 1 eq), toluene or DME (3 mL), ethanol (3 mL) and 2M sodium carbonate solution (3 mL, 6 mmol, 4 eq). The reaction vessel was then flushed with nitrogen before adding tetrakis(triphenyl phosphine) palladium (0) catalyst (4 mol %). The reaction vessel was again flushed with nitrogen before sealing and irradiating in MW at 130° C. for 1-1.5 h. The reaction mixture residue was then cooled down and filtered through Celite. The residue was washed with ethyl acetate (200 mL) and methanol (100 mL) The solvent was removed in vacuo and the residue was taken up in DCM. The precipitate was filtered, washed with DCM and dried. The compound was used as such or was purified by flash chromatography (silicagel, DCM/MeOH gradient).

Intermediate 1: 3-Bromo-4-(1-tert-butoxycarbonylamino-ethyl)-benzoic acid

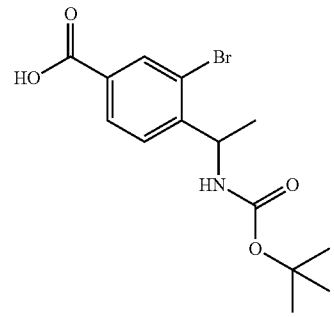 [SMILES: CC(NC(=O)OC(C)(C)C)c1ccc(C(=O)O)cc1Br]

To a solution of 4-acetyl-3-bromo-benzoic acid (40 to 80 mmol) in EtOH (100 to 200 ml) was added DIEA (1.6 eq.) and hydroxylamine hydrochloride (1.6 eq.). The reaction mixture was stirred under reflux conditions for 1 hour. The reaction mixture was cooled to room temperature and the solvent was removed under reduced pressure. The residue was taken up in water and a 20% KHSO₄ solution. The precipitate was filtered, washed with water and dried.

To a solution of 3-bromo-4-[1-(hydroximino)-ethyl]-benzoic acid (10 to 50 mmol) in acetic acid (30 to 300 ml) was added activated zinc (5 to 10 eq.). The reaction mixture was stirred at room temperature for 10 minutes or up to 3.5 hours. The reaction mixture was filtered and the precipitate was washed with acetic acid. The solvent of the filtrate was removed under reduced pressure.

The crude 4-(1-amino-ethyl)-3-bromo-benzoic acid (15323 to 30727 μmol) was suspended in a mixture of THF/1M Na₂CO₃: 1/1 (100 ml) or a mixture of acetone/1M Na₂CO₃: 1/1 (100 ml) or a mixture of acetone/2M Na₂CO₃: 8/2 (100 ml) and (Boc)₂O (1.5 eq) was added. The reaction mixture was stirred at RT for 1 to 2 hours. The organic solvent was removed under reduced pressure or diethylether was added and the two layers were separated or the reaction mixture was filtered and the organic solvent was removed under reduced pressure. The aqueous residue was diluted with citric acid or with a 20% KHSO$_4$ solution and extracted with EtOAc. The combined organic layers were washed with brine, dried over MgSO$_4$ and the solvent was removed under reduced pressure. The compound was when needed purified by column chromatography (silicagel, DCM/MeOH gradient).

Intermediate 2: {1-[2-Bromo-4-(pyridine-4-ylcarbamoyl)-phenyl]ethyl}-carbamic acid tert-butyl ester

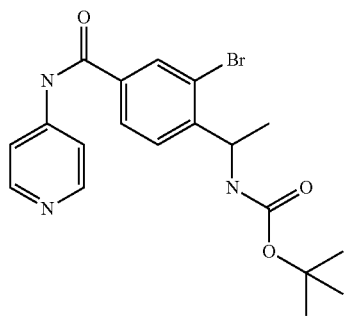 [SMILES: CC(NC(=O)OC(C)(C)C)c1ccc(C(=O)Nc2ccncc2)cc1Br]

To a solution of 3-bromo-4-(1-tert-butoxycarbonylaminoethyl)-benzoic acid (7496 to 61011 μmol) in DMF (10 to 30 ml) were added DIEA (2 eq.), TBTU (1.3 eq.) and HOBt (0.3 eq.). The reaction mixture was stirred at RT for 5 minutes. 4-Aminopyridine (1.5 eq) was added and the reaction mixture was stirred at RT for 2.5 hours up to overnight. When there was still starting material observed, more DIEA (0.39 eq), TBTU (0.25 eq), HOBt (0.06 eq) and 4-aminopyridine (0.28 eq) were added and the reaction mixture was stirred at RT for another 2 hours. The reaction mixture was diluted with EtOAc, washed with 0.1 M HCl and saturated Na$_2$CO$_3$ or with saturated NaHCO$_3$. The organic layer was dried over MgSO$_4$ and the solvent was removed under reduced pressure. The compound was purified by column chromatography (silicagel, DCM/MeOH gradient).

Intermediate 3: 2'-(1-tert-Butoxycarbonylaminoethyl)-5'-(pyridin-4-ylcarbamoyl)-biphenyl-3-carboxylic acid

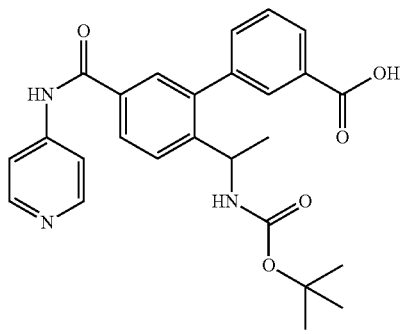 [SMILES: CC(NC(=O)OC(C)(C)C)c1ccc(C(=O)Nc2ccncc2)cc1-c1cccc(C(=O)O)c1]

Method 1: To a solution of {1-[2-bromo-4-(pyridine-4-ylcarbamoyl)-phenyl]-ethyl}-carbamic acid tert-butyl ester (2 to 3 mmol) and 3-carboxyphenylboronic acid (1.2 eq.) in a mixture of DME/EtOH/water: 2/1/1 (10 ml) was added Na$_2$CO$_3$ (4 eq) and Pd tetrakis (0.05 eq). The reaction mixture was heated in the microwave at 135° C. for 30 min. The solvents were removed under reduced pressure. The residue was diluted with MeOH and filtered over celite. The celite residue was washed with MeOH. The solvent was removed under reduced pressure and the residue was taken up in DCM. The precipitate was filtered, washed with DCM and dried. The compound was purified by semi-preperative LC-MS. Or the residue was diluted with DCM/MeOH (3/2) and activated charcoal was added to the reaction mixture. The mixture was stirred at RT for 10 minutes and filtered over silicagel. The residue was washed with DCM/MeOH (8/2) followed by MeOH. The solvent was then removed under reduced pressure.

Method 2: To a solution of {1-[2-bromo-4-(pyridine-4-ylcarbamoyl)-phenyl]-ethyl}-carbamic acid tert-butyl ester (6912 μmol) and 3-carboxyphenylboronic acid (1.0 eq.) in a mixture of toluene/EtOH: 5/3 (32 ml) was added a solution of Na$_2$CO$_3$ (3 eq) in water (8 ml) and Pd tetrakis (0.03 eq). The reaction mixture was heated under reflux conditions for 3 hours. More 3-carboxyphenylboronic acid (0.35 eq.) and Pd tetrakis (0.015 eq) were added and the mixture was again heated under reflux conditions for 3 hours. The reaction mixture was cooled to RT and filtered over celite. The celite residue was washed with EtOAc and MeOH. The solvents were removed under reduced pressure and the compound was purified by column chromatography (silicagel, DCM/MeOH gradient).

Intermediate 4: [2'-(1-tert-Butoxycarbonylaminoethyl)-5'-(pyridin-4-ylcarbamoyl)-biphenyl-3-yl]-acetic acid

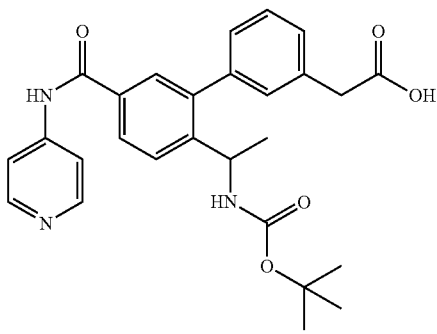 [SMILES: CC(NC(=O)OC(C)(C)C)c1ccc(C(=O)Nc2ccncc2)cc1-c1cccc(CC(=O)O)c1]

To a solution of {1-[2-bromo-4-(pyridine-4-ylcarbamoyl)-phenyl]ethyl}-carbamic acid tert-butyl ester (1951 μmol) in a mixture of DME/EtOH/2N Na$_2$CO$_3$: 1/1/1 (10 ml) were added 3-carboxymethylphenylboronic acid (1.5 eq) and Pd tetrakis (0.05 eq). The reaction mixture was heated in the microwave at 160° C. for 15 minutes. The reaction mixture was cooled to RT, filtered over celite and washed with EtOAc and MeOH. The solvents were removed under reduced pressure. The compound was purified by column chromatography (silicagel, DCM/MeOH gradient).

Intermediate 5: 3-[2'-(1-tert-Butoxycarbonylamino-ethyl)-5'-(pyridin-4-ylcarbamoyl)-biphenyl-3-yl]-propionic acid

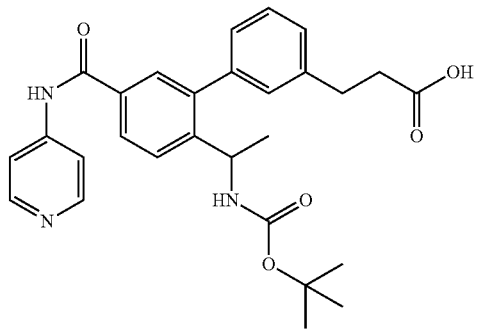 [SMILES: CC(NC(=O)OC(C)(C)C)c1ccc(C(=O)Nc2ccncc2)cc1-c1cccc(CCC(=O)O)c1]

To a solution of {1-[2-bromo-4-(pyridine-4-ylcarbamoyl)-phenyl]-ethyl}-carbamic acid tert-butyl ester (3122 μmol) in a mixture of DME/EtOH/2N $Na_2CO_3$: 1/1/1 (20 ml) were added 3-carboxyethylphenylboronic acid (1.5 eq) and Pd tetrakis (0.05 eq). The reaction mixture was heated in the microwave at 160° C. for 15 minutes. The reaction mixture was cooled to RT, filtered over celite and washed with EtOAc and MeOH. The solvents were removed under reduced pressure. The compound was purified by column chromatography (silicagel, DCM/MeOH gradient).

Intermediate 6: {1-[3'-Hydroxy-5-(pyridin-4-ylcarbamoyl)-biphenyl-2-yl]-ethyl}-carbamic acid tert-butyl ester

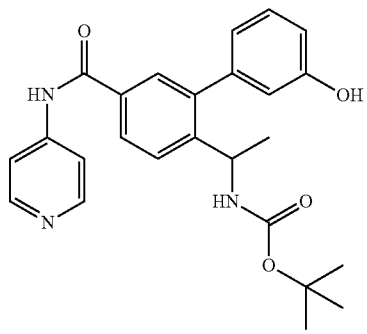 [SMILES: CC(NC(=O)OC(C)(C)C)c1ccc(C(=O)Nc2ccncc2)cc1-c1cccc(O)c1]

To a solution of {1-[2-bromo-4-(pyridine-4-ylcarbamoyl)-phenyl]-ethyl}-carbamic acid tert-butyl ester (2087 μmol) and 3-hydroxyphenylboronic acid (1.55 eq) in a mixture of DME/EtOH: 1/1 (8 ml) were added $Na_2CO_3$ (4 eq) and Pd tetrakis (0.05 eq.). The reaction mixture was flushed with Ar and was heated in the microwave at 130° C. for 1.5 hours. The reaction mixture was cooled to RT, diluted with 1N $NaHCO_3$ and extracted with EtOAc. The organic layer was extracted with 1N $NaHCO_3$ and the combined aqueous layers were acidified with citric acid and 1N HCl. The aqueous layer was extracted with EtOAc, the organic layer was dried over $MgSO_4$ and the solvent was removed under reduced pressure. The compound was purified by recrystallization from EtOAc.

Intermediate 7: [2'-(1-tert-Butoxycarbonylamino-ethyl)-5'-(pyridin-4-ylcarbamoyl)-biphenyl-3-yloxy]-acetic acid

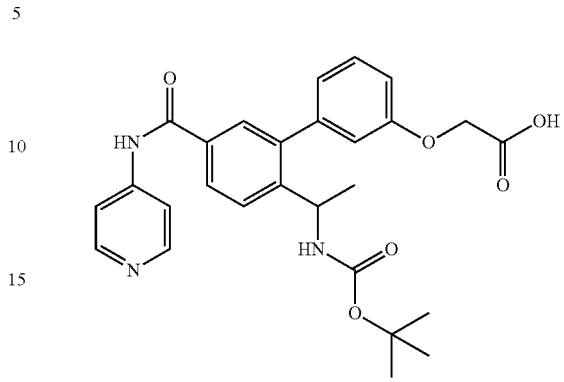

To a solution of {1-[2-Bromo-4-(pyridine-4-ylcarbamoyl)-phenyl]-ethyl}-carbamic acid tert-butyl ester (0.48 g) in a mixture of toluene/ethanol: 5/3 (12 ml) were added 3-phenoxy-acetic acid benzyl ester boronic acid (2 eq.), a solution of $Na_2CO_3$ (4 eq.) in water (4 ml) and Pd tetrakis (0.06 eq.). The reaction mixture was heated under reflux conditions for 2 hours. The reaction mixture was cooled to RT and filtered over celite. The celite residue was washed with EtOAc and EtOH. The solvent was removed under reduced pressure and the residue was taken up in DCM. The precipitate was filtered, washed with DCM and dried. The compound was purified by column chromatography (silicagel, DCM/MeOH gradient).

Intermediate 8: {1-[2-Bromo-4-(3-fluoro-pyridine-4-ylcarbamoyl)-phenyl]-ethyl}-carbamic acid tert-butyl ester

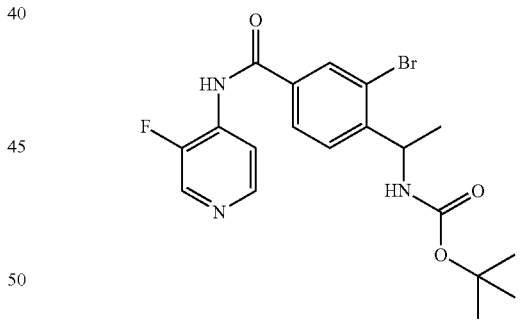

To a solution of 3-bromo-4-(1-tert-butoxycarbonylamino-ethyl)-benzoic acid (8352 μmol) in dry THF (20 ml) was added Ghosez reagent (2 eq.). The mixture was stirred at RT for 2 hours. The solvent was removed under reduced pressure. The residue was dissolved in dry pyridine (20 ml) and 3-fluoro-pyridin-4-ylamine (1.2 eq) was added. The reaction mixture was stirred at RT for 2.5 hours. The pyridine was removed under reduced pressure. The residue was dissolved in 1N $Na_2CO_3$ and extracted with EtOAc. The combined organic layers were washed with 1N $NaHCO_3$, citric acid and water. The organic layer was dried over $MgSO_4$ and the solvent was removed under reduced pressure. The compound was purified by column chromatography (silicagel, DCM/MeOH gradient).

Intermediate 9: 2'-(1-tert-Butoxycarbonylamino-ethyl)-5'-(3-fluoro-pyridin-4-ylcarbamoyl)-biphenyl-3-carboxylic acid

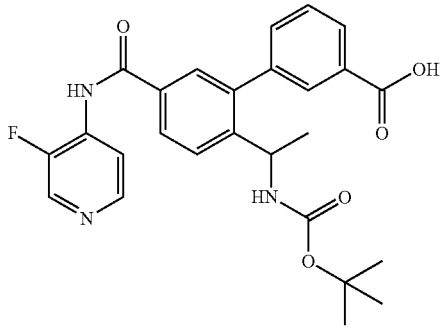 [SMILES: CC(NC(=O)OC(C)(C)C)c1ccc(C(=O)Nc2ccncc2F)cc1-c1cccc(C(=O)O)c1]

To a solution of {1-[2-bromo-4-(3-fluoro-pyridin-4-ylcarbamoyl)-phenyl]-ethyl}-carbamicacid tert-butyl ester (2841 µmol) and 3-carboxyphenylboronic acid (1.5 eq.) in a mixture of DME/EtOH/water: 1/1/1 (10 ml) was added $Na_2CO_3$ (4 eq) and Pd tetrakis (0.05 eq). The reaction mixture was heated in the microwave at 130° C. for 1.5 hours. The reaction mixture was diluted with water and citric acid (to acidic pH) and extracted with EtOAc. The combined organic layers were dried over $MgSO_4$ and the solvent was removed under reduced pressure. The compound was purified by column chromatography (silicagel, DCM/MeOH gradient).

Intermediate 10: [2'(1-tert-Butoxycarbonylamino-ethyl)-5'-(3-fluoro-pyridin-4-ylcarbamoyl)-biphenyl-3-yloxy]-acetic acid

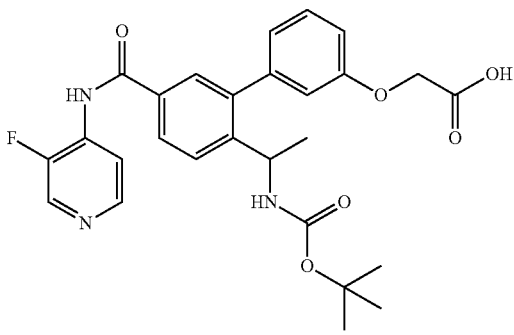 [SMILES: CC(NC(=O)OC(C)(C)C)c1ccc(C(=O)Nc2ccncc2F)cc1-c1cccc(OCC(=O)O)c1]

To a solution of {1-[2-bromo-4-(3-fluoro-pyridin-4-ylcarbamoyl)-phenyl]-ethyl}-carbamic acid tert-butyl ester (3400 to 3650 µmol) and the 3-phenoxy-acetic acid benzyl ester boronic acid (1 eq) in DMEwater: 9/1 (15 ml) were added $K_3PO_4$ (4 eq.) and Pd tetrakis (0.05 eq.). The reaction mixture was heated in the microwave at 130° C. for 30 minutes. Activated charcoal was added to the reaction mixture and the mixture was filtered over celite. The residue was washed with EtOAc and water. The aqueous layer was separated and extracted with EtOAc. The combined organic layers were washed with brine, dried over $MgSO_4$ and the solvent was removed under reduced pressure. The compound was purified by column chromatography (silicagel, cyclohexane/acetone gradient).

To a solution of [2'-(1-tert-butoxycarbonylamino-ethyl)-5'-(3-fluoro-pyridin-4-ylcarbamoyl)-phenyl]-biphenyl-3-yloxy]-acetic acid benzyl ester (2 mmol) in THF (25 ml) was added Pd/C (0.5 eq). The reaction mixture was flushed with hydrogen. A solution of cyclohexadiene in THF (5 ml) was added dropwise to the reaction mixture. The mixture was stirred at 55° C. for 24 hours under hydrogen atmosphere. Celite was added and the suspension was stirred at RT for 20 minutes. The suspension was filtered and the residue was washed with THF (50 ml). The solvent was removed under reduced pressure.

Intermediate 11: {1-[3'-Amino-5-(pyridin-4-ylcarbamoyl)-biphenyl-2-yl]-ethyl}-carbamic acid tert-butyl ester

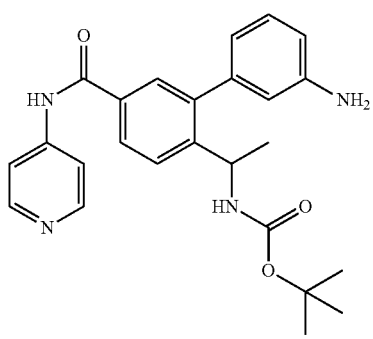 [SMILES: CC(NC(=O)OC(C)(C)C)c1ccc(C(=O)Nc2ccncc2)cc1-c1cccc(N)c1]

To a solution of {1[b-bromo-4-(pyridine-4-ylcarbamoyl)-phenyl]-ethyl}-carbamic acid tert-butyl ester (1428 µmol) and 3-aminophenylboronic acid (2 eq) in a mixture of DME/ethanol/1N $Na_2CO_3$: 1/1/1 (3 ml) was added Pd tetrakis (0.05 eq). The reaction mixture was heated in the microwave at 150° C. for 15 minutes. The reaction mixture was cooled to RT and diluted with water and extracted with EtOAc. The combined organic layers were washed with 0.5N HCl, dried over $MgSO_4$ and the solvent was removed under reduced pressure.

Intermediate 12: {1-[3'-Amino-5-(3-fluoro-pyridin-4-ylcarbamoyl)-biphenyl-2-yl]-ethyl}-carbamic acid tert-butyl ester

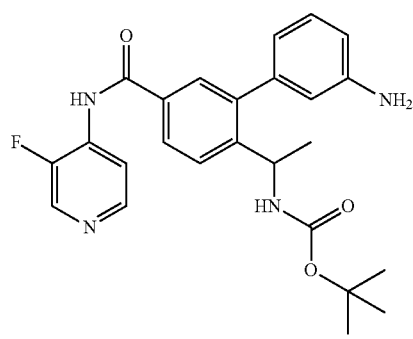 [SMILES: CC(NC(=O)OC(C)(C)C)c1ccc(C(=O)Nc2ccncc2F)cc1-c1cccc(N)c1]

To a solution of {1-[2-bromo-4-(3-fluoro-pyridine-4-ylcarbamoyl)-phenyl]-ethyl}-carbamic acid tert-butyl ester (1094 µmol) and 3-aminophenylboronic acid (2 eq) in a mixture of DME/ethanol/1N $Na_2CO_3$: 1/1/1 (10 ml) was added Pd tetrakis (0.05 eq). The reaction mixture was heated in the microwave at 130° C. for 1.5 hours. The reaction mixture was cooled to RT and diluted with water and citric acid and extracted with EtOAc. The combined organic layers were washed with water and brine. The organic layer was dried over MgSO₄ and the solvent was removed under reduced pressure. The compound was purified by column chromatography (silicagel, DCM/MeOH gradient).

Intermediate 13: 4-[2-(1-tert-Butoxycarbonylamino-ethyl)-5-(pyridin-4-ylcarbamoyl)-phenyl]-1H-pyrrole-2-carboxylic acid

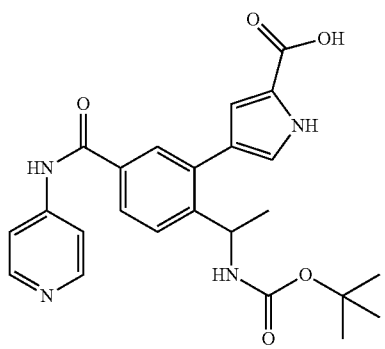 [SMILES: CC(NC(=O)OC(C)(C)C)c1ccc(C(=O)Nc2ccncc2)cc1-c1c[nH]c(C(=O)O)c1]

To a solution of {1-[2-bromo-4-(pyridine-4-ylcarbamoyl)-phenyl]-ethyl}-carbamic acid tert-butyl ester (809 μmol) and 1H-pyrrole-2-carboxylic acid methyl ester boronic acid (1.15 eq) in a mixture of DME/EtOH: 1/1 (0.8 ml) were added Na₂CO₃ (4 eq) and Pd tetrakis (0.05 eq.). The reaction mixture was flushed with Ar and was heated in the microwave at 130° C. for 35 minutes. The reaction mixture was cooled to RT, diluted with water and extracted with EtOAc. The solvent of the organic layer was removed under reduced pressure.

To a solution of 4-[2-(1-tert-Butoxycarbonylamino-ethyl)-5-(pyridin-4-ylcarbamoyl)-phenyl]-1H-pyrrole-2-carboxylic acid methyl ester (661 μmol) in THF (1.6 ml) and MeOH (1.6 ml) was added a 1N LiOH solution (1.6 ml). The reaction mixture was stirred at 40° C. for 1.5 hours. The reaction mixture was diluted with saturated NaHCO₃ and extracted with EtOAc. The aqueous layer is acidified with a 20% citric acid solution and extracted again with EtOAc. The combined organic layers were dried over MgSO₄ and the solvent was removed under reduced pressure.

Intermediate 14: 4-[2-(1-tert-Butoxycarbonylamino-ethyl)-5-(pyridin-4-ylcarbamoyl)-phenyl]-1H-indole-2-carboxylic acid

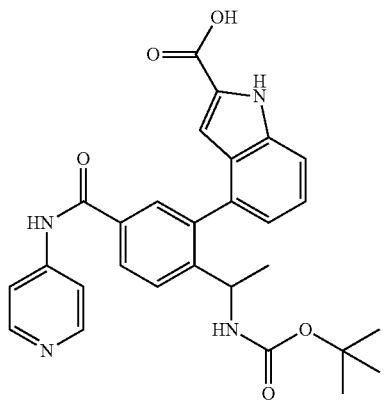 [SMILES: CC(NC(=O)OC(C)(C)C)c1ccc(C(=O)Nc2ccncc2)cc1-c1cccc2[nH]c(C(=O)O)cc12]

To a solution of {1-[2-bromo-4-(pyridine-4-ylcarbamoyl)-phenyl]ethyl}-carbamic acid tert-butyl ester (952 μmol) and 4-bromo-1H-indole-2-carboxylic acid methyl ester boronic acid (1.55 eq) in a mixture of DME/EtOH: 1/1 (8 ml) were added Na₂CO₃ (4 eq) and Pd tetrakis (0.05 eq.). The reaction mixture was flushed with Ar and was heated in the microwave at 130° C. for 35 minutes. The reaction mixture was cooled to RT, diluted with water and filtered. The residue was dried.

To a solution of 4-[2-(1-amino-ethyl)-5-(pyridin-4-ylcarbamoyl)-phenyl]-1H-indole-2-carboxylic acid methyl ester (600 μmol) in THF (2.4 ml) and MeOH (2.4 ml) was added a 1N LiOH solution (2.4 ml). The reaction mixture was stirred at 40° C. for 6 hours. The reaction mixture was diluted with 1N LiON and extracted with EtOAc. The aqueous layer is acidified with a 20% citric acid solution and extracted again with EtOAc. The combined organic layers were dried over MgSO₄ and the solvent was removed under reduced pressure.

Intermediate 15: 3-Bromo-4-(tert-butoxycarbonylamino-methyl)-benzoic acid

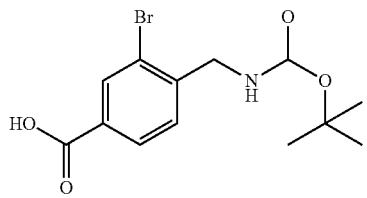 [SMILES: CC(C)(C)OC(O)NCc1ccc(C(=O)O)cc1Br]

To a suspension of 3-Bromo-4-methylbenzoic acid (300 g, 1.39 mol) in MeOH (3 L) was added H₂SO₄ (6 ml). The reaction mixture was stirred at 60° C. overnight. The reaction was cooled to room temperature, evaporated and the residue was dissolved in EtOAc (2 L), The EtOAc solution was washed with saturated NaHCO₃ (1 L), dried over MgSO₄ and concentrated to dryness to give the corresponding methyl ester as pale yellow oil (303 g, 95% yield).

A solution of the previous methyl ester (303 g, 0.98 mol, 1.0 eq) in anhydrous CCl₄ (1.5 L) was added to a solution of NBS (183.9 g, 1.03 mol, 1.05 eq) and AIBN (8 g, 0.049 mol, 0.05 eq) in anhydrous CCl₄ (1.5 L) at room temperature. The reaction mixture was refluxed for 16 hrs, cooled to room temperature, evaporated and the residue was dissolved in DCM (2.5 L). The DCM solution was washed with saturated NaHCO₃ (0.6 L), and H₂O (1 L*3). The organic layer was dried over MgSO₄ and concentrated to dryness to give crude 3-bromo-4-bromomethyl-benzoic acid methyl ester which was used for next step without further purification.

Boc₂NH (175 g, 0.925 mol, 1.0 eq) was added to a solution of t-BuOK (124.5 g, 1.11 mol 1.02 eq) in DMF (3 L), the resulting solution was stirred for 1 h at room temperature. Crude 3-bromo-4-bromomethyl-benzoic acid methyl ester was added to above reaction solution at room temperature and stirred overnight. The solvent was removed under vacuum and the residue was dissolved in DCM (500 ml). The DCM solution was washed with water (3×500 ml), dried over MgSO₄ and concentrated. The crude product was purified by column chromatography on silica gel using PE: EA=20:1 to give diBoc-4-Aminomethyl-3-bromo-benzoic acid methyl ester (290 g, 70% yield) as yellow solid To a solution of the previous di_Boc protected benzylamine (290 g, 0.652 mol, 1.0 eq) in DCM (2.9 L) was added TFA (92.8 g, 0.813 mol, 1.25 eq) dropwise at 0° C., the resulting mixture was stirred at room temperature for 4 hrs. 0.5 M NaHCO₃ was added to the mixture to adjust pH to 8. The reaction mixture was washed with water (3*500 ml), dried over MgSO₄ and concentrated by rotavapor to give 3-bromo-4-(tert-butoxycarbonylamino-methyl)-benzoic acid methyl ester (210 g, 93.5% yield) as yellow oil.

NaOH (48.8 g, 1.22 mol, 2.0 eq) in H₂O (1.26 L) was added to a solution of 3-bromo-4-(tert-butoxycarbonylamino-methyl)-benzoic acid methyl ester (210 g, 0.61 mol, 1.0 eq) in MeOH (1.26 L). The reaction mixture was stirred at 50° C. for 2 hrs. The reaction was cooled to room temperature and concentrated to half volume. The residue was acidified to pH 5 by adding 1M HCl solution. The resulting solid was collected and dried to give the title intermediate (200 g, 99.4% yield) as white solid.

Intermediate 16: [2-Bromo-4-(pyridin-4-ylcarbamoyl)-benzyl]-carbamic acid tert-butyl ester

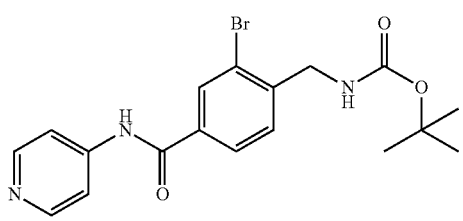 [SMILES: CC(C)(C)OC(=O)NCc1ccc(C(=O)Nc2ccncc2)cc1Br]

To a solution of Intermediate 15 (100 g, 0.303 mol, 1.0 eq) and 4-aminopyridine (28.5 g, 0.303 mol, 1.0 eq) in DMA (1 L) was added Et₃N (30.6 g, 0.303 mol, 1.0 eq), DMAP (3.7 g, 0.030 mol, 0.1 eq) and HATU (115.2 g, 0.303 mol, 1.0 eq). The reaction solution was stirred at 30° C. for 16 hrs. Solvent was evaporated under vacuum and the residue was solidified by adding DCM (600 ml) and H₂O (600 ml) to give the title compound (86.1 g, 70% yield).

Intermediate 17: [2-Bromo-4-(3-fluoro-pyridin-4-ylcarbamoyl)-benzyl]-carbamic acid tert-butyl ester

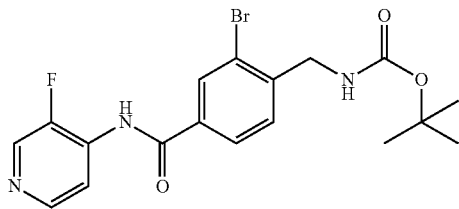 [SMILES: CC(C)(C)OC(=O)NCc1ccc(C(=O)Nc2ccncc2F)cc1Br]

Intermediate 17 was prepared as described for Intermediate 16.

Intermediate 18: 2'-(tert-Butoxycarbonylamino-methyl)-5'-(pyridin-4-ylcarbamoyl)-biphenyl-3-carboxylic acid

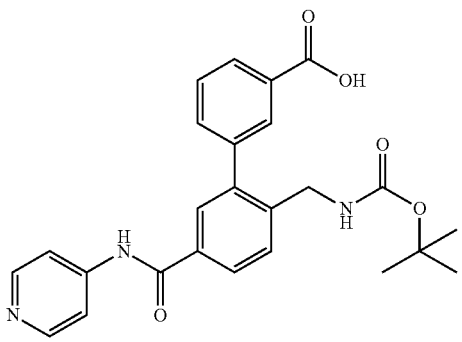 [SMILES: CC(C)(C)OC(=O)NCc1ccc(C(=O)Nc2ccncc2)cc1-c1cccc(C(=O)O)c1]

To a solution of Intermediate 16 (35 g, 0.086 mol, 1.0 eq) and 3-carboxyphenylboronic acid (14.27 g, 0.086, 1.0 eq) in DMF (350 ml) and H₂O (87.5 ml) was added Na₂CO₃ (18.2 g, 0.172 mol, 2.0 eq). Then Pd(dppf)Cl₂ (3.15 g, 0.0043 mol, 0.05 eq) was added to the solution under N₂. The resulting solution was stirred at 100° C. for 16 hrs. Solvent was evaporated under vacuum and the residue was purified by column chromatography on silica gel using DCM: MeOH=10:1 to give the title compound (27 g, 70% yield) as brown solid.

Intermediate 19: 2'-(tert-Butoxycarbonylamino-methyl)-5'-(3-fluoro-pyridin-4-ylcarbamoyl)-biphenyl-3-carboxylic acid

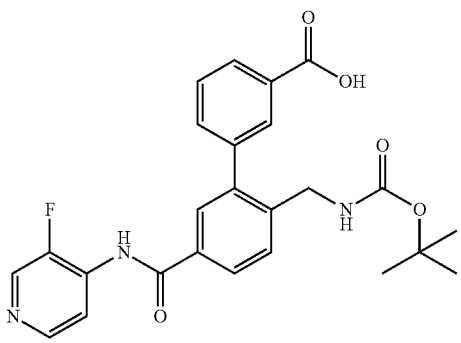 [SMILES: CC(C)(C)OC(=O)NCc1ccc(C(=O)Nc2ccncc2F)cc1-c1cccc(C(=O)O)c1]

Intermediate 19 was prepared as described for Intermediate 18 starting from intermediate 17.

The following intermediates were prepared in a similar way:

| Name | Intermediate | Structure |
|---|---|---|
| 2'-(tert-Butoxycarbonylamino-methyl)-5'-(3-fluoro-pyridin-4-ylcarbamoyl)-biphenyl-4-carboxylic acidr | 20 | 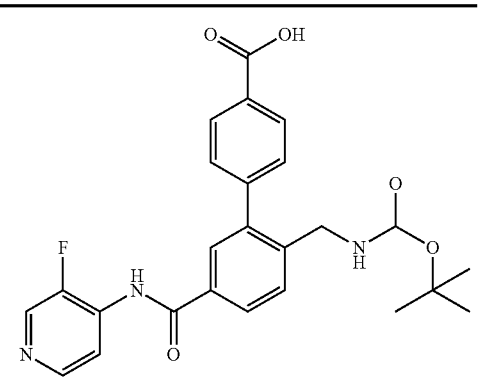 |

-continued

| Name | Intermediate | Structure |
|---|---|---|
| [3'-Hydroxy-5-(pyridin-4-ylcarbamoyl)-biphenyl-2-ylmethyl]-carbamic acid tert-butyl ester | 21 | 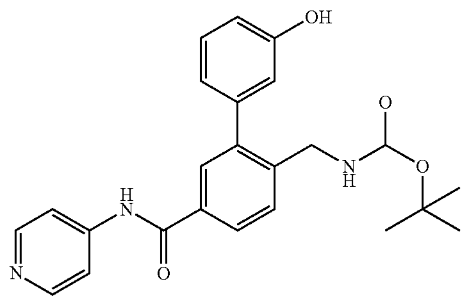 [SMILES: CC(C)(C)OC(O)NCc1ccc(C(=O)Nc2ccncc2)cc1-c1cccc(O)c1] |
| [5-(3-Fluoro-pyridin-4-ylcarbamoyl)-3'-hydroxy-biphenyl-2-ylmethyl]-carbamic acid tert-butyl ester | 22 | 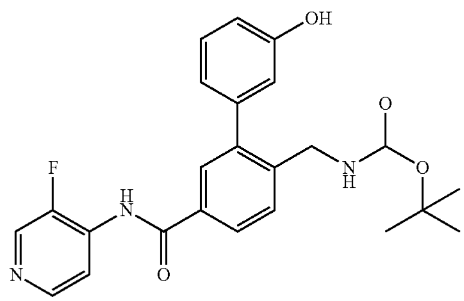 [SMILES: CC(C)(C)OC(O)NCc1ccc(C(=O)Nc2ccncc2F)cc1-c1cccc(O)c1] |
| [3'-Amino-5-(pyridin-4-ylcarbamoyl)-biphenyl-2-ylmethyl]-carbamic acid tert-butyl ester | 23 | 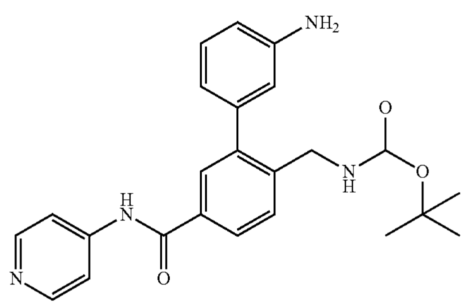 [SMILES: CC(C)(C)OC(O)NCc1ccc(C(=O)Nc2ccncc2)cc1-c1cccc(N)c1] |
| [3'-Amino-5-(3-fluoro-pyridin-4-ylcarbamoyl)-biphenyl-2-ylmethyl]-carbamic acid tert-butyl ester | 24 | 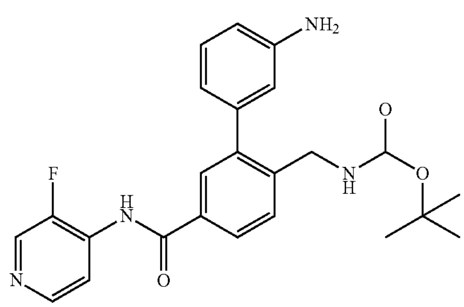 |
| (E/Z)-3-[2'-(tert-Butoxycarbonylamino-methyl)-5'-(pyridin-4-ylcarbamoyl)-biphenyl-3-yl]-acrylic acid | 25 | 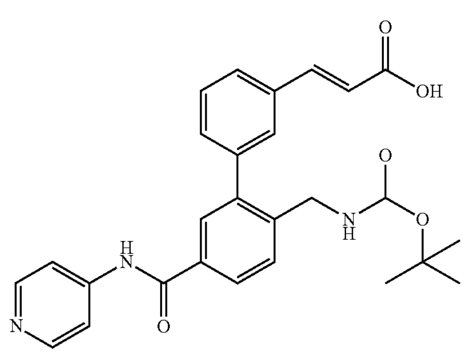 [SMILES: CC(C)(C)OC(O)NCc1ccc(C(=O)Nc2ccncc2)cc1-c1cccc(/C=C/C(=O)O)c1] |

-continued

| Name | Intermediate | Structure |
|---|---|---|
| [2'-(tert-Butoxycarbonylamino-methyl)-5'-(3-fluoro-pyridin-4-ylcarbamoyl)-biphenyl-3-yl]-acetic acid | 26 | 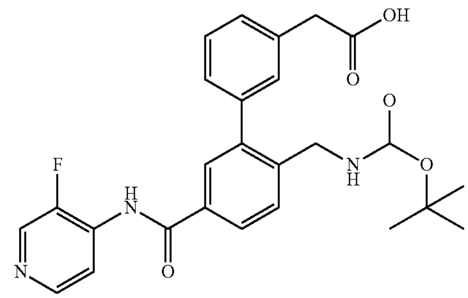 [SMILES: CC(C)(C)OC(O)NCc1ccc(C(=O)Nc2ccncc2F)cc1-c1cccc(CC(=O)O)c1] |

Intermediate 27 [2'-(tert-Butoxycarbonylamino-methyl)-5'-(pyridin-4-ylcarbamoyl)-biphenyl-3-yloxy]-acetic acid

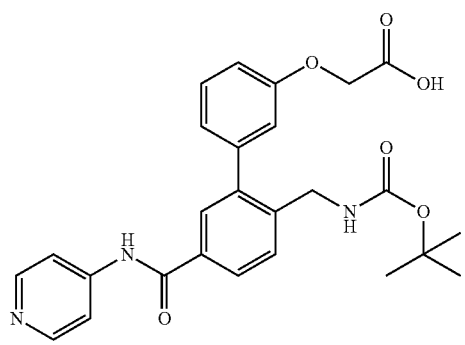 [SMILES: CC(C)(C)OC(=O)NCc1ccc(C(=O)Nc2ccncc2)cc1-c1cccc(OCC(=O)O)c1]

To a solution of common intermediate (30 g, 0.074 mol, 1.0 eq) and [3-(4,4,5,5-Tetramethyl-[1,3,2]dioxaborolan-2-yl)-phenoxy]-acetic acid ethyl ester (23 g, 0.074, 1.0 eq) in DMF (300 ml) and $H_2O$ (75 ml) was added Na2CO3 (15.6 g, 0.147 mol, 2.0 eq). Then added Pd(dppf)Cl2 (2.7 g, 0.0037 mol, 0.05 eq) to the solution under N2. The resulting solution was stirred at 100° C. for 16 hrs. Evaporated the solvent and the residue was dissolved in MeOH 200 ml, added into 148 ml 1M LiOH, the resulting solution was stirred at 30° C. for 16 hrs, checked by LC-MS. Evaporated the solvent to ⅓ then adjusted the pH=5 with 20% aqueous hydrochloric acid, then evaporated the solvent and the residue was purified by column chromatography on silica gel using DCM: MeOH=10:1 to give the title compound (23.8 g, 67.4% two steps) as white solid.

Intermediate 28 [2'-(tert-Butoxycarbonylamino-methyl)-5'-(3-fluoro-pyridin-4-ylcarbamoyl)-biphenyl-3-yloxy]-acetic acid

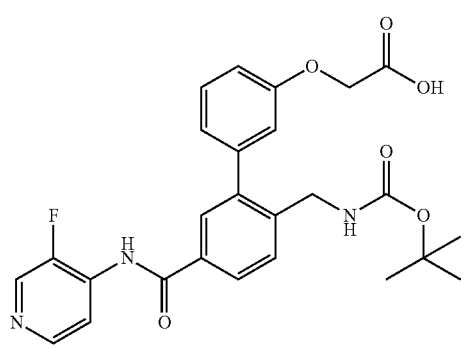 [SMILES: CC(C)(C)OC(=O)NCc1ccc(C(=O)Nc2ccncc2F)cc1-c1cccc(OCC(=O)O)c1]

Intermediate 28 was prepared as described for Intermediate 27 starting from intermediate 17.

When a compound of the invention contains an ester group, it can be made as described in the general scheme below:

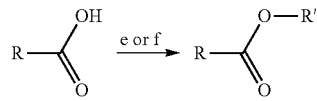

(e) R'OH, TBTU, HOBt, DIEA, DMF, rt or R'OH, DCC, DMAP, DCM, rt;
(f) Ghosez reagent [$Me_2C=C(Cl)NMe_2$], THF or DCM, rt, followed by R'OH.

Protocol E.

To a suspension of the corresponding carboxylic acid (0.25 mmol) in DMF (1 mL) were added DIEA (0.75 mmol, 3 eq), TBTU (0.325 mmol, 1.3 eq), HOBt (0.075 mmol, 0.3 eq) and the reaction mixture was stirred at rt for 5 min followed by addition of the corresponding alcohol (1.1-5 eq). The reaction mixture was stirred at rt for 1-16 h, then diluted with ethyl acetate (100 mL), washed with aqueous saturated sodium carbonate solution (50 mL), 0.1M HCl (50 mL), water (50 mL) and brine (50 mL). The organic phase was then dried over $MgSO_4$ and concentrated in vaccuo to afford the desired ester.

Alternative Protocol.

Acids of the general type can be converted to the corresponding esters according to the Steglich method mediated by action of DCC in the presence of DMAP. This chemistry is well known to those skilled in the art and can be performed according to the literature precedents (B. Neises and W. Steglich. "Esterification of carboxylic acids with dicyclohexyl carbodiimide/4-dimethylaminopyridine"; Coll. Vol. 7: 93)

Protocol F.

To a solution of the corresponding carboxylic acid (0.25 mmol) in THF or DCM (1 mL) cooled to 0° C. was added Ghosez reagent (1-chloro-N,N,2-trimethyl-1-propenylamine, CAS number 26189-59-3, 0.5 mmol, 2 eq). The reaction mixture was stirred for 1-3 h while being warmed up to rt followed by addition of the corresponding alcohol (1.2 eq). The reaction mixture was stirred at rt for 1 h. The solvent was evaporated in vaccuo. The residue was diluted with EtOAc and washed with saturated $NaHCO_3$. The organic layer was dried over $MgSO_4$ and the solvent was removed under reduced pressure General Scheme for Conversion of Acids into Thioesters.

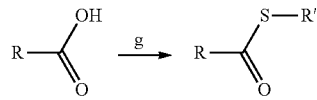

(g) R'SH, DCC, DMAP, DCM or DMF, rt

To a solution of the corresponding carboxylic acid (1 mmol) in DCM or DMF at 0° C. (10 mL) were added DCC (1.1 mmol, 1.1 eq) and DMAP (0.1 mmol, 0.1 eq) followed by addition of the corresponding thiol (2-4 eq). The cooling bath was removed and the reaction mixture as stirred at rt for 1-16 h. The reaction mixture was diluted with DCM (100 mL), washed with aqueous saturated sodium carbonate solution (50 mL), 0.1M HCl (50 mL), water (50 mL) and brine (50 mL). The organic phase was then dried over MgSO₄ and concentrated in vaccuo to afford the desired thioester.

Alternative protocol: A mixture of the corresponding carboxylic acid (200 mg, 1.0 eq) and ethanethiol (2.0 eq) in CH₃CN (4 ml) was added HOBT (0.4 eq) and EDCI (about 120 mg, 1.5 eq). The reaction mixture was stirred at 30° C. for 16 hrs. LC-MS showed the reaction was complete. Then the solvent was concentrated to dryness to give crude product, which was used directly for next step without purification.

The crude product was dissolved in DCM/TFA=7:1 (4 ml). The reaction mixture was stirred at 30° C. for 16 hrs. LC-MS showed the reaction was complete. Then the reaction mixture was concentrated and the crude product was purified by prep HPLC to give the final product.

General Scheme for Conversion of Heteroalkyl Groups to Lactone Derivatives

Alcohols or thiols of general type can be converted to the corresponding heteroalkyl linked lactones according to the general scheme (X=O or S).

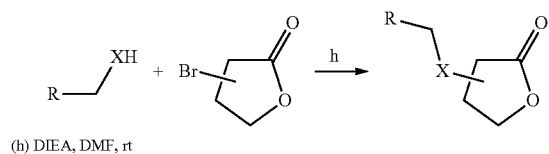

(h) DIEA, DMF, rt

To a solution of the corresponding thiol (1 mmol) in DMF (10 mL) was added DIEA (2 mmol, 2 eq) followed by addition of the corresponding bromolactone (1.1 mmol, 1.1 eq). The reaction mixture was stirred at rt for 1 h then diluted with ethyl acetate (100 mL), washed 0.1M HCl (50 mL), water (50 mL) and brine (50 mL). The organic phase was then dried over MgSO₄ and concentrated in vaccuo to afford the desired lactone.

Intermediate 29:
3-(2-Amino-ethylsulfanyl)-dihydro-furan-2-one

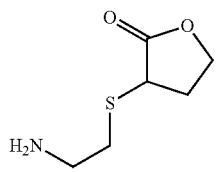

3-Bromo-dihydro-furan-2-one (2.49 g, 15.1 mmol) and 2-(Boc-amino)ethanethiol (2.9 g, 16.5 mmol) were dissolved in 40 mL of CH₃CN. Then K₂CO₃(4.14 g, 30 mmol) wasn added to the solution. Let it stir at 80° C. for 16 h. The solvent was evaporated to dryness and the residue was purified by column chromatography (PE/EtOAc=4/1) to 3.8 g of BOC protected Intermediate 29 as colorless oil.

The previous compound (3.7 g, 14.16 mmol) was dissolved in 10 ml of EtOAc. Then 40 mL of 4N HCl/EtOAc was added to the solution. Let it stir at 25° C. for 2 h. The white solid was filtered and washed with PE to give 2 g of Intermediate 29.

Intermediate 30:
3-(3-Amino-propylsulfanyl)-dihydro-furan-2-one

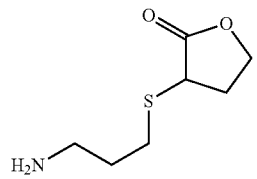 [SMILES: NCCCSC1CCOC1=O]

3-Amino-propan-1-ol (40 g, 0.533 mol) was dissolved in 1 L of THF. Then Boc₂O (127.26 g, 0.586 mol) in 450 mL of THF was added dropwise to the solution at 25° C. Let it stir at 25° C. for 12 h. 500 mL of water was added to the solution and it was extracted with EtOAc (200 mL*3), dried with MgSO₄. Filtered and evaporated to dryness to give 60 g of the corresponding BOC protected compound as colorless oil.

Boc protected 3-Amino-propan-1-ol (30 g, 0.171 mol) was dissolved in 600 mL of dry THF. TEA (48 mL, 0.345 mol) was added to the solution. Then MsCl (26.67 mL) was added slowly to the solution at 0° C. under N₂. Let it stir at 25° C. for 2 h. The mixture was washed with water and dried with MgSO4. Filtered and evaporated to dryness to give 40 g of Ms-protected product.

The above compound (40 g, 0.158 mol) and CH₃COSK (54.1 g, 0.474 mol) were mixed in 2.7 L of EtOH. Let it stir at 90° C. under N₂ for 16 h. The solvent was evaporated to dryness and the mixture was purified by column chromatography (PE/EA=10/1) to give 15 g of thioacetic acid S-(3-tert-butoxycar bonylamino-propyl) ester as orange solid.

Na (708 mg, 30.8 mmol) was added into 100 mL of dry methanol and stirred until the metal sodium disappeared. To the solution was added the above compound (6 g, 25.8 mmol). The mixture was stirred at room temperature for 2 hours. TLC showed the reaction was completed. To the mixture was added a solution of 3-Bromo-dihydro-furan-2-one (5.46 g, 33.3 mmol) in 100 mL of CH₂Cl₂ followed by addition of 100 mL of DMF. The resulting mixture was stirred at 60° C. for 6 hours. TLC showed the reaction was completed. The reaction mixture was partitioned between 800 mL of EA and 400 mL of water and the aqueous layer was extracted by EA (800 mL×2). The combined organic layers were dried, filtered and concentrated to give the crude product, which was purified by column chromatography (PE/EA=4/1) to give 3.5 g of the title BOC protected compound as colorless oil.

The BOC protected derivative (3.5 g, 12.71 mmol) was dissolved in 10 ml of EtOAc. Then 40 mL of 4N HCl/EtOAc was added to the solution. The reaction mixture was stirred at 25° C. for 2 h. The white solid was filtered and washed with PE to give 2.5 g of the title compound.

Intermediate 30:
4-(2:Amino-ethyl)-[1,3]dioxolan-2-one

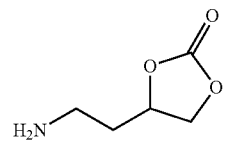

60 mL saturated solution of NH₃ in CH₃OH was added to 4-bromo-but-1-ene (3 mL) quickly in a 100 mL reactor of autoclave. Then the mixture was stirred at 90° C. for 16 hours in the autoclave. After reaction, the remained solvent was removed under vacuo. The hydrobromide salt of but-3-enylamine (12 g, 95%) was recovered as a yellow power.

To a suspension of the previous compound (12 g, 0.08 mol) in CH$_2$Cl$_2$ (1 L) was added a solution of K$_2$CO$_3$ (33 g, 0.24 mol) in water (80 mL) under N$_2$. The bi-phasic mixture was cooled to 0° C. and Cbz-Cl (22 g, 0.128 mol) was added dropwise. After 15 min of stirring at the temperature, the reaction mixture was stirred for 14 hours at room temperature. After the reaction completed, to the mixture was added CH$_2$Cl$_2$ and water, the organic layer was dried over anhydrous Na$_2$SO$_4$, concentrated under vacuum and purified through silica gel chromatography (petroleum/ethyl acetate=3:1) to give the corresponding Cbz protected compound (12.2 g, 75%) as colorless oil.

To a stirred solution of the above compound (12.2 g, 59.5 mmol) in acetone/H$_2$O (60 mL/50 mL) was added NMO (7.3 g, 62.5 mmol) and OsO$_4$ (303 mg, 1.2 mmol) at room temperature under N$_2$. After addition of OsO$_4$, the color of reaction solution turned black. Then the mixture was stirred at room temperature for 10 h. TLC (CH$_2$Cl$_2$/MeOH=10:1) showed the starting material was consumed completely. The mixture was evaporated under vacuo. To the residue was added water and extracted with ethyl acetate. The organic layer was dried over anhydrous Na$_2$SO$_4$, concentrated under vacuum and purified through silica gel chromatography (CH$_2$Cl$_2$/MeOH=10:1) to give the corresponding diol (12 g, 85%) as pale solid.

To a solution of the diol (9 g, 37.66 mmol) in CH$_2$Cl$_2$ (200 mL) was added triethylamine (15.2 g, 151 mmol) at −20~−30° C. under N$_2$. After several minutes, triphosgene (5.5 g, 18.83 mmol) was added to the mixture dropwise at this temperature and stirred at −20~−30° C. for half an hour. Then the mixture was stirred at room temperature for 15 h. TLC (CH$_2$Cl$_2$/MeOH=10:1) showed the starting material was almost consumed. To the mixture was added water and extracted with ethyl acetate. The organic layer was dried over anhydrous Na$_2$SO$_4$, concentrated under vacuum and purified through silica gel chromatography (CH$_2$Cl$_2$/MeOH=10:1) to give the corresponding cyclized dioxolane (6.5 g, 55%) as pale solid.

To a solution of the above compound (5.5 g, 20.5 mmol) in CH$_3$OH (100 mL) was added dry Pd/C (550 mg, 10%) quickly under N$_2$. Then the mixture was stirred at room temperature under H$_2$ overnight. TLC (CH$_2$Cl$_2$/MeOH=10:1) showed the starting material was almost consumed. The mixture was filtered via a pad of celite. The solution was evaporated under vacuo and purified by silica gel (CH$_2$Cl$_2$/MeOH=10:1) to give the title intermediate (2.0 g, 77%) as white solid.

Intermediate 31:
3-(2-Hydroxy-ethylsulfanyl)-dihydro-furan-2-one

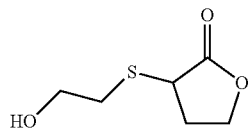

To a solution of 2-mercapto-ethanol (2560 μmol) in THF (4 ml) were added DIEA (1.1 eq) and 3-bromo-dihydro-furan-2-one (1 eq). The reaction mixture was stirred at RT for 4 hours. The precipitate was filtered and the solvent was removed under reduced pressure.

Intermediate 32:
3-(3-Hydroxy-propylsulfanyl)-dihydro-furan-2-one

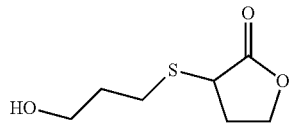 [SMILES: O=C1OCCC1SCCCO]

To a solution of 3-mercapto-propan-1-ol (1685 μmol) in DMF (2 ml) were added DIEA (1.5 eq) and 3-bromo-dihydro-furan-2-one (1 eq). The reaction mixture was stirred at RT for 4 hours. The precipitate was filtered and the solvent was removed under reduced pressure.

Intermediate 33: 3-bromomethyl-oxetan-2-one

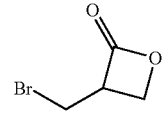

To a solution of Br$_2$ (4.86 g, 0.0303 mol) in ether (150 mL) was added dropwise a solution of compound but-3-enoic acid (2.6 g, 0.0302 mol) in saturated NaHCO$_3$ (110 mL) at 0° C. After addition the mixture was stirred for 1 h. TLC (PE: EA=4:1) showed the reaction was complete. Saturated solution (20 mL) was added. The reaction was extracted with EtOAc (100 mL×3). The combined layers were washed with brine, dried over Na$_2$SO$_4$, filtered and then concentrated in vacuo and purified by column chromatography on silica gel (petroleum ether/ethyl acetate=20:1) to obtain the title compound (1.73 g, 35%) as a white oil.

Intermediate 34: 3-(Piperidin-4-ylmethylsulfanyl)-dihydro-furan-2-one

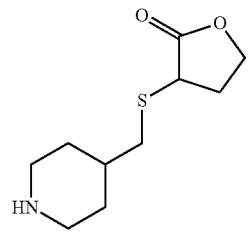 [SMILES: O=C1OCCC1SCC1CCNCC1]

Intermediate 34 was prepared as described for Intermediate 30 starting from 4-hydroxymethyl-piperidine-1-carboxylic acid tert-butyl ester.

Intermediate 35:
3-(2-hydroxy-ethoxy)-dihydro-furan-2-one

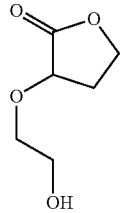

A solution of 50 g of 2,3-dihydro-furan in methanol 700 mL and chloroform 300 mL was added 90 g of m-chloroperoxybenzoic acid in small portions with stirring at 0° C. for 15 mins, then the reaction mixture was stirred at 25° C. for 15 hrs. The resulting mixture was filtered, the filtrate was concentrated under reduced pressure, the residue was dissolved in chloroform 500 ml, washed with 200 mL of sat. NaHCO₃ and 200 mL of brine, The organic layer was dried over Na₂SO4 and filtered. The filtrate was concentrated under reduced pressure to afford 30 g of 2-methoxy-tetrahydro-furan-3-ol.

A solution of 2-methoxy-tetrahydro-furan-3-ol in DMF 200 mL was added sodium hydride in small portions with stirring at 0° C. for 2 hrs, then 2-Benzyloxy-ethanol was added from the dropping funnel over a period of 1 hour, the resulting mixture was stirred at 25° C. for 15 hrs, it was poured into 400 mL water, EtOAC (1 L) were added and separated. The organic layer was washed with sat. NaHCO₃ (500 mL), dried over Na2SO4, filtered and concentrated, The residue was purified by column chromatography (PE:EA=5:1) to yield 10 g of 3-(2-Benzyloxy-ethoxy)-2-methoxy-tetrahydro-furan (oil).

To a solution of the previous compound in 300 mL of 40% aqueous MeCN was added 30 mL of concentrated H₂SO4 and the mixture stirred at 35° C. for 4 hrs. The resulting mixture was neutralized with NaHCO₃, then it was concentrated under reduced pressure, EtOAC (300 mL) were added and separated. The organic layer was washed with brine (100 mL), dried over MgSO4, filtered and concentrated, the residue was purified by column chromatography (PE:EA=1:1) to yield 4.8 g of 3-(2-benzyloxy-ethoxy)-tetrahydro-furan-2-ol (oil).

To a solution of the above compound in 25 mL of DMSO was added 17 mL of Ac₂O with stirring at 25° C. for 15 hrs, the resulting mixture was poured into 100 mL of water, EtOAc (200 mL) were added and separated. The organic layer was washed with sat. NaHCO₃ (50 mL) and brine (50 mL), dried over MgSO4, filtered and concentrated. The residue was purified by column chromatography (PE:EA=5:1) to yield 2.5 g of 3-(2-benzyloxy-ethoxy)-dihydro-furan-2-one (oil).

A mixture of the above compound and 0.5 g of palladium on charcoal in 100 mL of methanol was stirred under 1 atm of H₂ 25° C. for 5 hrs, the resulting mixture was filtered and filtrate was concentrated under reduced pressure to afford 1.35 g of Intermediate 35 (oil).

Intermediate 36:
3-hydroxymethyl-dihydro-thiophen-2-one

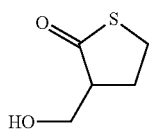

Thiobutyrolactone (10 g, 97.9 mmol) in anhydrous tetrahydrofuran (200 ml) was added dropwise to a stirred solution of lithium diisopropylamide [Diisopropylamine (15.1 g, 117.5 mmol) and n-butyllithium in hexane 2.5M (47.0 ml, 117.5 mmol) at −78° C.]. The resulting solution was stirred for 10 minutes at which time formaldehyde (50 g) carried in a stream of N₂ was added [Formaldehyde was formed by heating paraformaldehyde to 150° C.]. The reaction was allowed to proceed for 2.5 h at −78° C. The formaldehyde stream was removed and reaction was allowed to proceed for an additional 30 mins. Then 300 ml of ethyl acetate was poured into the reaction mixture while stirring then quenched by the addition of (~300 ml) 1M HCl at −78° C. then allowed to warm to room temperature while filtering through a bed of celite. The filtrate was extracted with ethyl acetate 100 ml for more than 5 times and the combined organic layers were dried (Na₂SO₄) and concentrated to an oil. The oil was purified by chromatography (PE/EA=9/1) to give 1.70 g of the title compound as colorless oil.

Intermediate 37:
3-hydroxymethyl-dihydro-furan-2-one

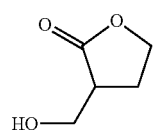

To a stirred suspension of NaH (9.77 g, 244 mmol, 60%) in 250 ml of THF was added dropwise the mixture of 20 g of γ-butyrolactone (20 g, 232 mmol) and methyl formate (14 g, 232 mmol). The resulting mixture was stirred at 25° C. for 20 hrs. The solid material was filtered and washed with hexane, after which it was suspended dry methanol (800 ml). A solution of HCl-MeOH (4M) was added dropwise and the mixture was stirred for 1 hr. After carefully neutralization with NaOH, the mixture was filtered and the filtrate was carefully concentrated. Water was added and the solution was worked up as usual to afford 23 g of crude ester. Vacuum distillation (100-120° C., 20 mmHg) afforded 14 g of 2-methoxy-tetrahydro-furan-3-carboxylic acid methyl ester as a colorless oil.

To a solution of 2-methoxy-tetrahydro-furan-3-carboxylic acid methyl ester (10 g, 62.5 mmol) in 60 ml of dry THF was added 4.75 g (125 mmol) LiAlH₄ at 25° C. The mixture was refluxed for 4 hrs and cooled. 4.75 ml of H₂O and 4.75 ml of aq. NaOH (10%) were added to the reaction mixture in turn. The resulting mixture was filtered and the filtrate was concentrated to yield (2-methoxy-tetrahydro-furan-3-yl)-methanol (7 g).

To a solution of the above compound (7 g, 53 mmol) in 300 ml of DMF was added NaH (3.2 g, 80 mmol, 60%), followed by BnBr (12.4 ml, 106 mmol). The resulting mixture was stirred at 25° C. for 2 hrs and then poured into 1 L of water. And then the mixture was extracted with EtOAc (500 ml*3). The combined organic layer was dried over MgSO₄, filtered, and concentrated. The residue was purified by column chromatography (PE:EA=2:1) to afford 3-benzyloxymethyl-2-methoxy-tetrahydro-furan (10 g).

To a solution of the previous compound (10 g, 45 mmol) in DCM (180 ml) was added BF₃.Et₂O (3.4 ml) and m-CPBA (9.86 g, 48.75 mmol, 85%). The resulting mixture was stirred at 25° C. overnight. The reaction mixture was diluted with EtOAc (500 ml) and washed with 10% Na₂S₂O₃, sat. NaHCO₃ and brine. The organic layer was dried over MgSO4, filtered and concentrated. The residue was purified by column chromatography to afford the benzyl-protected intermediate 37 (6.7 g).

To a solution of the above compound (6.7 g, 32.5 mmol) in EtOH (200 ml) was added 1 g of 10% of Pd/C and hydrogenated for 10 hrs at 25° C., 1 atm. The mixture was filtered and concentrated to afford the title compound (3.9 g).

Intermediate 38:
5-(2-hydroxy-ethyl)-3H-furan-2-one

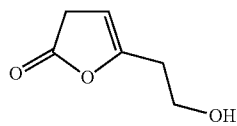

To a cooled solution of furan (3.40 g, 50.0 mmol) in THF (150 mL) was added n-BuLi (22 mL, 2.5M solution in hexane, 55.0 mmol) at 0° C. under inert gas atmosphere. The solution was allowed to warm to room temperature and stirred for 3 h. Then TMSCI (5.34 g, 50 mmol) was added dropwise at 0° C. and the solution was stirred for further 3 h at room temperature. Subsequently, the solution was again cooled to 0° C. and n-BuLi (22 mL, 2.5M solution in hexane, 55.0 mmol) was added a second time. After stirring for 3 h at room temperature ethyleneoxide (2.42 g, 55.0 mmol) was condensed by an acetone/dry ice condenser into the solution and the solution was stirred for further 12 h at room temperature. The mixture was quenched with aq NH$_4$Cl, and then extracted with EtOAc and the combined organic layers were dried over Na$_2$SO$_4$ to afforded the desired product (5 g, 27.1 mmol, 54% over two steps) as a yellow liquid.

To a solution of the above compound (3 g, 16.45 mmol) and NaOAc (1.64 g, 20 mmol) in CH$_2$Cl$_2$ (30 mL) was added dropwise a solution of CH$_3$CO$_3$H (16 g, 40% in H$_2$O) in CH$_2$Cl$_2$ (90 mL). The reaction mixture was stirred for overnight at room temperature. The reaction was quenched with Na$_2$SO$_3$, washed with saturated NaHCO$_3$ and brine. The organic layer was concentrated under reduced pressure. The resulting residue was purified by column chromatography (PE:EA=1:2) to give 0.5 g of desired product as a yellow liquid (0.5 g, yield: 24%).

Intermediate 39:
(2-Oxo-tetrahydro-furan-3-ylsulfanyl)-acetic acid

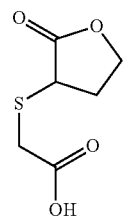 [SMILES: O=C(O)CSC1CCOC1=O]

Potassium ethylxanthate (58.0 g, 364 mmol) was suspended in 200 mL of dry acetone at room temperature. tert-Butyl chloroacetate (50 g, 332 mmol) was added dropwise with stirring. After 18 hrs potassium chloride was removed by filtration, and the solvent was evaporated. The residue was taken up into ether, washed with 5% NaHCO$_3$, water, and brine, dried over MgSO$_4$, filtered, and evaporated to leave 80 g of O-ethyl S-(tert-butoxycarbonyl)methyl dithiocarbonate as a thick oil. This oil was stirred with ethanolamine (323 mmol) for 2 hrs at room temperature. The reaction mixture was taken up into ethyl acetate, washed with 1.2N HCl, water, and brine, dried over MgSO$_4$, filtered, and evaporated. The residue was vacuum dis-tilled to give 30 g of mercapto-acetic acid tert-butyl ester as a clear oil.

To a solution of 3-bromo-dihydro-furan-2-one (16 g, 97.6 mmol) in 300 mL of CH$_3$CN was added K$_2$CO$_3$ (20 g, 146 mmol), followed by mercapto-acetic acid tert-butyl ester (14.5 g, 98 mmol). The reaction mixture was refluxed for 2 hrs and cooled. The mixture was filtered and the filtrate was concentrated. The residue was redissolved in 300 mL of EtOAc and the resulting solution was washed with 1N HCl (100 mL*2). The organic layer was dried over MaSO$_4$, filtered and concentrated to afford the ter-butyl ester title compound (23 g). 16 g of the ester was dissolved in 250 ml of HCl-MeOH (4M) and stirred at 25° C. for 4 hrs. The reaction mixture was concentrated below 45° C. in vacuum. The residue was purified by column chromatography (EtOAc) to afford 7 g of the title compound.

B.1. Compounds of the Invention

In the tables 1 to 19 that are set forth below, exemplary compounds of the invention are set out in tabulated form. In these tables, the name of the compound, an arbitrarily assigned compound number and structural information are set out.

Table 1 shows the results for compounds of Formula IIa or IIb

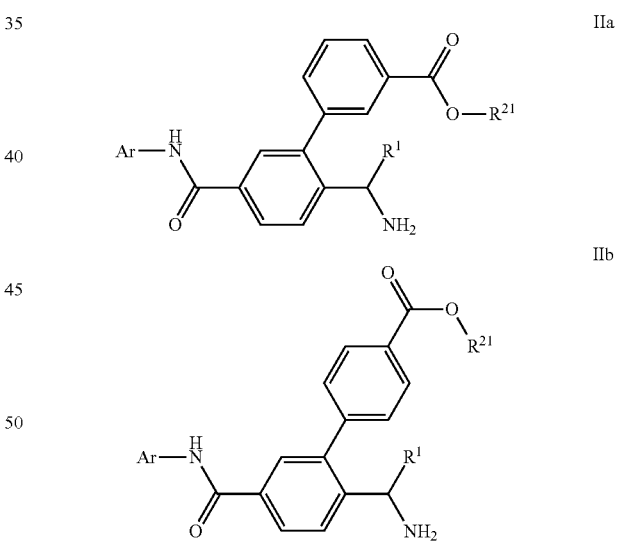

TABLE 1

| Name | Cpd | Ar | —R$^1$ | Formula | —R$^{21}$ |
|---|---|---|---|---|---|
| 2'-Aminomethyl-5'-(pyridin-4-ylcarbamoyl)-biphenyl-3-carboxylic acid methyl ester | 1 | pyridin-4-yl | —H | IIa | methyl |

TABLE 1-continued

| Name | Cpd | Ar | —R¹ | Formula | —R²¹ |
|---|---|---|---|---|---|
| 2'-Aminomethyl-5'-(pyridin-4-ylcarbamoyl)-biphenyl-4-carboxylic acid methyl ester | 2 |  | —H | IIb |  |
| 2'-Aminomethyl-5'-(pyrimidin-4-ylcarbamoyl)-biphenyl-3-carboxylic acid methyl ester | 3 |  | —H | IIa |  |
| 2'-(1-Amino-ethyl)-5'-(pyridin-4-ylcarbamoyl)-biphenyl-3-carboxylic acid methyl ester | 4 |  | —Me | IIa |  |
| 2'-(1-Amino-ethyl)-5'-(3-fluoro-pyridin-4-ylcarbamoyl)-biphenyl-3-carboxylic acid methyl ester | 5 | 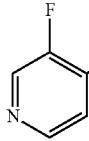 | —Me | IIa |  |
| 2'-(1-Amino-ethyl)-5'-(1H-pyrrolo[2,3-b]pyridin-4-ylcarbamoyl)-biphenyl-3-carboxylic acid methyl ester | 6 | 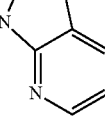 | —Me | IIa |  |
| 2'-Aminomethyl-5'-(pyridin-4-ylcarbamoyl)-biphenyl-3-carboxylic acid ethyl ester | 7 |  | —H | IIa |  |
| 2'-(1-Amino-ethyl)-5'-(pyridin-4-ylcarbamoyl)-biphenyl-3-carboxylic acid ethyl ester | 8 |  | —Me | IIa |  |
| 2'-(1-Amino-ethyl)-5'-(3-fluoro-pyridin-4-ylcarbamoyl)-biphenyl-3-carboxylic acid ethyl ester | 9 | 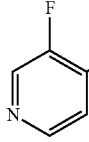 | —Me | IIa |  |
| 2'-Aminomethyl-5'-(pyridin-4-ylcarbamoyl)-biphenyl-3-carboxylic acid propyl ester | 10 |  | —H | IIa |  |
| 2'-(1-Amino-ethyl)-5'-(pyridin-4-ylcarbamoyl)-biphenyl-3-carboxylic acid propyl ester | 11 |  | —Me | IIa |  |
| 2'-(1-Amino-ethyl)-5'-(3-fluoro-pyridin-4-ylcarbamoyl)-biphenyl-3-carboxylic acid propyl ester | 12 | 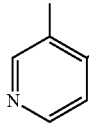 | —Me | IIa |  |

TABLE 1-continued

| Name | Cpd | Ar | —R¹ | Formula | —R²¹ |
|---|---|---|---|---|---|
| 2'-(1-Amino-ethyl)-5'-(pyridin-4-ylcarbamoyl)-biphenyl-3-carboxylic acid butyl ester | 13 | 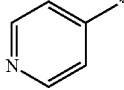 | —Me | IIa | 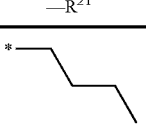 |
| 2'-Aminomethyl-5'-(pyridin-4-ylcarbamoyl)-biphenyl-3-carboxylic acid butyl ester | 14 | 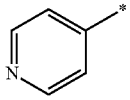 | —H | IIa | 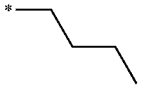 |
| 2'-Aminomethyl-5'-(pyridin-4-ylcarbamoyl)-biphenyl-3-carboxylic acid pentyl ester | 15 | 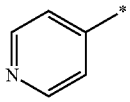 | —H | IIa | 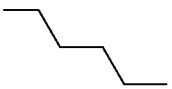 |
| 2'-(1-Amino-ethyl)-5'-(pyridin-4-ylcarbamoyl)-biphenyl-3-carboxylic acid pentyl ester | 16 | 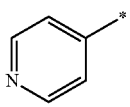 | —Me | IIa | 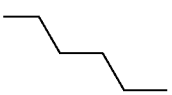 |
| 2'-Aminomethyl-5'-(pyridin-4-ylcarbamoyl)-biphenyl-3-carboxylic acid hexyl ester | 17 | 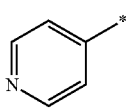 | —H | IIa | 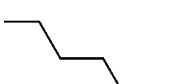 |
| 2'-(1-Amino-ethyl)-5'-(pyridin-4-ylcarbamoyl)-biphenyl-3-carboxylic acid heptyl ester | 18 | 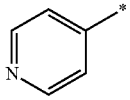 | —Me | IIa | 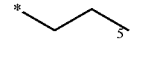 |
| 2'-(1-Amino-ethyl)-5'-(pyridin-4-ylcarbamoyl)-biphenyl-3-carboxylic acid octyl ester | 19 | 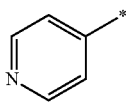 | —Me | IIa | 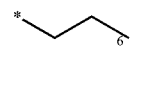 |
| 2'-(1-Amino-ethyl)-5'-(pyridin-4-ylcarbamoyl)-biphenyl-3-carboxylic acid decyl ester | 20 | 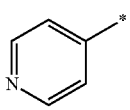 | —Me | IIa | 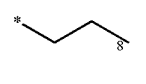 |
| 2'-(1-Amino-ethyl)-5'-(pyridin-4-ylcarbamoyl)-biphenyl-3-carboxylic acid undecyl ester | 21 | 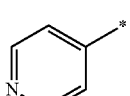 | —Me | IIa | 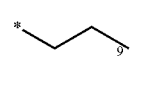 |
| 2'-(1-Amino-ethyl)-5'-(pyridin-4-ylcarbamoyl)-biphenyl-3-carboxylic acid dodecyl ester | 22 | 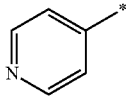 | —Me | IIa | 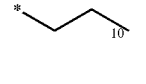 |
| 2'-(1-Amino-ethyl)-5'-(pyridin-4-ylcarbamoyl)-biphenyl-3-carboxylic acid tridecyl ester | 23 | 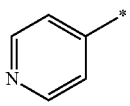 | —Me | IIa | 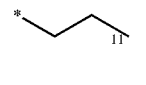 |
| 2'-(1-Amino-ethyl)-5'-(pyridin-4-ylcarbamoyl)-biphenyl-3-carboxylic acid hexadecyl ester | 24 | 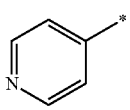 | —Me | IIa | 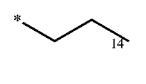 |
| 2'-(1-Amino-ethyl)-5'-(pyridin-4-ylcarbamoyl)-biphenyl-3-carboxylic acid dec-9-enyl ester | 25 | 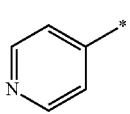 | —Me | IIa | 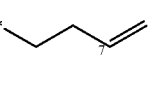 |

TABLE 1-continued

| Name | Cpd | Ar | —$R^1$ | Formula | —$R^{21}$ |
|---|---|---|---|---|---|
| 2'-Aminomethyl-5'-(pyridin-4-ylcarbamoyl)-biphenyl-3-carboxylic acid isopropyl ester | 26 | pyridin-4-yl | —H | IIa | isopropyl |
| 2'-(1-Amino-ethyl)-5'-(pyridin-4-ylcarbamoyl)-biphenyl-3-carboxylic acid isopropyl ester | 27 | pyridin-4-yl | —Me | IIa | isopropyl |
| 2'-(1-Amino-ethyl)-5'-(3-fluoro-pyridin-4-ylcarbamoyl)-biphenyl-3-carboxylic acid isobutyl ester | 28 | 3-fluoro-pyridin-4-yl | —Me | IIa | isobutyl |
| 2'-Aminomethyl-5'-(pyridin-4-ylcarbamoyl)-biphenyl-3-carboxylic acid tert-butyl ester | 29 | pyridin-4-yl | —H | IIa | tert-butyl |
| 2'-Aminomethyl-5'-(pyridin-4-ylcarbamoyl)-biphenyl-3-carboxylic acid cyclopropyl ester | 30 | pyridin-4-yl | —H | IIa | cyclopropyl |
| 2'-Aminomethyl-5'-(pyridin-4-ylcarbamoyl)-biphenyl-3-carboxylic acid cyclobutyl ester | 31 | pyridin-4-yl | —H | IIa | cyclobutyl |
| 2'-Aminomethyl-5'-(pyridin-4-ylcarbamoyl)-biphenyl-3-carboxylic acid cyclopentyl ester | 32 | pyridin-4-yl | —H | IIa | cyclopentyl |
| 2'-(1-Amino-ethyl)-5'-(pyridin-4-ylcarbamoyl)-biphenyl-3-carboxylic acid cyclopentyl ester | 33 | pyridin-4-yl | —Me | IIa | cyclopentyl |
| 2'-(1-Amino-ethyl)-5'-(pyridin-4-ylcarbamoyl)-biphenyl-3-carboxylic acid cyclohexyl ester | 34 | pyridin-4-yl | —Me | IIa | cyclohexyl |
| 2'-Aminomethyl-5'-(pyridin-4-ylcarbamoyl)-biphenyl-3-carboxylic acid cyclohexyl ester | 35 | pyridin-4-yl | —H | IIa | cyclohexyl |
| 2'-(1-Amino-ethyl)-5'-(pyridin-4-ylcarbamoyl)-biphenyl-3-carboxylic acid cyclopropylmethyl ester | 36 | pyridin-4-yl | —Me | IIa | cyclopropylmethyl |
| 2'-(1-Amino-ethyl)-5'-(3-fluoro-pyridin-4-ylcarbamoyl)-biphenyl-3-carboxylic acid cyclopropylmethyl ester | 37 | 3-fluoro-pyridin-4-yl | —Me | IIa | cyclopropylmethyl |

TABLE 1-continued

| Name | Cpd | Ar | —R¹ | Formula | —R²¹ |
|---|---|---|---|---|---|
| 2'-Aminomethyl-5'-(pyridin-4-ylcarbamoyl)-biphenyl-3-carboxylic acid cyclopentylmethyl ester | 38 | 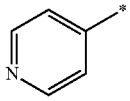 | —H | IIa | 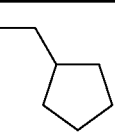 |
| 2'-Aminomethyl-5'-(pyridin-4-ylcarbamoyl)-biphenyl-3-carboxylic acid cyclohexylmethyl ester | 39 | 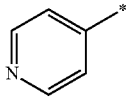 | —H | IIa | 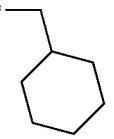 |
| 2'-(1-Amino-ethyl)-5'-(pyridin-4-ylcarbamoyl)-biphenyl-3-carboxylic acid isobutyl ester | 40 | 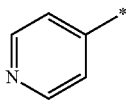 | —Me | IIa | 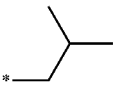 |
| 2'-Aminomethyl-5'-(pyridin-4-ylcarbamoyl)-biphenyl-3-carboxylic acid 2-methoxy-ethyl ester | 41 | 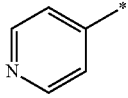 | —H | IIa | 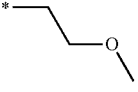 |
| 2'-Aminomethyl-5'-(pyridin-4-ylcarbamoyl)-biphenyl-3-carboxylic acid 2-methoxy-propyl ester | 42 | 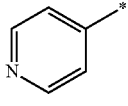 | —H | IIa | 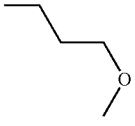 |
| 2'-Aminomethyl-5'-(pyridin-4-ylcarbamoyl)-biphenyl-3-carboxylic acid tetrahydro-pyran-4-yl ester | 43 | 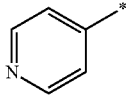 | —H | IIa | 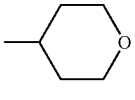 |
| 2'-(1-Amino-ethyl)-5'-(pyridin-4-ylcarbamoyl)-biphenyl-3-carboxylic acid tetrahydro-furan-2-ylmethyl ester | 44 | 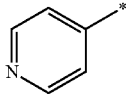 | —Me | IIa | 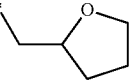 |
| 2'-(1-Amino-ethyl)-5'-(pyridin-4-ylcarbamoyl)-biphenyl-3-carboxylic acid tetrahydro-pyran-2-ylmethyl ester | 45 | 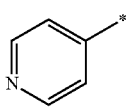 | —Me | IIa | 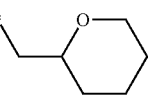 |
| 2'-(1-Amino-ethyl)-5'-(3-fluoro-pyridin-4-ylcarbamoyl)-biphenyl-3-carboxylic acid tetrahydro-furan-2-ylmethyl ester | 46 | 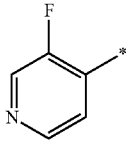 | —Me | IIa | 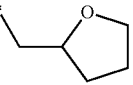 |
| 2'-(1-Amino-ethyl)-5'-(3-fluoro-pyridin-4-ylcarbamoyl)-biphenyl-3-carboxylic acid tetrahydro-pyran-2-ylmethyl ester | 47 | 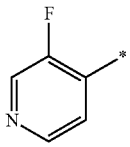 | —Me | IIa | 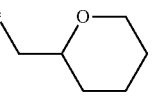 |
| 2'-Aminomethyl-5'-(pyridin-4-ylcarbamoyl)-biphenyl-3-carboxylic acid 1-methyl-piperidin-4-yl ester | 48 | 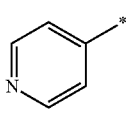 | —H | IIa | 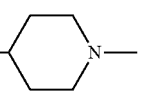 |

TABLE 1-continued

| Name | Cpd | Ar | —R¹ | Formula | —R²¹ |
|---|---|---|---|---|---|
| 2'-Aminomethyl-5'-(pyridin-4-ylcarbamoyl)-biphenyl-3-carboxylic acid 2-oxo-[1,3]dioxolan-4-yl ester | 49 | 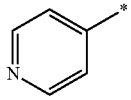 | —H | IIa | 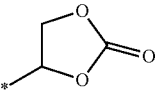 |
| 2'-Aminomethyl-5'-(pyridin-4-ylcarbamoyl)-biphenyl-3-carboxylic acid 5-methyl-2-oxo-[1,3]dioxol-4-ylmethyl ester | 50 | 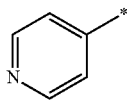 | —H | IIa | 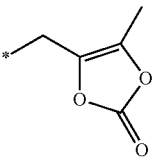 |
| 2'-Aminomethyl-5'-(pyridin-4-ylcarbamoyl)-biphenyl-3-carboxylic acid adamantan-1-ylmethyl ester | 51 | 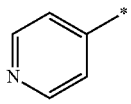 | —H | IIa | 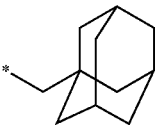 |
| 2'-Aminomethyl-5'-(pyridin-4-ylcarbamoyl)-biphenyl-3-carboxylic acid chloromethyl ester | 52 | 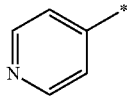 | —H | IIa |  |
| 2'-Aminomethyl-5'-(pyridin-4-ylcarbamoyl)-biphenyl-3-carboxylic acid 2-fluoro-phenyl ester | 53 | 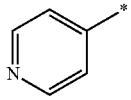 | —H | IIa | 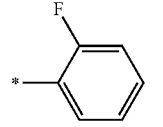 |
| 2'-Aminomethyl-5'-(pyridin-4-ylcarbamoyl)-biphenyl-3-carboxylic acid thiophen-2-ylmethyl ester | 54 | 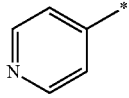 | —H | IIa | 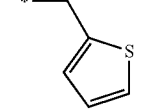 |
| 2'-Aminomethyl-5'-(pyridin-4-ylcarbamoyl)-biphenyl-3-carboxylic acid 2,3-dihydro-benzo[1,4]dioxin-2-ylmethyl ester | 55 | 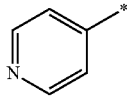 | —H | IIa | 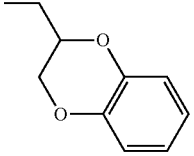 |
| 2'-(1-Amino-ethyl)-5'-(pyridin-4-ylcarbamoyl)-biphenyl-3-carboxylic acid 2,3-dihydro-benzo[1,4]dioxin-2-ylmethyl ester | 56 | 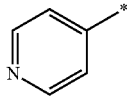 | —Me | IIa | 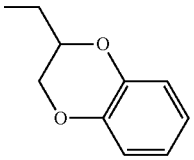 |
| 2'-Aminomethyl-5'-(pyridin-4-ylcarbamoyl)-biphenyl-3-carboxylic acid butyryloxymethyl ester | 57 | 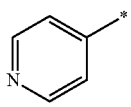 | —H | IIa | 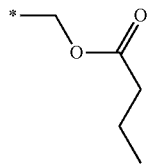 |
| 2'-(2-Amino-ethyl)-5'-(pyidin-4-ylcarbamoyl)-biphenyl-3-carboxylic acid prop-2-ynyl ester | 58 | 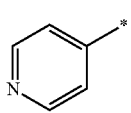 | —Me | IIa | 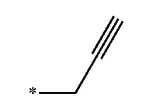 [SMILES: *CC#C] |

TABLE 1-continued

| Name | Cpd | Ar | —R¹ | Formula | —R²¹ |
|---|---|---|---|---|---|
| 2'-(1-Amino-ethyl)-5'-(pyridin-4-ylcarbamoyl)-biphenyl-3-carboxylic acid but-2-ynyl ester | 59 | 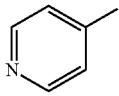 | —Me | IIa | 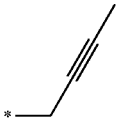 |
| 2'-(1-Amino-ethyl)-5'-(pyridin-4-ylcarbamoyl)-biphenyl-3-carboxylic acid 2-fluoro-ethyl ester | 60 | 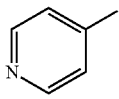 | —Me | IIa | 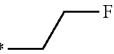 |
| 2'-(1-Amino-ethyl)-5'-(3-fluoro-pyridin-4-ylcarbamoyl)-biphenyl-3-carboxylic acid 2-fluoro-ethyl ester | 61 | 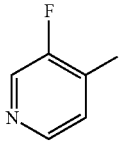 | —Me | IIa | 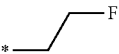 |
| 2'-(1-Amino-ethyl)-5'-(pyridin-4-ylcarbamoyl)-biphenyl-3-carboxylic acid 2-chloro-ethyl ester | 62 | 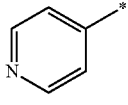 | —Me | IIa | 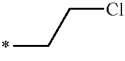 |
| 2'-(1-Amino-ethyl)-5'-(pyridin-4-ylcarbamoyl)-biphenyl-3-carboxylic acid 2,2,2-trifluoro-ethyl ester | 63 | 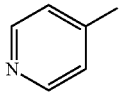 | —Me | IIa | 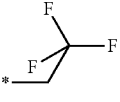 |
| 2'-(1-Amino-ethyl)-5'-(pyridin-4-ylcarbamoyl)-biphenyl-3-carboxylic acid 2,2,2-trichloro-ethyl ester | 64 | 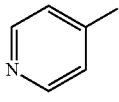 | —Me | IIa | 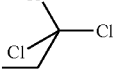 |
| 2'-(1-Amino-ethyl)-5'-(pyridin-4-ylcarbamoyl)-biphenyl-3-carboxylic acid 2-hydroxy-ethyl ester | 65 | 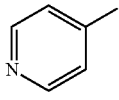 | —Me | IIa |  |
| 2'-(1-Amino-ethyl)-5'-(pyridin-4-ylcarbamoyl)-biphenyl-3-carboxylic acid 3-hydroxy-propyl ester | 66 | 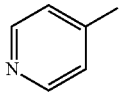 | —Me | IIa | 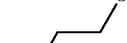 |
| 2'-(1-Amino-ethyl)-5'-(3-fluoro-pyridin-4-ylcarbamoyl)-biphenyl-3-carboxylic acid 2-hydroxy-ethyl ester | 67 | 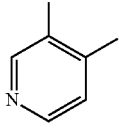 | —Me | IIa |  |
| 2'-(1-Amino-ethyl)-5'-(3-fluoro-pyridin-4-ylcarbamoyl)-biphenyl-3-carboxylic acid 3-hydroxy-propyl ester | 68 | 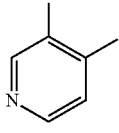 | —Me | IIa | 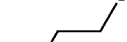 |
| 2'-(1-Amino-ethyl)-5'-(pyridin-4-ylcarbamoyl)-biphenyl-3-carboxylic acid 4-chloro-butyl ester | 69 | 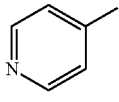 | —Me | IIa |  |
| 2'-(1-Amino-ethyl)-5'-(pyridin-4-ylcarbamoyl)-biphenyl-3-carboxylic acid phenyl ester | 70 | 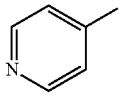 | —Me | IIa |  |

TABLE 1-continued

| Name | Cpd | Ar | —R¹ | Formula | —R²¹ |
|---|---|---|---|---|---|
| 2'-(1-Amino-ethyl)-5'-(3-fluoro-pyridin-4-ylcarbamoyl)-biphenyl-3-carboxylic acid phenyl ester | 71 | 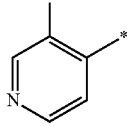 | —Me | IIa | 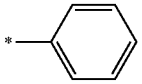 |
| 2'-(1-Amino-ethyl)-5'-(pyridin-4-ylcarbamoyl)-biphenyl-3-carboxylic acid 4-fluoro-phenyl ester | 72 | 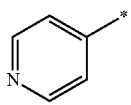 | —Me | IIa |  |
| 2'-(1-Amino-ethyl)-5'-(pyridin-4-ylcarbamoyl)-biphenyl-3-carboxylic acid p-tolyl ester | 73 | 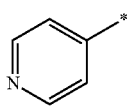 | —Me | IIa | 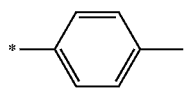 |
| 2'-(1-Amino-ethyl)-5'-(pyridin-4-ylcarbamoyl)-biphenyl-3-carboxylic acid 2,6-dimethoxy-phenyl ester | 74 | 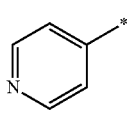 | —Me | IIa | 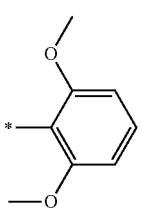 |
| 2'-(1-Amino-ethyl)-5'-(pyridin-4-ylcarbamoyl)-biphenyl-3-carboxylic acid 3,5-dimethoxy-phenyl ester | 75 | 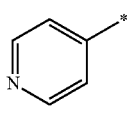 | —Me | IIa | 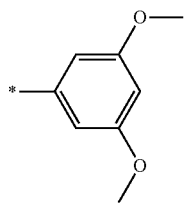 |
| 2'-(1-Amino-ethyl)-5'-(3-fluoro-pyridin-4-ylcarbamoyl)-biphenyl-3-carboxylic acid 3,5-dimethoxy-phenyl ester | 76 | 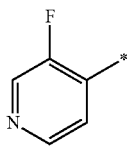 | —Me | IIa | 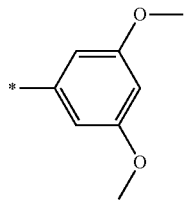 |
| 2'-(1-Amino-ethyl)-5'-(pyridin-4-ylcarbamoyl)-biphenyl-3-carboxylic acid 3,4-dimethoxy-phenyl ester | 77 | 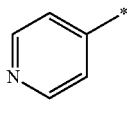 | —Me | IIa | 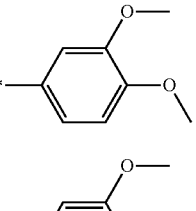 |
| 2'-(1-Amino-ethyl)-5'-(3-fluoro-pyridin-4-ylcarbamoyl)-biphenyl-3-carboxylic acid 3,4-dimethoxy-phenyl ester | 78 | 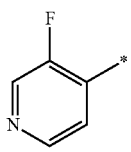 | —Me | IIa | 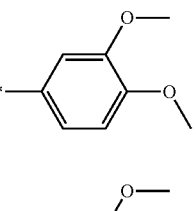 |
| 2'-(1-Amino-ethyl)-5'-(3-fluoro-pyridin-4-ylcarbamoyl)-biphenyl-3-carboxylic acid 3,4,5-trimethoxy phenylester | 79 | 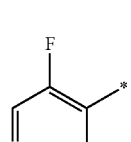 | —Me | IIa | 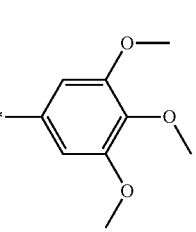 |

TABLE 1-continued

| Name | Cpd | Ar | —R¹ | Formula | —R²¹ |
|---|---|---|---|---|---|
| 2'-(1-Amino-ethyl)-5'-(pyridin-4-ylcarbamoyl)-biphenyl-3-carboxylic acid 3,4,5-trimethoxy-phenyl ester | 80 | 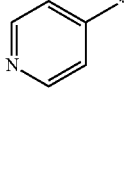 | —Me | IIa | 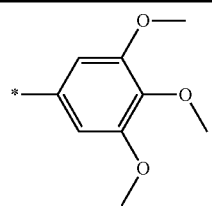 |
| 2'-(1-Amino-ethyl)-5'-(pyridin-4-ylcarbamoyl)-biphenyl-3-carboxylic acid 2,3,4-trimethoxy-phenyl ester | 81 | 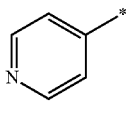 | —Me | IIa | 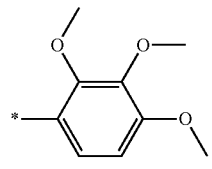 [SMILES: *c1ccc(OC)c(OC)c1OC] |
| 2'-(1-Amino-ethyl)-5'-(pyridin-4-ylcarbamoyl)-biphenyl-3-carboxylic acid 4-methylsulfanyl-phenyl ester | 82 | 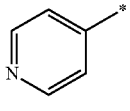 | —Me | IIa | 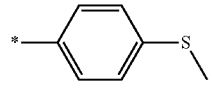 |
| 2'-(1-Amino-ethyl)-5'-(pyridin-4-ylcarbamoyl)-biphenyl-3-carboxylic acid pentafluoro-phenylmethyl ester | 83 | 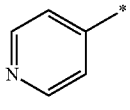 | —Me | IIa | 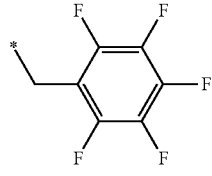 |
| 2'-(1-Amino-ethyl)-5'-(pyridin-4-ylcarbamoyl)-biphenyl-3-carboxylic acid 4-bromo-benzyl ester | 84 | 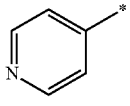 | —Me | IIa | 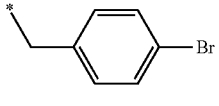 |
| 2'-(1-Amino-ethyl)-5'-(pyridin-4-ylcarbamoyl)-biphenyl-3-carboxylic acid 2-nitro-benzyl ester | 85 | 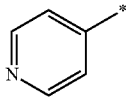 | —Me | IIa | 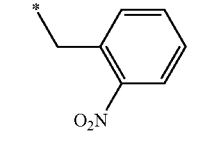 [SMILES: *Cc1ccccc1[N+](=O)[O-]] |
| 2'-(1-Amino-ethyl)-5'-(pyridin-4-ylcarbamoyl)-biphenyl-3-carboxylic acid 4-methylsulfanyl-phenyl ester | 86 | 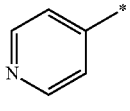 | —Me | IIa | 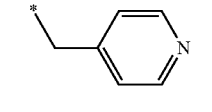 [SMILES: *Cc1ccncc1] |
| 2'-(1-Amino-ethyl)-5'-(pyridin-4-ylcarbamoyl)-biphenyl-3-carboxylic acid phenethyl ester | 87 | 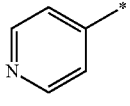 | —Me | IIa | 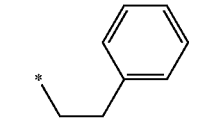 |
| 2'-(1-Amino-ethyl)-5'-(pyridin-4-ylcarbamoyl)-biphenyl-3-carboxylic acid 3-phenoxy-propyl ester | 88 | 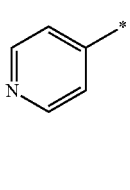 | —Me | IIa | 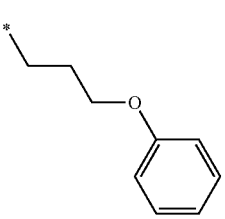 |
| 2'-(1-Amino-ethyl)-5'-(pyridin-4-ylcarbamoyl)-biphenyl-3-carboxylic acid 2-(toluene-4-sulfonyl)-ethyl ester | 89 | 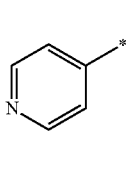 | —Me | IIa | 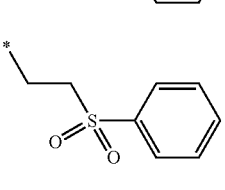 |

TABLE 1-continued

| Name | Cpd | Ar | —R¹ | Formula | —R²¹ |
|---|---|---|---|---|---|
| 2'-(1-Amino-ethyl)-5'-(pyridin-4-ylcarbamoyl)-biphenyl-3-carboxylic acid furan-3-ylmethyl ester | 90 | 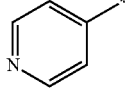 | —Me | IIa | 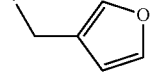 |
| 2'-(1-Amino-ethyl)-5'-(pyridin-4-ylcarbamoyl)-biphenyl-3-carboxylic acid 2-thiophen-2-yl-ethyl ester | 91 | 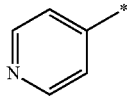 | —Me | IIa | 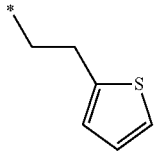 |
| 2'-(1-Amino-ethyl)-5'-(pyridin-4-ylcarbamoyl)-biphenyl-3-carboxylic acid 2-thiophen-3-yl-ethyl ester | 92 | 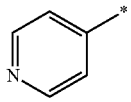 | —Me | IIa | 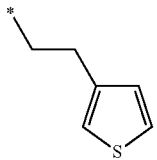 |
| 2'-(1-Amino-ethyl)-5'-(pyridin-4-ylcarbamoyl)-biphenyl-3-carboxylic acid 2-pyridin-2-yl-ethyl ester | 93 | 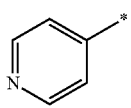 | —Me | IIa | 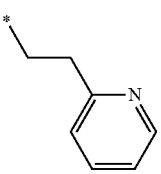 |
| 2'-(1-Amino-ethyl)-5'-(pyridin-4-ylcarbamoyl)-biphenyl-3-carboxylic acid 1,2,3,4-tetrahydro-naphthalen-2-ylmethyl ester | 94 | 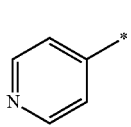 | —Me | IIa | 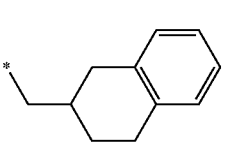 |
| 2'-(1-Amino-ethyl)-5'-(pyridin-4-ylcarbamoyl)-biphenyl-3-carboxylic acid 2-(1,3-dioxo-1,3-dihydro-isoindol-2-yl)-ethyl ester | 95 | 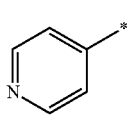 | —Me | IIa | 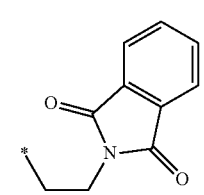 [SMILES: *CCN1C(=O)c2ccccc2C1=O] |
| 2'-(1-Amino-ethyl)-5'-(pyridin-4-ylcarbamoyl)-biphenyl-3-carboxylic acid 2-(4-bromo-phenyl)-2-oxo-ethyl ester | 96 | 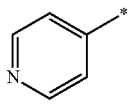 | —Me | IIa | 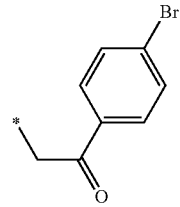 |

Table 2 shows the results for compounds of Formula IIIa or IIIb

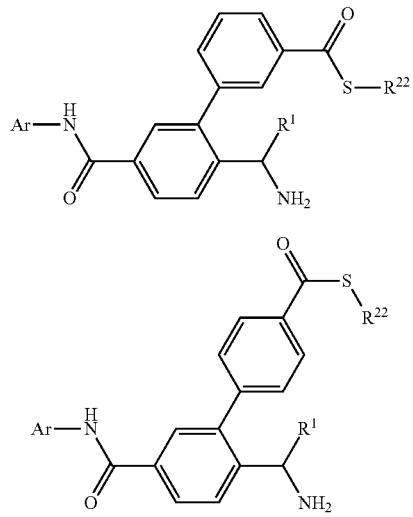

TABLE 2

| Name | Cpd | Ar | —R$^1$ | Formula | —R$^{22}$ |
|------|-----|----|----|---------|-----------|
| 2'-Aminomethyl-5'-(pyridin-4-ylcarbamoyl)-biphenyl-3-carbothioic acid S-ethyl ester | 97 | pyridin-4-yl* | —H | IIIa | *—CH$_2$CH$_3$ |
| 2'-Aminomethyl-5'-(pyridin-4-ylcarbamoyl)-biphenyl-4-carbothioic acid S-ethyl ester | 98 | pyridin-4-yl* | —H | IIIb | *—CH$_2$CH$_3$ |
| 2'-Aminomethyl-5'-(pyridin-4-ylcarbamoyl)-biphenyl-3-carbothioic acid S-fluoromethyl ester | 99 | pyridin-4-yl* | —H | IIIa | *—CH$_2$F |

TABLE 2-continued

| Name | Cpd | Ar | —R$^1$ | Formula | —R$^{22}$ |
|------|-----|----|----|---------|-----------|
| 2'-Aminomethyl-5'-(pyridin-4-ylcarbamoyl)-biphenyl-4-carbothioic acid S-fluoromethyl ester | 100 | pyridin-4-yl* | —H | IIIb | *—CH$_2$F |
| 2'-(1-Amino-ethyl)-5'-(pyridin-4-ylcarbamoyl)-biphenyl-3-carbothioic acid S-tert-butyl ester | 101 | pyridin-4-yl* | —Me | IIIa | *—C(CH$_3$)$_3$ |

Table 3 shows the results for compounds of Formula IVa and IVb.

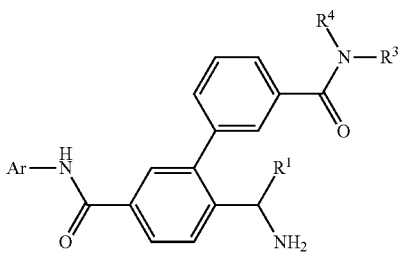

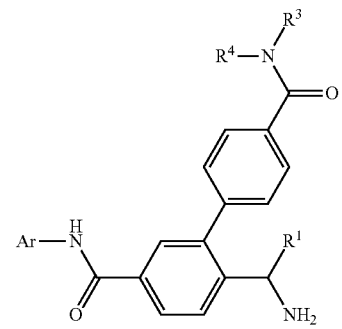

TABLE 3

| Name | Cpd | Ar | Formula | —R$^1$ | —R$^3$ | —R$^4$ |
|------|-----|----|---------|----|----|----|
| {[2'-Aminomethyl-5'-(pyridin-4-ylcarbamoyl)-biphenyl-3-carbonyl]-amino}-acetic acid methyl ester | 102 | pyridin-4-yl* | IVa | —H | —H | *—CH$_2$C(O)OCH$_3$ |
| {[2'-Aminomethyl-5'-(pyridin-4-ylcarbamoyl)-biphenyl-4-carbonyl]-amino}-acetic acid methyl ester | 103 | pyridin-4-yl* | IVb | —H | —H | *—CH$_2$C(O)OCH$_3$ |

TABLE 3-continued

| Name | Cpd | Ar | Formula | —R¹ | —R³ | —R⁴ |
|---|---|---|---|---|---|---|
| {[2'-Aminomethyl-5'-(pyridin-4-ylcarbamoyl)-biphenyl-3-carbonyl]-amino}-acetic acid ethyl ester | 104 |  | IVa | —H | —H | 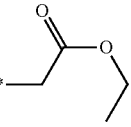 |
| 3-{[2'-(1-Amino-ethyl)-5'-(pyridin-4-ylcarbamoyl)-biphenyl-3-carbonyl]-amino}-propionic acid ethyl ester | 105 |  | IVa | —Me | —H | 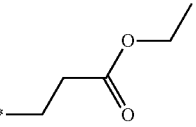 |
| 6-Aminomethyl-biphenyl-3,3'-dicarboxylic acid 3'-carbamoylmethyl-amide 3-pyridin-4-ylamide | 106 |  | IVa | —H | —H | 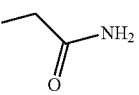 |
| 2-{[2'-Aminomethyl-5'-(pyridin-4-ylcarbamoyl)-biphenyl-3-carbonyl]-amino}-3-methyl-pentanoic acid methyl ester | 107 |  | IVa | —H | —H | 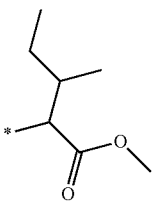 [SMILES: *C(C(=O)OC)C(C)CC] |
| 2-(2-{[2'-Aminomethyl-5'-(pyridin-4-ylcarbamoyl)-biphenyl-3-carbonyl]-amino}-acetylamino)-propionic acid methyl ester | 108 |  | IVa | —H | —H | 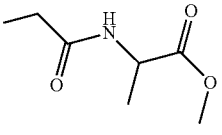 |
| 6-Aminomethyl-biphenyl-3,3'-dicarboxylic acid 3'-{[(carbamoylmethyl-carbamoyl)-methyl]-amide} 3-pyridin-4-ylamide | 109 |  | IVa | —H | —H | 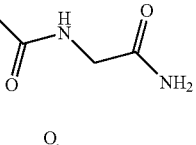 |
| {[2'-Aminomethyl-5'-(pyridin-4-ylcarbamoyl)-biphenyl-3-carbonyl]-amino}-thioacetic acid S-ethyl ester | 110 |  | IVa | —H | —H | 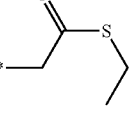 |
| {[2'-Aminomethyl-5'-(pyridin-4-ylcarbamoyl)-biphenyl-3-carbonyl]-amino}-thioacetic acid S-fluoromethyl ester | 111 |  | IVa | —H | —H | 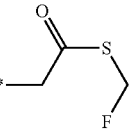 |
| 6-(1-Amino-ethyl)-biphenyl-3,3'-dicarboxylic acid 3'-[(2-oxo-tetrahydro-thiophen-3-yl)-amide] 3-pyridin-4-ylamide | 112 |  | IVa | —Me | —H | 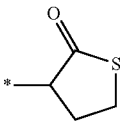 [SMILES: *C1CCSC1=O] |
| 6-Aminomethyl-biphenyl-3,3'-dicarboxylic acid 3'-{[2-(2-oxo-[1,3]dioxolan-4-yl)-ethyl]-amide} 3-pyridin-4-ylamide | 113 |  | IVa | —H | —H | 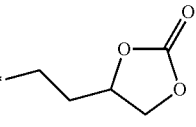 |
| 6-Aminomethyl-biphenyl-3,3'-dicarboxylic acid 3'-{[2-(5-methyl-2-oxo-[1,3]dioxol-4-yl)-ethyl]-amide} 3-pyridin-4-ylamide | 114 |  | IVa | —H | —H | 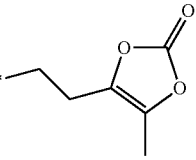 |

TABLE 3-continued

| Name | Cpd | Ar | Formula | —R¹ | —R³ | —R⁴ |
|------|-----|-----|---------|-----|-----|-----|
| 6-Aminomethyl-biphenyl-3,3'-dicarboxylic acid 3'-{[2-(4-oxo-oxetan-2-yl)-ethyl]-amide} 3-pyridin-4-ylamide | 115 |  | IVa | —H | —H | 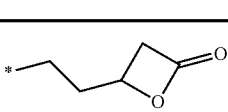 |
| 6-Aminomethyl-biphenyl-3,3'-dicarboxylic acid 3'-{[2-(2-oxo-tetrahydro-pyran-4-yl)-ethyl]-amide} 3-pyridin-4-ylamide | 116 |  | IVa | —H | —H | 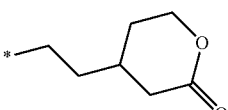 |
| 6-Aminomethyl-biphenyl-3,3'-dicarboxylic acid 3'-{[2-(6-oxo-tetrahydro-pyran-2-yl)-ethyl]-amide} 3-pyridin-4-ylamide | 117 |  | IVa | —H | —H | 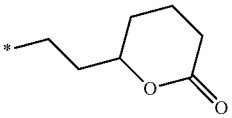 [SMILES: *CCC1CCCC(=O)O1] |
| 6-Aminomethyl-biphenyl-3,3'-dicarboxylic acid 3'-{[2-(2-oxo-tetrahydro-pyran-3-yl)-ethyl]-amide} 3-pyridin-4-ylamide | 118 |  | IVa | —H | —H | 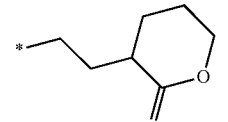 |
| 6-Aminomethyl-biphenyl-3,3'-dicarboxylic acid 3'-{[2-(5-oxo-4,5-dihydro-furan-2-yl)-ethyl]-amide} 3-pyridin-4-ylamide | 119 |  | IVa | —H | —H | 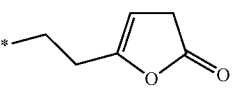 [SMILES: *CCC1=CCC(=O)O1] |
| 6-Aminomethyl-3'-[4-(2-oxo-tetrahydro-furan-3-ylsulfanylmethyl)-piperidine-1-carbonyl]-biphenyl-3-carboxylic acid pyridin-4-ylamide | 120 |  | IVa | —H | | 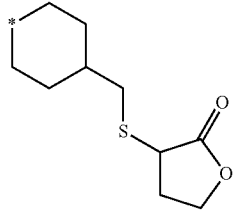 [SMILES: O=C1OCCC1SCC1CC*CC1] |
| 6-Aminomethyl-3'-[4-(2-oxo-tetrahydro-furan-3-yloxymethyl)-piperidine-1-carbonyl]-biphenyl-3-carboxylic acid pyridin-4-ylamide | 121 |  | IVa | —H | | 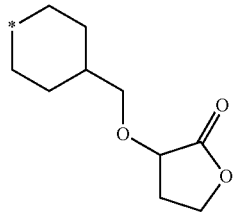 [SMILES: O=C1OCCC1OCC1CC*CC1] |
| 1-[2'-Aminomethyl-5'-(pyridin-4-ylcarbamoyl)-biphenyl-3-carbonyl]-piperidine-2-carboxylic acid methyl ester | 122 |  | IVa | —H | | 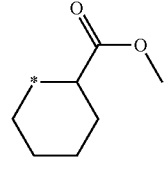 [SMILES: COC(=O)C1*CCCC1] |
| 1-[2'-Aminomethyl-5'-(pyridin-4-ylcarbamoyl)-biphenyl-3-carbonyl]-piperidine-3-carboxylic acid methyl ester | 123 |  | IVa | —H | | 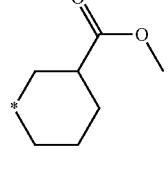 |

TABLE 3-continued

| Name | Cpd | Ar | Formula | —R¹ | —R³ | —R⁴ |
|---|---|---|---|---|---|---|
| 1-[2'-Aminomethyl-5'-(pyridin-4-ylcarbamoyl)-biphenyl-3-carbonyl]-piperidine-4-carboxylic acid methyl ester | 124 |  | IVa | | —H | 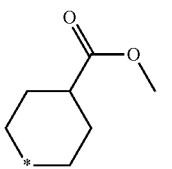 [SMILES: COC(=O)C1CC*CC1] |
| 1-[2'-Aminomethyl-5'-(pyridin-4-ylcarbamoyl)-biphenyl-3-carbonyl]-pyrrolidine-2-carboxylic acid methyl ester | 125 |  | IVa | | —H | 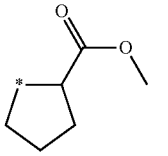 [SMILES: COC(=O)C1*CCC1] |
| ({1-[2'-Aminomethyl-5'-(pyridin-4-ylcarbamoyl)-biphenyl-3-carbonyl]-pyrrolidine-2-carbonyl}-amino)-acetic acid methyl ester | 126 |  | IVa | | —H | 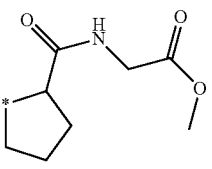 [SMILES: COC(=O)CNC(=O)C1*C(C)CC1] |
| 1-[2'-Aminomethyl-5'-(pyridin-4-ylcarbamoyl)-biphenyl-3-carbonyl]-pyrrolidine-3-carboxylic acid methyl ester | 127 |  | IVa | | —H | 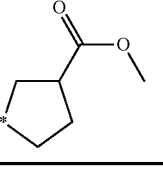 |

Table 4 shows the results for compounds of Formula Va and Vb.

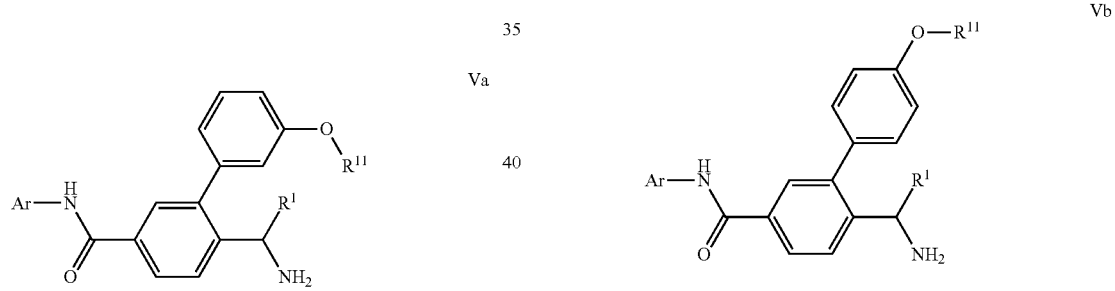

TABLE 4

| Name | Cpd | Ar | —R¹ | Formula | —R¹¹ |
|---|---|---|---|---|---|
| 6-Aminomethyl-3'-[2-(2-oxo-tetrahydro-furan-3-yloxy)-ethoxy]-biphenyl-3-carboxylic acid pyridin-4-ylamide | 128 |  | —H | Va | 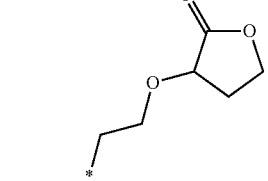 |
| 6-Aminomethyl-3'-[2-(2-oxo-tetrahydro-furan-3-ylsulfanyl)-ethoxy]-biphenyl-3-carboxylic acid pyridin-4-ylamide | 129 |  | —H | Va | 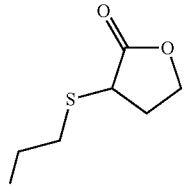 |

TABLE 4-continued

| Name | Cpd | Ar | —R[1] | Formula | —R[11] |
|---|---|---|---|---|---|
| 6-(1-Amino-ethyl)-3'-[2-(2-oxo-tetrahydro-furan-3-ylsulfanyl)-ethoxy]-biphenyl-3-carboxylylic acid pyridin-4-ylamide | 130 |  | —Me | Va | 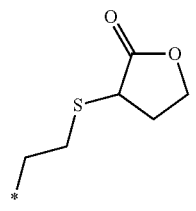 [SMILES: *CCSC1CCOC1=O] |
| 6-(1-Amino-ethyl)-3'-[3-(2-oxo-tetrahydro-furan-3-ylsulfanyl)-propoxy]-biphenyl-3-carboxylylic acid pyridin-4-ylamide | 131 |  | —Me | Va | 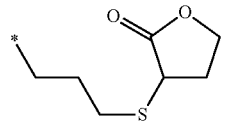 [SMILES: *CCCSC1CCOC1=O] |
| 6-Aminomethyl-3'-(5-methyl-2-oxo-[1,3]dioxol-4-ylmethoxy)-biphenyl-3-carboxylic acid pyridin-4-ylamide | 132 |  | —H | Va | 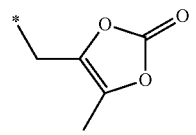 |
| 6-Aminomethyl-3'-(2-oxo-tetrahydro-thiophen-3-ylmethoxy)-biphenyl-3-carboxylic acid pyridin-4-ylamide | 133 |  | —H | Va | 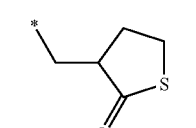 |
| 6-(1-Amino-ethyl)-3'-(2-oxo-tetrahydro-furan-3-yloxy)-biphenyl-3-carboxylic acid pyridin-4-ylamide | 134 |  | —Me | Va | 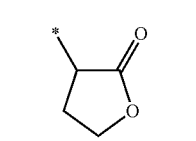 |

Table 5 shows the results for compounds of Formula VIa and VIb.

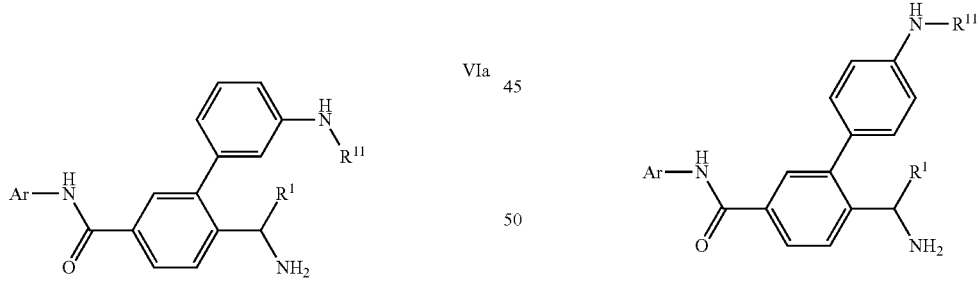

TABLE 5

| Name | Cpd | Ar | —R[1] | Formula | —R[5] |
|---|---|---|---|---|---|
| 6-Aminomethyl-3'-[2-(2-oxo-tetrahydro-furan-3-yloxy)-ethylamino]-biphenyl-3-carboxylic acid pyridin-4-ylamide | 135 |  | —H | VIa | 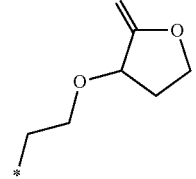 |

TABLE 5-continued

| Name | Cpd | Ar | —R¹ | Formula | —R⁵ |
|---|---|---|---|---|---|
| 6-Aminomethyl-3'-[2-(2-oxo-tetrahydro-furan-3-ylsulfanyl)-ethylamino]-biphenyl-3-carboxylic acid pyridin-4-ylamide | 136 |  | —H | VIa | 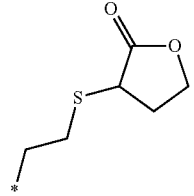 [SMILES: *CCSC1CCOC1=O] |

Table 6 shows the results for compounds of Formula VIIa and VIIb.

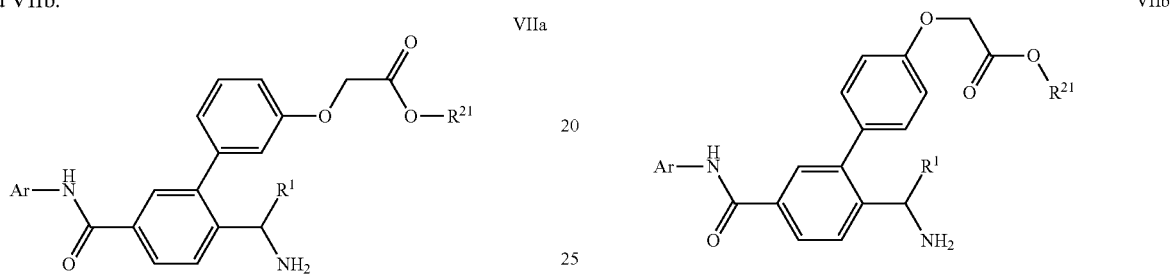

TABLE 6

| Name | Cpd | Ar | —R¹ | Formula | —R²¹ |
|---|---|---|---|---|---|
| [2'-Aminomethyl-5'-(pyridin-4-ylcarbamoyl)-biphenyl-3-yloxy]-acetic acid methyl ester | 137 | 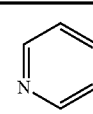 | —H | VIIa | —Me |
| [2'-Aminomethyl-5'-(pyridin-4-ylcarbamoyl)-biphenyl-4-yloxy]-acetic acid methyl ester | 138 | 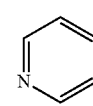 | —H | VIIb | —Me |
| [2'-Aminomethyl-5'-(pyridin-4-ylcarbamoyl)-biphenyl-3-yloxy]-acetic acid 2,3-dihydro-benzo[1,4]dioxin-2-ylmethyl ester | 139 | 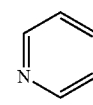 | —H | VIIa | 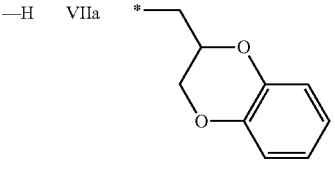 |
| [2'-Aminomethyl-5'-(pyridin-4-ylcarbamoyl)-biphenyl-3-yloxy]-acetic acid propoxycarbonylmethyl ester | 140 | 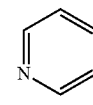 | —H | VIIa | 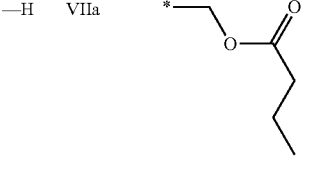 |
| [2'-(1-Amino-ethyl)-5'-(3-fluoro-pyridin-4-ylcarbamoyl)-biphenyl-3-yloxy]-acetic acid propyl ester | 141 | 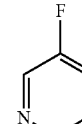 | —Me | VIIa | 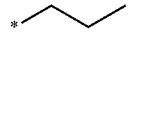 |
| [2'-(1-Amino-ethyl)-5'-(3-fluoro-pyridin-4-ylcarbamoyl)-biphenyl-3-yloxy]-acetic acid phenyl ester | 142 | 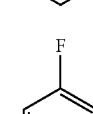 | —Me | VIIa | 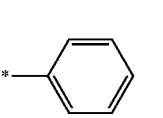 |

Table 7 shows the results for compounds of Formula VIIIa and VIIIb.

Table 8 shows the results for compounds of Formula IXa and IXb.

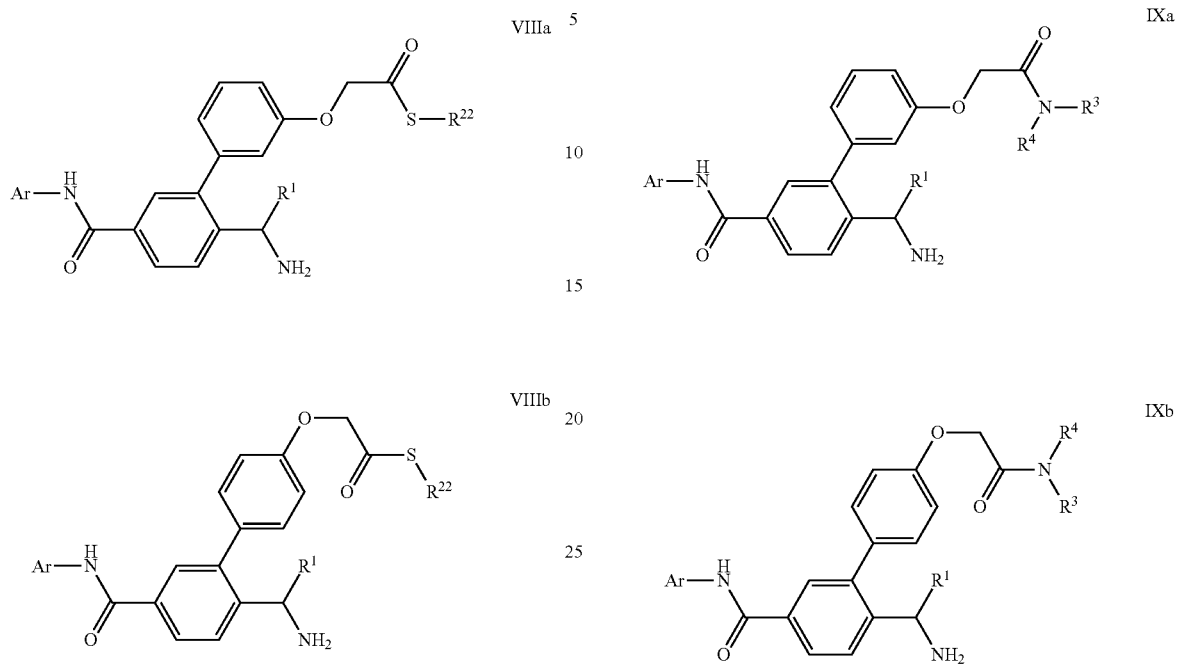

TABLE 7

| Name | Cpd | Ar | —R¹ | Formula | —R²² |
|---|---|---|---|---|---|
| [2'-Aminomethyl-5'-(pyridin-4-ylcarbamoyl)-biphenyl-3-yloxy]-thioacetic acid S-ethyl ester | 143 | pyridin-4-yl | —H | VIIIa | ethyl |
| [2'-Aminomethyl-5'-(pyridin-4-ylcarbamoyl)-biphenyl-3-yloxy]-thioacetic acid S-fluoromethyl ester | 144 | pyridin-4-yl | —H | VIIIa | fluoromethyl |
| [2'-Aminomethyl-5'-(pyridin-4-ylcarbamoyl)-biphenyl-4-yloxy]-thioacetic acid S-ethyl ester | 145 | pyridin-4-yl | —H | VIIIb | ethyl |
| [2'-Aminomethyl-5'-(pyridin-4-ylcarbamoyl)-biphenyl-4-yloxy]-thioacetic acid S-fluoromethyl ester | 146 | pyridin-4-yl | —H | VIIIb | fluoromethyl |

TABLE 8

| Name | Cpd | Ar | Formula | —R¹ | —R³ | —R⁴ |
|---|---|---|---|---|---|---|
| {2-[2'-Aminomethyl-5'-(pyridin-4-ylcarbamoyl)-biphenyl-3-yloxy]-acetylamino}-acetic acid methyl ester | 147 | pyridin-4-yl | IXa | —H | —H | methyl acetate |
| {2-[2'-Aminomethyl-5'-(3-fluoro-pyridin-4-ylcarbamoyl)-biphenyl-3-yloxy]-acetylamino}-acetic acid methyl ester | 148 | 3-fluoro-pyridin-4-yl | IXa | —H | —H | methyl acetate |
| {2-[2'-Aminomethyl-5'-(1H-pyrrolo[2,3-b]pyridin-4-ylcarbamoyl)-biphenyl-3-yloxy]-acetylamino}-acetic acid methyl ester | 149 | 1H-pyrrolo[2,3-b]pyridin-4-yl | IXa | —H | —H | methyl acetate |
| 3-{[2'-(1-Amino-ethyl)-5'-(pyridin-4-ylcarbamoyl)-biphenyl-3-carbonyl]-amino}-propionic acid ethyl ester | 150 | pyridin-4-yl | IXa | —Me | —H | ethyl propanoate |
| 1-{2-[2'-Aminomethyl-5'-(pyridin-4-ylcarbamoyl)-biphenyl-3-yloxy]-acetyl}-piperidine-4-carboxylic acid ethyl ester | 151 | pyridin-4-yl | IXa | —H |  | ethyl piperidine-4-carboxylate |

Table 9 shows the results for compounds of Formula Xa and Xb.

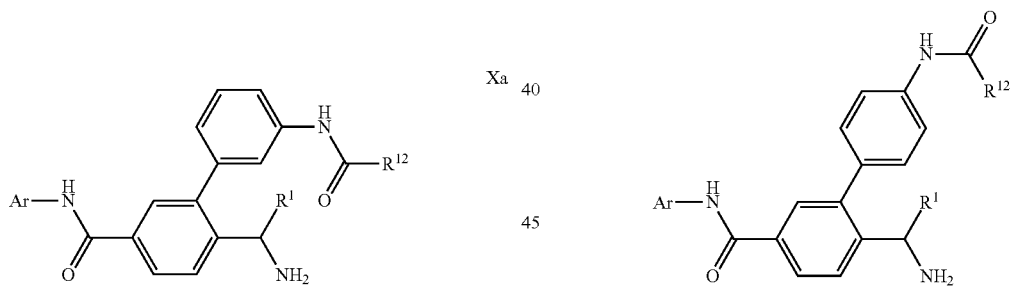

TABLE 9

| Name | Cpd | Ar | —R¹ | Formula | —R¹² |
|---|---|---|---|---|---|
| N-[2'-Aminomethyl-5'-(pyridin-4-ylcarbamoyl)-biphenyl-3-yl]-malonamic acid methyl ester | 152 | pyridin-4-yl | —H | Xa | methyl acetate |
| 6-Aminomethyl-3'-[2-(5-oxo-4,5-dihydro-furan-2-yl)-acetylamino]-biphenyl-3-carboxylic acid pyridin-4-ylamide | 153 | pyridin-4-yl | —H | Xa | (5-oxo-4,5-dihydrofuran-2-yl)methyl |

TABLE 9-continued

| Name | Cpd | Ar | —R¹ | Formula | —R¹² |
|---|---|---|---|---|---|
| {[2'-(1-Aminoethyl)-5'-(pyridin-4-ylcarbamoyl)-biphenyl-3-ylcarbamoyl]-methylsulfanyl}-acetic acid ethyl ester | 154 |  | —Me | Xa | 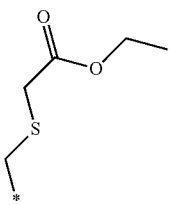 [SMILES: *CSCC(=O)OCC] |
| 6-(1-Amino-ethyl)-3'-[2-(2-oxo-chroman-4-yl)-acetylamino]-biphenyl-3-carboxylic acid pyridin-4-ylamide | 155 |  | —Me | Xa | 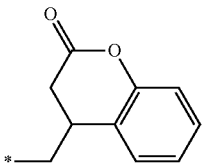 [SMILES: *CC1CC(=O)Oc2ccccc21] |

Table 10 shows the results for compounds of Formula XIII.

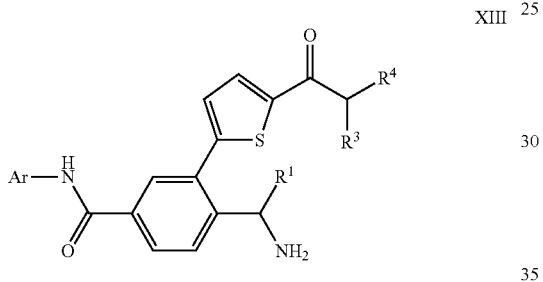

XIII

TABLE 10

| Name | Cpd | Ar | —R¹ | —R³ | —R⁴ |
|---|---|---|---|---|---|
| ({5-[2-Aminomethyl-5-(pyridin-4-ylcarbamoyl)-phenyl]-thiophene-2-carbonyl}-amino)-acetic acid methyl ester | 156 |  | —H | —H | 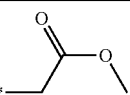 |
| 5-[2-Aminomethyl-5-(pyridin-4-ylcarbamoyl)-phenyl]-thiophene-2-carboxylic acid (2-oxo-tetrahydro-thiophen-3-ylmethyl)-amide | 157 |  | —H | —H | 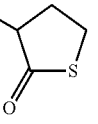 |

Table 11 shows the results for compounds of Formula XIV, XV, XVI and XVII.

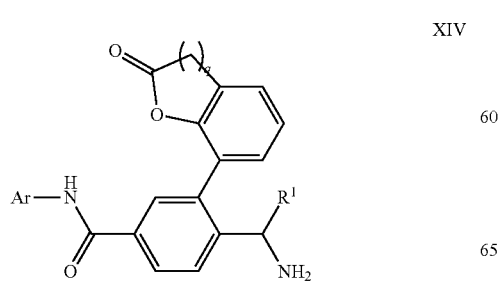

XIV

-continued

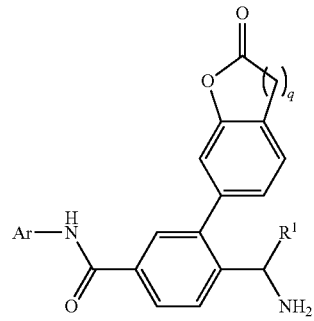

XV

-continued

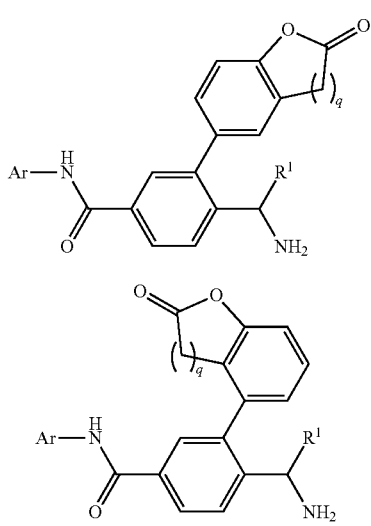

TABLE 11

| Name | Cpd | Ar | —R¹ | q | Formula |
|------|-----|----|----|---|---------|
| 4-Aminomethyl-3-(2-oxo-2,3-dihydro-benzofuran-7-yl)-N-pyridin-4-yl-benzamide | 158 | 3-pyridyl* | —H | 1 | XIV |
| 4-Aminomethyl-3-(2-oxo-2,3-dihydro-benzofuran-6-yl)-N-pyridin-4-yl-benzamide | 159 | 4-pyridyl* | —H | 1 | XV |

Table 12 shows the results for the compounds of Formula XVIIIa.

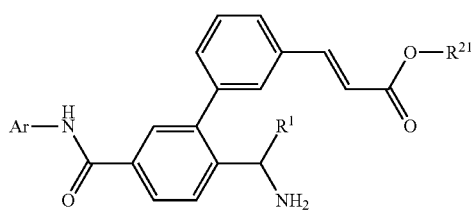

TABLE 12

| Name | Cpd | Ar | —R¹ | R²¹ |
|------|-----|----|----|-----|
| 3-[2'-Aminomethyl-5'-(pyridin-4-ylcarbamoyl)-biphenyl-3-yl]-acrylic acid methyl ester | 160 | 4-pyridyl* | —H | —Me |
| Butyric acid 3-[2'-aminomethyl-5'-(pyridin-4-ylcarbamoyl)-biphenyl-3-yl]-acryloyloxymethyl ester | 161 | 4-pyridyl* | —H | *—CH₂—O—C(O)—CH₂CH₂CH₃ |

Table 13 shows the results for the compounds of Formula XIXa.

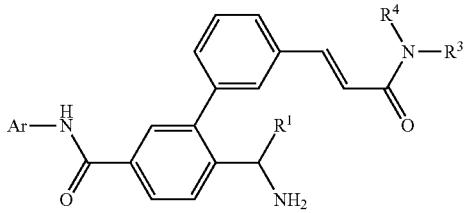

TABLE 13

| Name | Cpd | Ar | —R¹ | R²² |
|------|-----|----|----|-----|
| 3-[2'-Aminomethyl-5'-(pyridin-4-ylcarbamoyl)-biphenyl-3-yl]-thioacrylic acid S-ethyl ester | 162 | 4-pyridyl* | —H | *—CH₂CH₃ |
| 3-[2'-Aminomethyl-5'-(pyridin-4-ylcarbamoyl)-biphenyl-3-yl]-thioacrylic acid S-fluoromethyl ester | 163 | 4-pyridyl* | —H | *—CH₂F |

Table 14 shows the results for the compounds of Formula XXa.

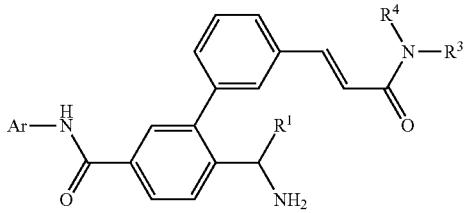

TABLE 14

| Name | Cpd | Ar | —R¹ | R³ | R⁴ |
|---|---|---|---|---|---|
| {3-[2'-Aminomethyl-5'-(pyridin-4-ylcarbamoyl)-biphenyl-3-yl]-acryloylamino}-acetic acid methyl ester | 164 |  | —H | —H | 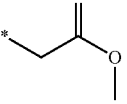 |

Table 15 shows the results for the compounds of Formula XXIa.

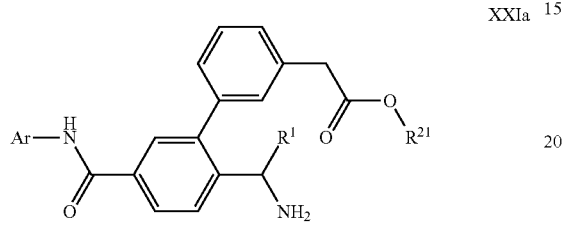

XXIa

TABLE 15

| Name | Cpd | Ar | —R¹ | Formula | R²¹ |
|---|---|---|---|---|---|
| [2'-(1-Amino-ethyl)-5'-(pyridin-4-ylcarbamoyl)-biphenyl-3-yl]-acetic acid phenyl ester | 165 |  | —Me | XXIa |  |

Table 16 shows the results for the compounds of Formula XXIIa.

Table 17 shows the results for the compounds of Formula XXIIIa.

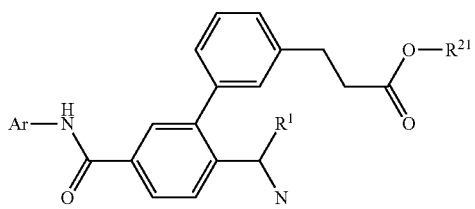

XXIIa

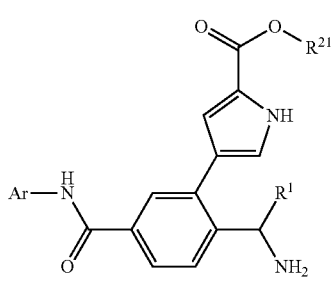

XXIIIa

TABLE 16

| Name | Cpd | Ar | —R¹ | Formula | R²¹ |
|---|---|---|---|---|---|
| 3-[2'-(1-Amino-ethyl)-5'-(pyridin-4-ylcarbamoyl)-biphenyl-3-yl]-propionic acid propyl ester | 166 |  | —Me | XXIIa |  |
| 3-[2'-(1-Amino-ethyl)-5'-(pyridin-4-ylcarbamoyl)-biphenyl-3-yl]-propionic acid phenyl ester | 167 |  | —Me | XXIIa |  |

TABLE 17

| Name | Cpd | Ar | —R¹ | Formula | R²¹ |
|---|---|---|---|---|---|
| 4-[2-(1-Amino-ethyl)-5-(pyridin-4-ylcarbamoyl)-phenyl]-1H-pyrrole-2-carboxylic acid methyl ester | 168 |  | —Me | XXIIIa | —Me |
| 4-[2-(1-Amino-ethyl)-5-(pyridin-4-ylcarbamoyl)-phenyl]-1H-pyrrole-2-carboxylic acid propyl ester | 169 |  | —Me | XXIIIa |  |
| 4-[2-(1-Amino-ethyl)-5-(pyridin-4-ylcarbamoyl)-phenyl]-1H-pyrrole-2-carboxylic acid phenyl ester | 170 |  | —Me | XXIIIa | 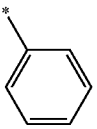 |

Table 18 shows the results for the compounds of Formula XXIVa.

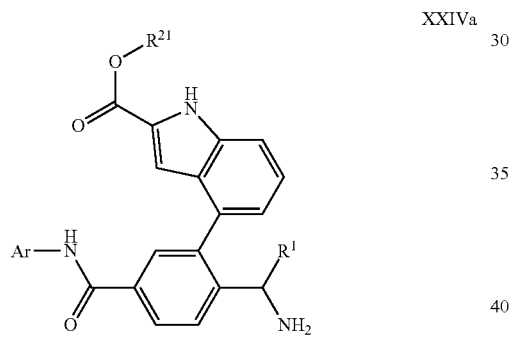

TABLE 18

| Name | Cpd | Ar | —R¹ | Formula | R²¹ |
|---|---|---|---|---|---|
| 4-[2-(1-Amino-ethyl)-5-(pyridin-4-ylcarbamoyl)-phenyl]-1H-indole-2-carboxylic acid methyl ester | 171 |  | —Me | XXIVa | —Me |
| 4-[2-(1-Amino-ethyl)-5-(pyridin-4-ylcarbamoyl)-phenyl]-1H-indole-2-carboxylic acid propyl ester | 172 |  | —Me | XXIVa |  |
| 4-[2-(1-Amino-ethyl)-5-(pyridin-4-ylcarbamoyl)-phenyl]-1H-indole-2-carboxylic acid phenyl ester | 173 |  | —Me | XXIVa |  |

Additional compounds (Table 19):

TABLE 19

| Cpd | Structure | Formula |
|---|---|---|
| 174 | 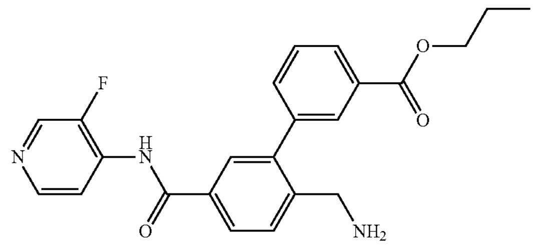 [SMILES: CCCOC(=O)c1cccc(-c2cc(C(=O)Nc3ccncc3F)ccc2CN)c1] | IIa |
| 175 | 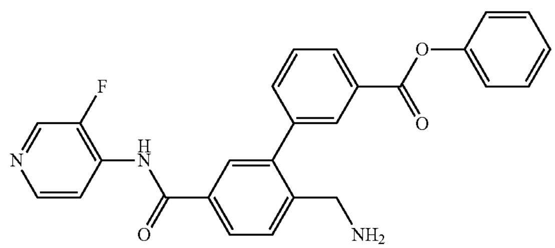 [SMILES: NCc1ccc(C(=O)Nc2ccncc2F)cc1-c1cccc(C(=O)Oc2ccccc2)c1] | IIa |
| 176 | 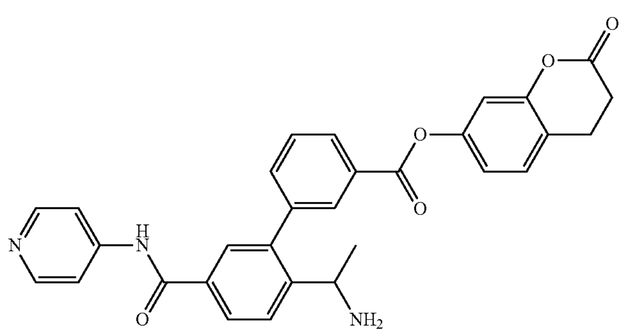 [SMILES: CC(N)c1ccc(C(=O)Nc2ccncc2)cc1-c1cccc(C(=O)Oc2ccc3c(c2)OC(=O)CC3)c1] | IIa |
| 177 | 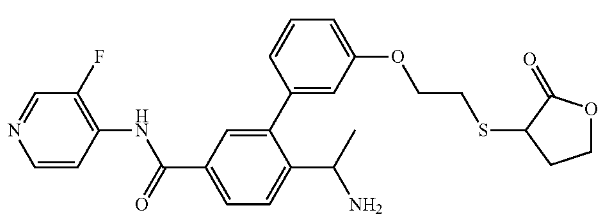 [SMILES: CC(N)c1ccc(C(=O)Nc2ccncc2F)cc1-c1cccc(OCCSC2CCOC2=O)c1] | Va |
| 178 | 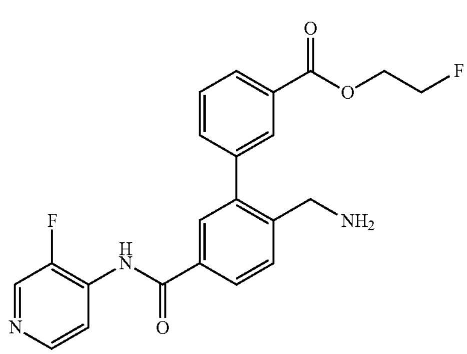 [SMILES: NCc1ccc(C(=O)Nc2ccncc2F)cc1-c1cccc(C(=O)OCCF)c1] | IIa |

US 8,912,209 B2
125
TABLE 19-continued
126
| Cpd | Structure | Formula |
|---|---|---|
| 179 | 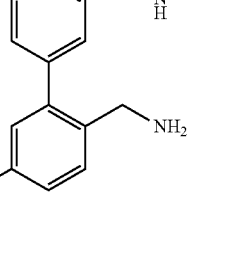 | IVa |
| 180 | 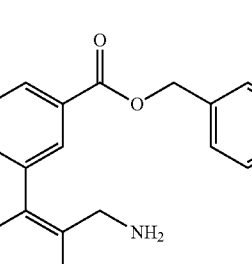 | IIa |
| 181 | 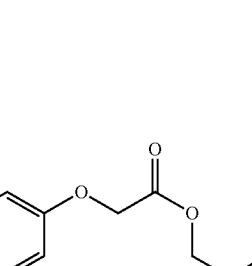 | VIIa |
| 182 | 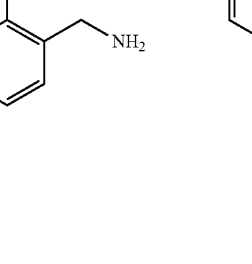 | XXIa |

TABLE 19-continued
| Cpd | Structure | Formula |
|---|---|---|
| 183 | 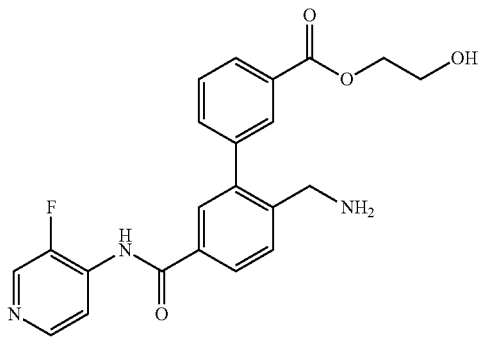 [SMILES: NCc1ccc(C(=O)Nc2ccncc2F)cc1-c1cccc(C(=O)OCCO)c1] | IIa |
| 184 | 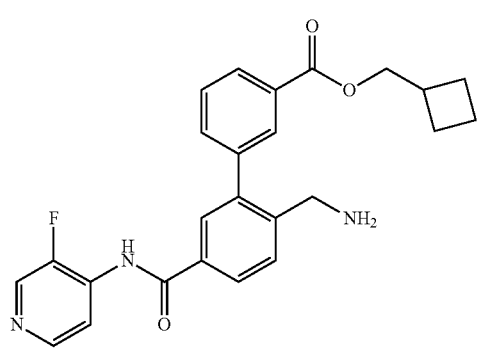 [SMILES: NCc1ccc(C(=O)Nc2ccncc2F)cc1-c1cccc(C(=O)OCC2CCC2)c1] | IIa |
| 185 | 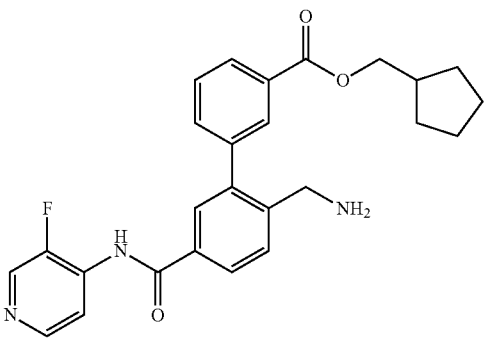 | IIa |
| 186 | 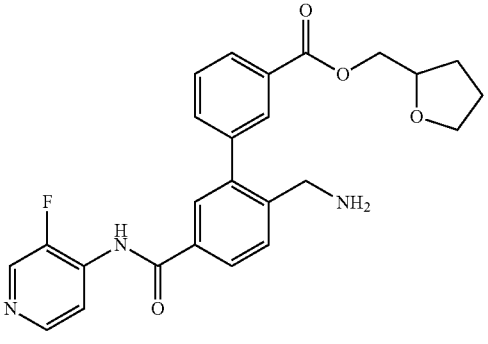 [SMILES: NCc1ccc(C(=O)Nc2ccncc2F)cc1-c1cccc(C(=O)OCC2CCCO2)c1] | IIa |

TABLE 19-continued
| Cpd | Structure | Formula |
|---|---|---|
| 187 | 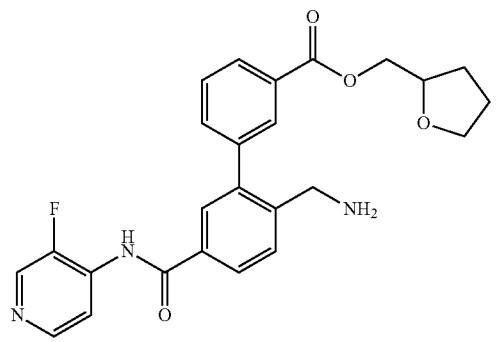 | IIa |
| 188 | 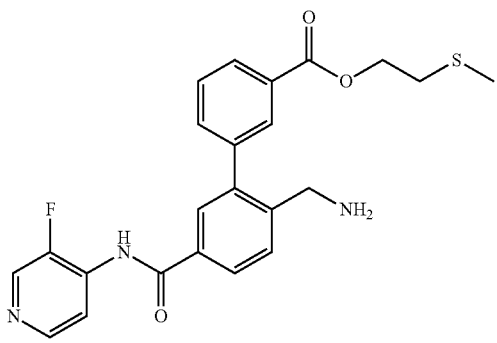 [SMILES: CSCCOC(=O)c1cccc(-c2cc(C(=O)Nc3ccncc3F)ccc2CN)c1] | IIa |
| 188 | 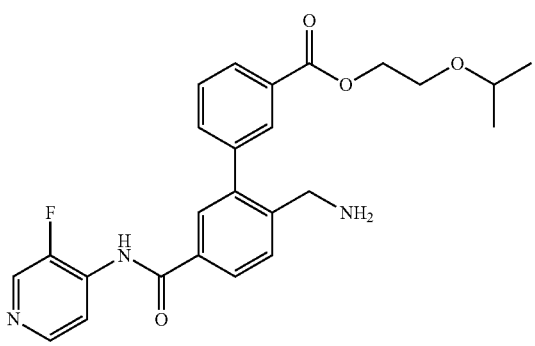 [SMILES: CC(C)OCCOC(=O)c1cccc(-c2cc(C(=O)Nc3ccncc3F)ccc2CN)c1] | IIa |
| 189 | 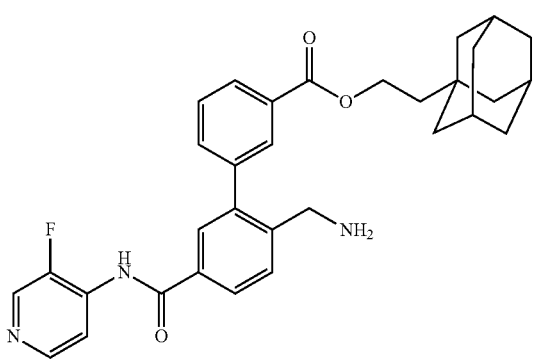 [SMILES: NCc1ccc(C(=O)Nc2ccncc2F)cc1-c1cccc(C(=O)OCCC23CC4CC(CC(C4)C2)C3)c1] | IIa |

US 8,912,209 B2
TABLE 19-continued
| Cpd | Structure | Formula |
|---|---|---|
| 190 | 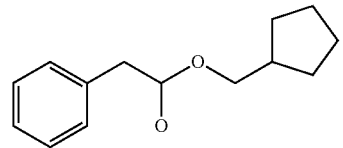 | XXIa |
| 191 | 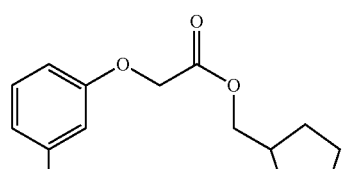 | VIIa |
| 192 | 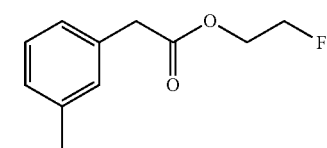 | XXIa |
| 193 | 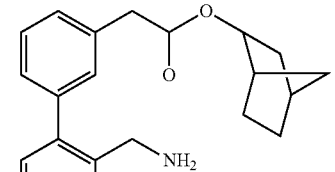 | XXIa |
| 194 | 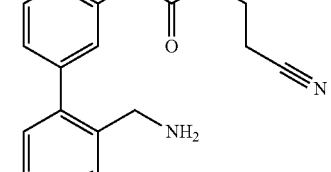 | XXIa |

TABLE 19-continued

| Cpd | Structure | Formula |
|---|---|---|
| 195 | 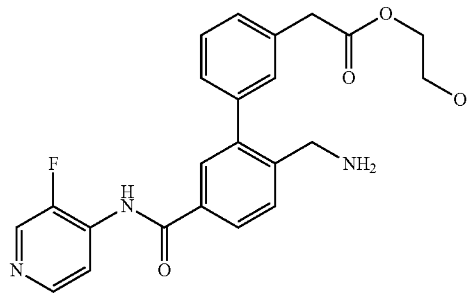 [SMILES: NCc1ccc(C(=O)Nc2ccncc2F)cc1-c1cccc(CC(=O)OCCO)c1] | XXIa |
| 196 | 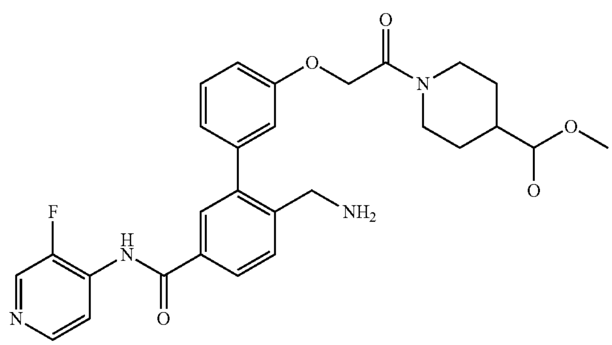 [SMILES: COC(O)C1CCN(C(=O)COc2cccc(-c3cc(C(=O)Nc4ccncc4F)ccc3CN)c2)CC1] | IXa |
| 197 | 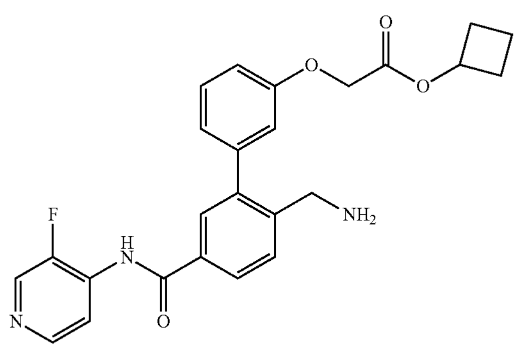 [SMILES: NCc1ccc(C(=O)Nc2ccncc2F)cc1-c1cccc(OCC(=O)OC2CCC2)c1] | VIIa |
| 198 | 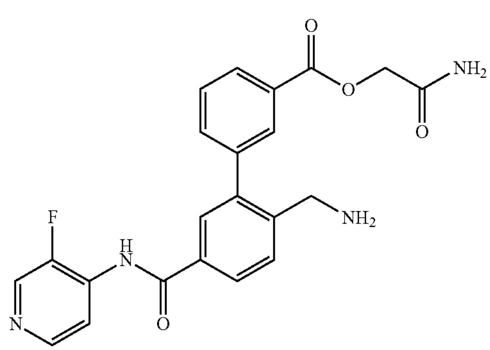 [SMILES: NCc1ccc(C(=O)Nc2ccncc2F)cc1-c1cccc(C(=O)OCC(N)=O)c1] | IIa |

TABLE 19-continued

| Cpd | Structure | Formula |
|---|---|---|
| 199 | 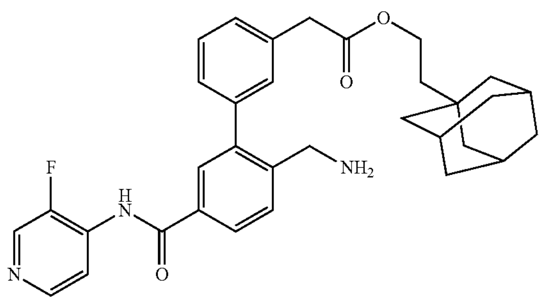 [SMILES: NCc1ccc(C(=O)Nc2ccncc2F)cc1-c1cccc(CC(=O)OCCC23CC4CC(CC(C4)C2)C3)c1] | XXIa |
| 200 | 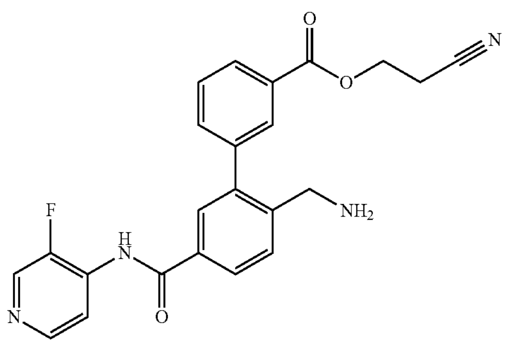 [SMILES: N#CCCOC(=O)c1cccc(-c2cc(C(=O)Nc3ccncc3F)ccc2CN)c1] | IIa |
| 201 | 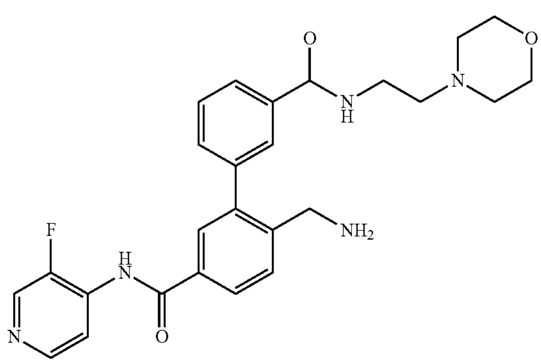 [SMILES: NCc1ccc(C(=O)Nc2ccncc2F)cc1-c1cccc(C(O)NCCN2CCOCC2)c1] | IIa |
| 202 | 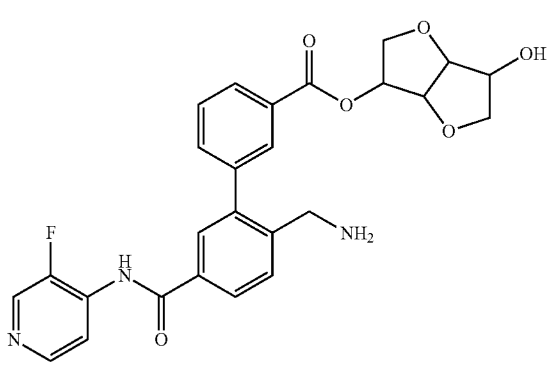 [SMILES: NCc1ccc(C(=O)Nc2ccncc2F)cc1-c1cccc(C(=O)OC2COC3C(O)COC23)c1] | IIa |

TABLE 19-continued

| Cpd | Structure | Formula |
|---|---|---|
| 203 | 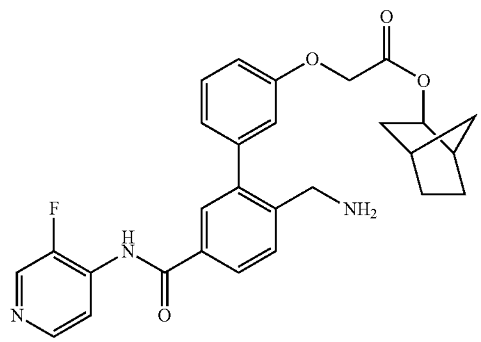 [SMILES: NCc1ccc(C(=O)Nc2ccncc2F)cc1-c1cccc(OCC(=O)OC2CC3CCC2C3)c1] | VIIa |
| 204 | 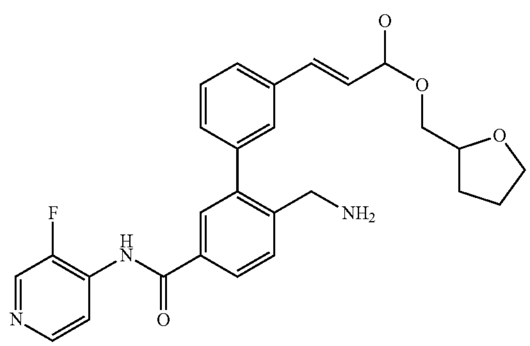 [SMILES: NCc1ccc(C(=O)Nc2ccncc2F)cc1-c1cccc(/C=C/C(O)OCC2CCCO2)c1] | XVIIIa |
| 205 | 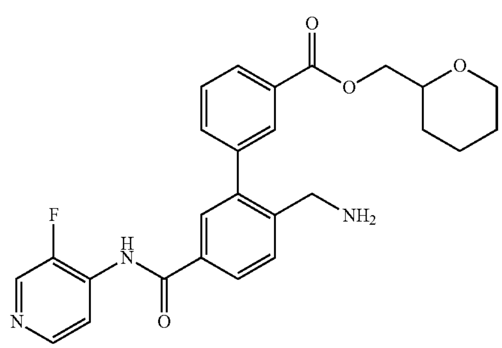 [SMILES: NCc1ccc(C(=O)Nc2ccncc2F)cc1-c1cccc(C(=O)OCC2CCCCO2)c1] | IIa |
| 206 | 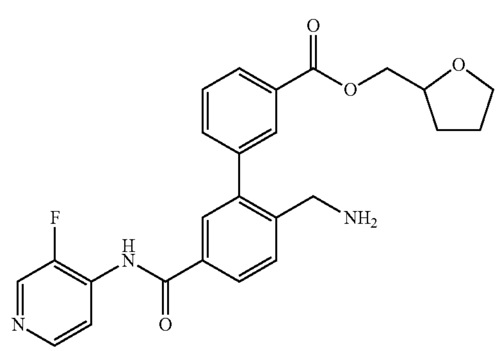 [SMILES: NCc1ccc(C(=O)Nc2ccncc2F)cc1-c1cccc(C(=O)OCC2CCCO2)c1] | IIa |

TABLE 19-continued
| Cpd | Structure | Formula |
|---|---|---|
| 207 | 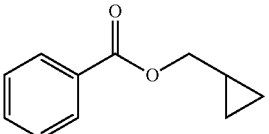 | IIa |
| 208 | 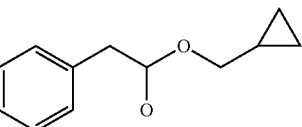 | XXIa |
| 209 | 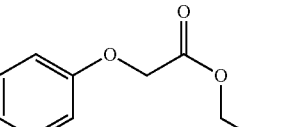 | VIIa |
| 210 | 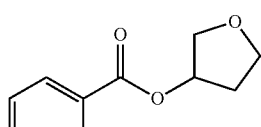 | IIa |

141 142
TABLE 19-continued
| Cpd | Structure | Formula |
|---|---|---|
| 211 | 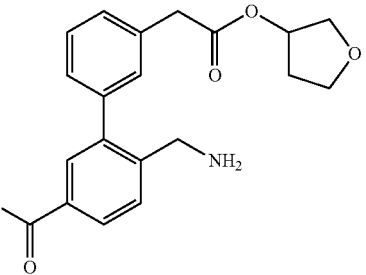 | XXIa |
| 212 | 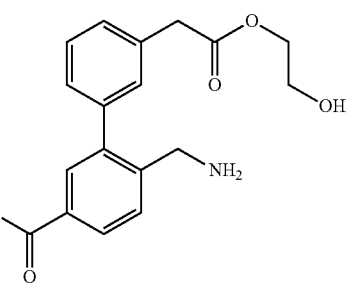 | XXIa |
| 213 | 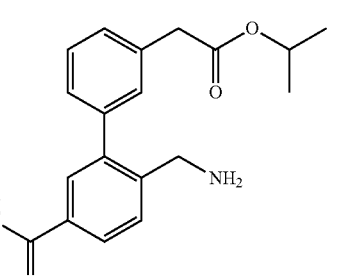 | XXIa |
| 214 | 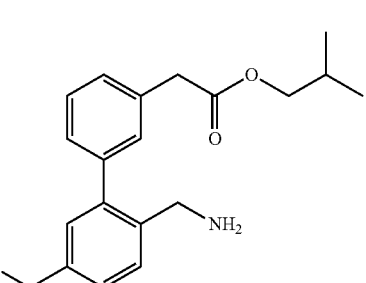 | XXIa |
| 215 | 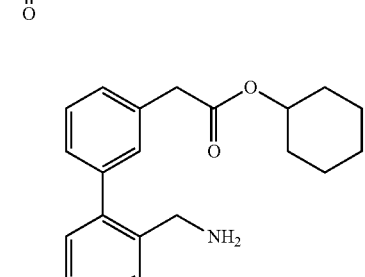 | XXIa |

TABLE 19-continued
| Cpd | Structure | Formula |
|---|---|---|
| 216 | 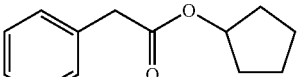 | XXIa |
| 217 | 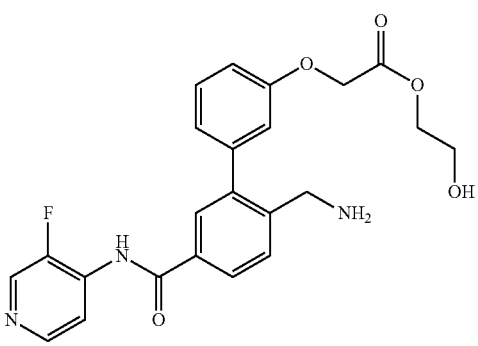 [SMILES: NCc1ccc(C(=O)Nc2ccncc2F)cc1-c1cccc(OCC(=O)OCCO)c1] | VIIa |
| 218 | 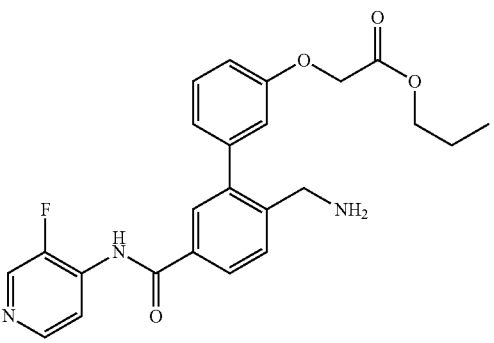 [SMILES: CCCOC(=O)COc1cccc(-c2cc(C(=O)Nc3ccncc3F)ccc2CN)c1] | VIIa |
| 219 | 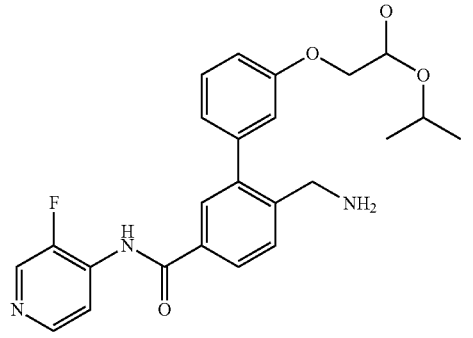 [SMILES: CC(C)OC(O)COc1cccc(-c2cc(C(=O)Nc3ccncc3F)ccc2CN)c1] | VIIa |

TABLE 19-continued

| Cpd | Structure | Formula |
|---|---|---|
| 220 | 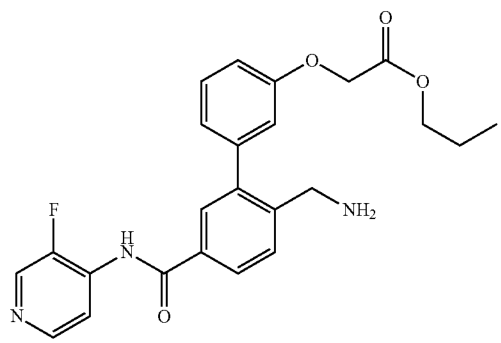 [SMILES: CCCOC(=O)COc1cccc(-c2cc(C(=O)Nc3ccncc3F)ccc2CN)c1] | VIIa |
| 221 | 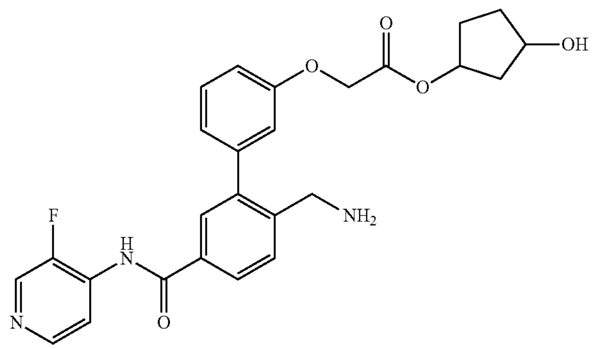 [SMILES: NCc1ccc(C(=O)Nc2ccncc2F)cc1-c1cccc(OCC(=O)OC2CCC(O)C2)c1] | VIIa |
| 222 | 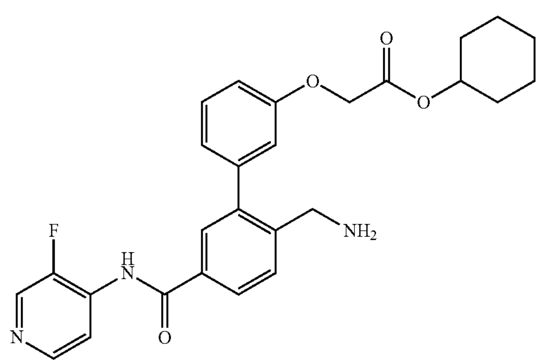 [SMILES: NCc1ccc(C(=O)Nc2ccncc2F)cc1-c1cccc(OCC(=O)OC2CCCCC2)c1] | VIIa |
| 223 | 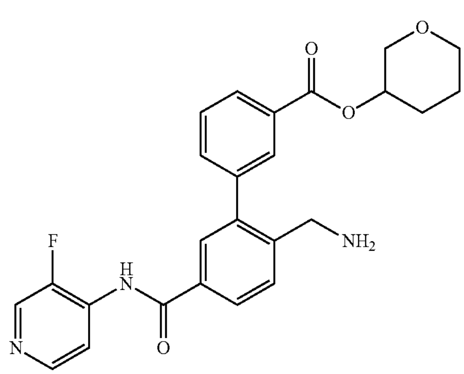 [SMILES: NCc1ccc(C(=O)Nc2ccncc2F)cc1-c1cccc(C(=O)OC2CCCOC2)c1] | IIa |

TABLE 19-continued

| Cpd | Structure | Formula |
|---|---|---|
| 224 | 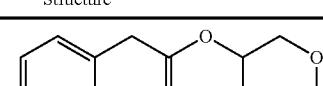 | XXIa |

C. In Vitro and In Vivo Assays

C.1. ROCK Inhibitory Activity Screening
C.1.1. Kinase Inhibition
Method 1—Proqinase Setup A $^{33}$P radioisotopic protein kinase assay is used to determine the $IC_{50}$ for inhibiting ROCK II. A final 50 µl reaction cocktail, containing 60 mM HEPES-NaOH (pH 7.5), 3 mM $MgCl_2$, 3 mM $MnCl_2$, 3 µM Na-orthovanadate, 1.2 mM DTT, 1 µM ATP, 50 µg/ml $PEG_{20.000}$, 1% (v/v) DMSO, 1 µM ATP (approx. $3\times10^5$ cpm $^{33}$P-γ-ATP), the substrate (Substrate: S6 peptide—2000 ng/well) and recombinant protein kinase (0.5 nM-2.5 ng/well) is mixed on a shaker and incubated at 30° C. for 80 minutes. The reaction is stopped by the addition of 50 µl of a 2% solution of $H_3PO_4$ and mixed on a shaker. After washing twice with 200 µl of a 0.9% solution of NaCl, the dry plate is counted.

Method 2:

The inhibition assays were performed with a fluorescence polarization (FP) assay using the commercially available ROCK IMAP Kit from Molecular Devices (Product ID. No. R8093), essentially in accordance with the protocol supplied by the manufacturer. The S6 ribosomal protein-derived substrate used was (FI)-AKRRRLSSLRA, also obtained from Molecular Devices (Product ID No. R7184). The enzyme mix ROCKα/ROCKII was obtained from Upstate Biotechnology (Product ID No 14-451).

In summary, all compounds were screened in the wells of a 384 well plate for enzymatic inhibition with concentrations varying from 100 µM to 0.3 nM using a stepwise 3 (or 2)-fold dilution. Y compound (Y-27632 commercially available from Tocris) was used as a reference (0.4 µM).

To perform the assay, 1 µl of a solution of the compound to be tested in DMSO (at each concentration) was added to 2 µl of a solution of the enzyme in 10 mM Tris-HCl, 10 mM $MgCl_2$, 0.1% BSA, 0.05% $NaN_3$, pH 7,2. The final concentration of the enzyme was 2.6 nM.

After incubating for 30 minutes at RT, 2 µl of a mixture of ATP and the protein substrate in 10 mM Tris-HCl, 10 mM $MgCl_2$, 0.1% BSA, 0.05% $NaN_3$, pH 7.2 was added. The final concentration of the ATP was 10 µM and final concentration of protein substrate was 0.2 µM.

After incubating for 60 minutes at RT, 12 µl of the IMAP Binding Solution (mix of the IMAP Binding Buffer A (1×) and the IMAP Binding Reagent (from the ROCK IMAP kit)) was added.

The mixture thus obtained (total volume: 17 µl) was incubated for 60 minutes at RT, upon which the fluorescence polarization was measured using an automated plate reader (Perkin Elmer, Model Envision 2100-0010 HTS) with FP filters: excitation filter FITC FP 480 and emission filters FITC FP P-pol 535 and FITC FP S-pol 535 (Perkin-Elmer). The results were fitted to a curve using the XL-Fit algorithm and IC50 values were calculated for each fitted curve, again using the XL-Fit algorithm.

The $IC_{50}$ value for the reference compound (Y compound Y-27632) was 0.4 µM.

The $IC_{50}$ values obtained (in accordance with the protocols set forth above) are represented as follows: "+++" means $IC_{50}$ below 0.1 µM, "++" means IC50 between 0.1 µM and 1 µM; "+" means IC50 between 1 and 10 µM and " " means "not determined yet".

| # Cpds | Meth. 1 | Meth. 2 |
|---|---|---|
| 1 | +++ | |
| 2 | + | |
| 3 | | |
| 4 | | +++ |
| 5 | ++ | +++ |
| 6 | | |
| 7 | ++ | |
| 8 | +++ | +++ |
| 9 | | +++ |
| 10 | ++ | |
| 11 | +++ | +++ |
| 12 | ++ | +++ |
| 13 | +++ | +++ |
| 14 | ++ | |
| 15 | ++ | |
| 16 | | ++ |
| 17 | ++ | |
| 18 | | ++ |
| 19 | | ++ |
| 20 | | + |
| 21 | | + |
| 22 | | + |
| 23 | | + |
| 24 | | + |
| 25 | | ++ |
| 26 | ++ | |
| 27 | | +++ |
| 28 | ++ | ++ |
| 29 | | |
| 30 | | |
| 31 | ++ | |
| 32 | ++ | |
| 33 | | +++ |
| 34 | | +++ |
| 35 | ++ | |
| 36 | | +++ |
| 37 | ++ | +++ |
| 38 | ++ | |
| 39 | ++ | |
| 40 | | +++ |
| 41 | ++ | |
| 42 | ++ | |

| # Cpds | Meth. 1 | Meth. 2 | | # Cpds | Meth. 1 | Meth. 2 |
|---|---|---|---|---|---|---|
| 43 | ++ | | | 120 | | |
| 44 | +++ | +++ | | 121 | | |
| 45 | +++ | +++ | | 122 | + | |
| 46 | ++ | +++ | | 123 | | |
| 47 | ++ | +++ | | 124 | + | |
| 48 | ++ | | | 125 | | |
| 49 | | | | 126 | | |
| 50 | | | | 127 | + | |
| 51 | | | | 128 | | |
| 52 | | | | 129 | | |
| 53 | ++ | | | 130 | | +++ |
| 54 | | | | 131 | ++ | ++ |
| 55 | +++ | | | 132 | | |
| 56 | | ++ | | 133 | | |
| 57 | | | | 134 | ++ | +++ |
| 58 | +++ | +++ | | 135 | | |
| 59 | | +++ | | 136 | ++ | |
| 60 | ++ | +++ | | 137 | ++ | |
| 61 | | ++ | | 138 | | |
| 62 | | +++ | | 139 | | |
| 63 | | ++ | | 140 | | |
| 64 | | +++ | | 141 | | ++ |
| 65 | +++ | +++ | | 142 | | ++ |
| 66 | | | | 143 | ++ | |
| 67 | | +++ | | 144 | | |
| 68 | | +++ | | 145 | | |
| 69 | | +++ | | 146 | | |
| 70 | +++ | +++ | | 147 | +++ | |
| 71 | ++ | ++ | | 148 | | |
| 72 | | +++ | | 149 | | |
| 73 | | +++ | | 150 | | |
| 74 | | ++ | | 151 | | |
| 75 | | +++ | | 152 | | |
| 76 | | ++ | | 153 | | |
| 77 | | +++ | | 154 | | +++ |
| 78 | | +++ | | 155 | | +++ |
| 79 | | +++ | | 156 | | |
| 80 | | ++ | | 157 | | |
| 81 | | +++ | | 158 | | |
| 82 | | +++ | | 159 | | |
| 83 | | ++ | | 160 | | |
| 84 | | ++ | | 161 | | |
| 85 | | ++ | | 162 | | |
| 86 | | +++ | | 163 | | |
| 87 | | ++ | | 164 | | |
| 88 | +++ | ++ | | 165 | | |
| 89 | | ++ | | 166 | ++ | ++ |
| 90 | +++ | ++ | | 167 | ++ | +++ |
| 91 | | ++ | | 168 | ++ | ++ |
| 92 | | ++ | | 169 | +++ | |
| 93 | | +++ | | 170 | ++ | +++ |
| 94 | | ++ | | 171 | ++ | |
| 95 | | ++ | | 172 | ++ | ++ |
| 96 | | +++ | | 173 | | ++ |
| 97 | +++ | | | 174 | | ++ |
| 98 | | | | 175 | | +++ |
| 99 | | | | 176 | | +++ |
| 100 | | | | 177 | | ++ |
| 101 | | +++ | | 178 | ++ | |
| 102 | +++ | | | 179 | ++ | |
| 103 | | | | 180 | ++ | |
| 104 | | | | 181 | + | |
| 105 | | +++ | | 182 | ++ | |
| 106 | +++ | | | 183 | ++ | |
| 107 | | | | 184 | ++ | |
| 108 | | | | 185 | ++ | |
| 109 | | | | 186 | | |
| 110 | | | | 187 | ++ | |
| 111 | | | | 188 | + | |
| 112 | | +++ | | 189 | ++ | |
| 113 | ++ | | | 190 | ++ | |
| 114 | | | | 191 | ++ | |
| 115 | | | | 192 | + | |
| 116 | | | | 193 | ++ | |
| 117 | | | | 194 | + | |
| 118 | | | | 195 | + | |
| 119 | | | | 196 | | |

-continued

| # Cpds | Meth. 1 | Meth. 2 |
| --- | --- | --- |
| 197 | | |
| 198 | | |
| 199 | | |
| 200 | | |
| 201 | | |
| 202 | | |
| 203 | | |
| 204 | | |
| 205 | | |
| 206 | | |
| 207 | | |
| 208 | | |
| 209 | | |
| 210 | | |
| 211 | | |
| 212 | | |
| 213 | | |
| 214 | | |
| 215 | | |
| 216 | | |
| 217 | | |
| 218 | | |
| 219 | | |
| 220 | | |
| 221 | | |
| 222 | | |
| 223 | | |
| 224 | | |

C.1.2. Activity Against ROCK in a Cellular Assay Using LPS-Stimulated PBMC in the Absence and Presence of Plasma To ensure the stimulation of PBMC by LPS, the medium is enriched with LPS-binding protein (LBP) that will facilitate the delivery of LPS to the CD14 receptor and enhance the LPS-induced immune response. Cytokines secreted by activated PBMC include TNF, which is detected by means of a colorimetric ELISA. In the presence of an active compound, the release of TNF is inhibited in a concentration-dependent manner. Subsequently a control assay using the same set up in the presence of plasma is included.

For example compound 46 showed $IC_{50}$ 120 nM (assay without plasma) whereas is inactive ($IC_{50}$>10 µM) in the presence of plasma.

C.1.3. Smooth Muscle Relaxing Activity of Generated Soft ROCK Inhibitors In Vitro Using Organ Baths of Guinea Pig Trachea Guinea pig trachea rings are prepared and incubated with a fixed concentration of the bronchoconstrictive agent carbachol. Then, increasing concentrations of the soft ROCK inhibitors are added and the contractive properties of the trachea measured for each of the compound concentrations. The study set-up allows the determination of an $IC_{50}$, represented by the concentration of compound that induces a force equal to 50% of that observed for the vehicle-treated trachea.

In addition retention on the target is assessed using the above described organ baths of guinea pig trachea. In brief, upon induction of maximal relaxation with the ROCK inhibitors, trachea rings are thoroughly washed. Then, carbachol is added again and contractive properties are measured to determine whether the inhibitory activity of the ROCK inhibitors is prolonged upon the washout. A prolonged inhibitory activity after the washout is highly indicative for a prolonged retention of the compound at the lungs in vivo.

For example compound 46 showed $IC_{50}$ of 500 nM.

C.2. Pharmacological Characterization

C.2.1. Stability Assay in Human and/or Rat Plasma

Compounds are incubated at a concentration of 1 µM in rat (mice or rabbit) or human plasma. Samples are taken at fixed time points and the remnant of compound is determined by LC-MS/MS after protein precipitation. Half life is expressed in minutes.

| # Cpd | t½ rat plasma | t½ human plasma |
| --- | --- | --- |
| 46 | 5.8 | 1.9 |
| 47 | 4.5 | 9.8 |
| 97 | 38 | 44 |
| 137 | <1 | 1.9 | i) C.2.2. Stability Towards Drug Metabolizing Enzymes in Lung S9

A 1 µM solution of the ROCK inhibitors is incubated with a reaction mixture containing lung S9 (from smokers) as well as the cofactors NADPH, UDPGA, PAPS and GSH. Samples are collected at 0, 15, 30 and 60 minutes post incubation. Negative control samples incubated with ROCK inhibitors and S9 fraction in the absence of cofactors are run in parallel. By using LC-MS/MS analysis, the percent of ROCK compounds remaining at each time point, the metabolic half-life of the ROCK compounds (expressed in minutes) and the metabolic half-life of the control compounds are determined.

| # Cpd | t½ human lung S9 |
| --- | --- |
| 46 | 53 |
| 47 | >60 |
| 65 | >60 | i) C.2.3. Stability Assay in Rabbit Aqueous Humor

Compounds are incubated at a concentration of 1 µM in rabbit aqueous humor (AH). Samples are taken at fixed time points and the remnant of compound is determined by LC-MS/MS after protein precipitation.

| # Cpd | t½ rabbits AH |
| --- | --- |
| 46 | >60 |
| 169 | >60 | i) C.2.4. Kinetic Binding Characterization

The assay is based on a reporter displacement binding technology. It involves the use a probe specific for the ATP-binding site of ROCK. A signal is generated when the probe is bound to the active site. In the presence of a ATP competitive ROCK inhibitor, the probe is displaced from the enzyme and the signal is disrupted. The probe displacement is monitored over time and the Kon and Koff constants are determined. Inhibitor mechanism of action is characterized enzymatically using the fluorescence-based OMNIA technology.

C.2.5. Anti-Inflammatory Activity of Generated Soft ROCK Inhibitors in an Acute LPS Lung Challenge Model in Mice Half an hour after intranasal compound administration, mice are challenged intratracheally with LPS. Twenty-four hours later, the mice are sacrificed, bronchoalveolar lavage fluid (BALF) collected and total cell number as well as percentage neutrophils determined. Anti-inflammatory activity is represented by a reduction in the total number of BALF cells and in the number of neutrophils as compared to a non-treated control group).

i) C.2.6. Intraocular Pressure (IOP) Lowering in Normotensive Rats or Rabbits

In normotensive rats, the IOP is measured using a Tonolab tonometer. As the IOP is in the range of 8-12 mmHg (with a mean around 10), a maximum decrease of 3 mmHg is usually observed. Timolol (β-blocker), clonidine (α-agonist) and brimonidine (α2-agonist) decrease the IOP by 2-3 mmHg. In normotensive rabbits, the IOP is in the range of 15-20 mmHg (with a mean around 18), again giving a maximum decrease of 3-4 mmHg.

The invention claimed is:

1. A method for the treatment of an eye disease or disorder selected from the group consisting of retinopathy, optic neuropathy, glaucoma, inflammatory eye diseases and degenerative retinal diseases, comprising:
    administering a compound of Formula IIaa or a stereoisomer, tautomer, racemic, salt, hydrate, or solvate thereof to a subject in need of treatment,

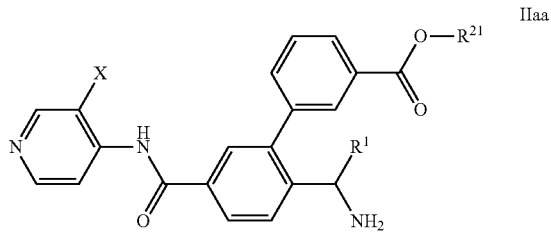

Wherein
X is hydrogen or fluoro;
$R^1$ represents hydrogen or $C_{1-4}$alkyl;
$R^{21}$ is selected from $C_{1-6}$alkyl, 3,4-dihydro-1(2H)-benzopyranyl substituted with oxo, and phenyl.

2. The method of claim 1 wherein X is hydrogen.
3. The method of claim 1 wherein X is fluoro.
4. The method of claim 1, wherein $R^{21}$ is selected from:
    methyl; ethyl; n-propyl; i-propyl; butyl and its isomers; pentyl and its isomers; hexyl and its isomers; cyclopentyl; 2-, 3-, or 4-methylcyclopentyl; cyclopentylmethylene; cyclohexyl;
    3,4-dihydro-1(2H)-benzopyranyl substituted with oxo; and
    phenyl.
5. The method of claim 1, wherein said compound is selected from the group consisting of:
    2'-Aminomethyl-5'-(pyridin-4-ylcarbamoyl)-biphenyl-3-carboxylic acid methyl ester,
    2'-(1-Amino-ethyl)-5'-(pyridin-4-ylcarbamoyl)-biphenyl-3-carboxylic acid methyl ester,
    2'-Aminomethyl-5'-(pyridin-4-ylcarbamoyl)-biphenyl-3-carboxylic acid ethyl ester,
    2'-(1-Amino-ethyl)-5'-(pyridin-4-ylcarbamoyl)-biphenyl-3-carboxylic acid ethyl ester,
    2'-Aminomethyl-5'-(pyridin-4-ylcarbamoyl)-biphenyl-3-carboxylic acid propyl ester,
    2'-(1-Amino-ethyl)-5'-(pyridin-4-ylcarbamoyl)-biphenyl-3-carboxylic acid propyl ester,
    2'-(1-Amino-ethyl)-5'-(3-fluoro-pyridin-4-ylcarbamoyl)-biphenyl-3-carboxylic acid propyl ester,
    2'-(1-Amino-ethyl)-5'-(pyridin-4-ylcarbamoyl)-biphenyl-3-carboxylic acid butyl ester,
    2'-Aminomethyl-5'-(pyridin-4-ylcarbamoyl)-biphenyl-3-carboxylic acid butyl ester,
    2'-(1-Amino-ethyl)-5'-(pyridin-4-ylcarbamoyl)-biphenyl-3-carboxylic acid isopropyl ester,
    2'-(1-Amino-ethyl)-5'-(pyridin-4-ylcarbamoyl)-biphenyl-3-carboxylic acid cyclopropylmethyl ester, and
    2'-Aminomethyl-5'-(pyridin-4-ylcarbamoyl)-biphenyl-3-carboxylic acid cyclopentylmethyl ester.
6. The method of claim 1, wherein said compound is selected from the group consisting of:
    2'-(1-Amino-ethyl)-5'-(3-fluoro-pyridin-4-ylcarbamoyl)-biphenyl-3-carboxylic acid methyl ester,
    2'-(1-Amino-ethyl)-5'-(3-fluoro-pyridin-4-ylcarbamoyl)-biphenyl-3-carboxylic acid ethyl ester,
    2'-(1-Amino-ethyl)-5'-(3-fluoro-pyridin-4-ylcarbamoyl)-biphenyl-3-carboxylic acid cyclopropylmethyl ester,
    propyl 3-[2-(aminomethyl)-5-[(3-fluoropyridin-4-yl)carbamoyl]phenyl]benzoate,
    cyclobutylmethyl 3-[2-(aminomethyl)-5-[(3-fluoropyridin-4-yl)carbamoyl]phenyl]benzoate,
    cyclopentylmethyl 3-[2-(aminomethyl)-5-[(3-fluoropyridin-4-yl)carbamoyl]phenyl]benzoate, and
    cyclopropylmethyl 3-[2-(aminomethyl)-5-[(3-fluoropyridin-4-yl)carbamoyl]phenyl]benzoate.
7. A method for the treatment of an eye disease or disorder selected from the group consisting of retinopathy, optic neuropathy, glaucoma, inflammatory eye diseases and degenerative retinal diseases comprising:
    administering a pharmaceutical composition to a subject in need of treatment, said composition comprising a compound of Formula IIaa or a stereoisomer, tautomer, racemic, salt, hydrate, or solvate thereof,

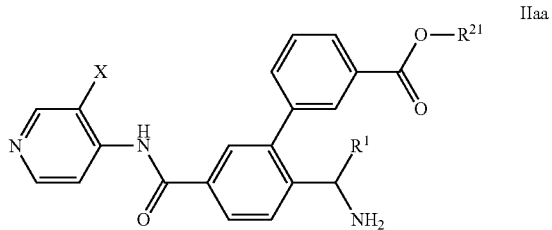

Wherein
X is hydrogen or fluoro;
$R^1$ represents hydrogen or $C_{1-4}$alkyl;
$R^{21}$ is selected from $C_{1-6}$alkyl, 3,4-dihydro-1(2H)-benzopyranyl substituted with oxo, and phenyl.

8. The method of claim 1 wherein said eye disease or disorder is an inflammatory eye disease or disorder.
9. The method of claim 1 wherein said eye disease or disorder is glaucoma.
10. The method of claim 7 wherein said eye disease or disorder is an inflammatory eye disease or disorder.
11. The method of claim 7 wherein said eye disease or disorder is glaucoma.
12. A method for the treatment of elevated intraocular pressure comprising administering to a subject in need of treatment a compound of Formula IIaa as defined in claim 1.

* * * * *